US012673101B2

(12) United States Patent
Martin et al.

(10) Patent No.: US 12,673,101 B2
(45) Date of Patent: Jul. 7, 2026

(54) VARICELLA ZOSTER

(71) Applicant: ADJUVANCE TECHNOLOGIES, INC., Lincoln, NE (US)

(72) Inventors: J Tyler Martin, Roca, NE (US); Jared William Wenger, Lincoln, NE (US); Eric Jon Farris, Lincoln, NE (US); Patrick J Frenchick; Anna Therese Lampe, Lincoln, NE (US)

(73) Assignee: ADJUVANCE TECHNOLOGIES, INC., Lincoln, NE (US)

( * ) Notice: Subject to any disclaimer, the term of this patent is extended or adjusted under 35 U.S.C. 154(b) by 1005 days.

(21) Appl. No.: 17/774,637

(22) PCT Filed: Nov. 4, 2020

(86) PCT No.: PCT/US2020/058859

§ 371 (c)(1),
(2) Date: May 5, 2022

(87) PCT Pub. No.: WO2021/091997

PCT Pub. Date: May 14, 2021

(65) Prior Publication Data

US 2022/0409721 A1 Dec. 29, 2022

Related U.S. Application Data

(60) Provisional application No. 62/930,727, filed on Nov. 5, 2019.

(51) Int. Cl.

| | |
|---|---|
| ***A61K 39/25*** | (2006.01) |
| ***A61K 39/00*** | (2006.01) |
| ***A61K 39/39*** | (2006.01) |

(52) U.S. Cl.
CPC .............. *A61K 39/25* (2013.01); *A61K 39/39* (2013.01); *A61K 2039/55555* (2013.01); *A61K 2039/55566* (2013.01); *A61K 2039/55583* (2013.01)

(58) Field of Classification Search
CPC .................... A61K 39/25; A61K 39/39; A61K 2039/55555; A61K 2039/55566; A61K 2039/55583
See application file for complete search history.

(56) References Cited

U.S. PATENT DOCUMENTS 3,985,615 A 10/1976 Kubo
4,684,479 A 8/1987 D'Arrigo
(Continued)

FOREIGN PATENT DOCUMENTS

CL 2011003113 A1 8/2012
CL 2012000585 A1 9/2012
(Continued)

OTHER PUBLICATIONS

Berge et al. (Journal of Pharmaceutical Sciences, 1977, vol. 66, pp. 1-19) (Year: 1977).*
(Continued)

*Primary Examiner* — Scarlett Y Goon
*Assistant Examiner* — Sarah Grace Hibshman
(74) *Attorney, Agent, or Firm* — Paul D. Strain, Esq.; Strain & Strain PLLC

(57) ABSTRACT

The present application relates to compositions capable of inducing an immune response against Varicella zoster virus, methods of administering such compositions, and methods of producing such compositions.

28 Claims, 29 Drawing Sheets

Specification includes a Sequence Listing.

| | | | | | | |
|---|---|---|---|---|---|---|
| MGTVNKPVVG | VLMGFGIITG | TLRITNPVRA | SVLRYDDFHI | DEDKLDTNSV | YEPYYHSDHA | 60 |
| ESSWVNRGES | SRKAYDHNSP | YIWPRNDYDG | FLENAHEHHG | VYNQGRGIDS | GERLMQPTQM | 120 |
| SAQEDLGDDT | GIHVIPTLNG | DDRHKIVNVD | QRQYGDVFKG | DLNPKPQGQR | LIEVSVEENH | 180 |
| PFTLRAPIQR | IYGVRYTETW | SFLPSLTCTG | DAAPAIQHIC | LKHTTCFQDV | VVDVDCAENT | 240 |
| KEDQLAEISY | RFQGKKEADQ | PWIVVNTSTL | FDELELDPPE | IEPGVLKVLR | TEKQYLGVYI | 300 |
| WNMRGSDGTS | TYATFLVTWK | GDEKTRNPTP | AVTPQPRGAE | FHMWNYHSHV | FSVGDTFSLA | 360 |
| MHLQYKIHEA | PFDLLLEWLY | VPIDPTCQPM | RLYSTCLYHP | NAPQCLSHMN | SGCTFTSPHL | 420 |
| AQRVASTVYQ | NCEHADNYTA | YCLGISHMEP | SFGLILHDGG | TTLKFVDTPE | SLSGLYVFVV | 480 |
| YFNGHVEAVA | YTVVSTVDHF | VNAIEERGFP | PTAGQPPATT | KPKEITPVNP | GTSPLIRYAA | 540 |
| WTGGLA | | | | | | 546 |

(56) References Cited

U.S. PATENT DOCUMENTS

| | | | |
|---|---|---|---|
| 5,215,680 | A | 6/1993 | D'Arrigo |
| 5,874,104 | A | 2/1999 | Adler-Moore et al. |
| 5,916,588 | A | 6/1999 | Popescu et al. |
| 5,965,156 | A | 10/1999 | Proffitt et al. |
| 6,043,094 | A | 3/2000 | Martin et al. |
| 6,056,973 | A | 5/2000 | Allen et al. |
| 6,080,725 | A | 6/2000 | Marciani et al. |
| 6,126,966 | A | 10/2000 | Abra et al. |
| 6,262,029 | B1 | 7/2001 | Press et al. |
| 6,294,191 | B1 | 9/2001 | Meers et al. |
| 6,316,024 | B1 | 11/2001 | Allen et al. |
| 6,352,716 | B1 | 3/2002 | Janoff et al. |
| 6,406,713 | B1 | 6/2002 | Janoff et al. |
| 6,759,057 | B1 | 7/2004 | Weiner et al. |
| 8,283,456 | B2 | 10/2012 | Gin et al. |
| 8,889,842 | B2 | 11/2014 | Gin et al. |
| 9,718,850 | B2 | 8/2017 | Gin et al. |
| 10,906,926 | B2 | 2/2021 | Gin et al. |
| 2003/0095974 | A1 | 5/2003 | Garcon et al. |
| 2009/0035360 | A1 | 2/2009 | Lemoine |
| 2009/0047306 | A1 | 2/2009 | Nash et al. |
| 2010/0272745 | A1 | 10/2010 | Lemoine et al. |
| 2010/0322958 | A1 | 12/2010 | Bardotti et al. |
| 2011/0104260 | A1 | 5/2011 | Hanon et al. |
| 2011/0206758 | A1 | 8/2011 | Vandepapeliere |
| 2012/0087976 | A1 | 4/2012 | Henderickx et al. |
| 2012/0164178 | A1 | 6/2012 | Ballou, Jr. et al. |
| 2013/0011421 | A1 | 1/2013 | Gin et al. |
| 2013/0309273 | A1 | 11/2013 | Hassett et al. |
| 2014/0072622 | A1 | 3/2014 | Denoel et al. |
| 2014/0228286 | A1 | 8/2014 | Luippold et al. |
| 2015/0037374 | A1 | 2/2015 | Bazmorelli et al. |
| 2015/0086585 | A1 | 3/2015 | Gin et al. |
| 2017/0014507 | A1 | 1/2017 | Bazmorelli et al. |
| 2017/0065715 | A1 | 3/2017 | Vandepapeliere |
| 2017/0096444 | A1 | 4/2017 | Gin et al. |
| 2018/0008700 | A1 | 1/2018 | Heineman et al. |
| 2018/0327436 | A1 | 11/2018 | Gin et al. |
| 2019/0275135 | A1 | 9/2019 | Poolman |
| 2020/0164065 | A1 | 5/2020 | Gardner et al. |
| 2020/0239509 | A1 | 7/2020 | Gin et al. |
| 2020/0261571 | A1 | 8/2020 | Martin et al. |
| 2020/0276299 | A1 | 9/2020 | Fox et al. |
| 2021/0002316 | A1 | 1/2021 | Gin et al. |
| 2021/0283248 | A1 | 9/2021 | Livingston et al. |
| 2022/0184207 | A1 | 6/2022 | Martin et al. |
| 2023/0219991 | A1 | 7/2023 | Gin et al. |
| 2023/0357300 | A1 | 11/2023 | Chan et al. |

FOREIGN PATENT DOCUMENTS

| | | | |
|---|---|---|---|
| EP | 0 192 902 | A2 | 9/1986 |
| JP | 2011-516566 | A | 5/2011 |
| WO | WO 93/05789 | A1 | 4/1993 |
| WO | WO 94/02596 | A1 | 2/1994 |
| WO | WO 96/33739 | A1 | 10/1996 |
| WO | WO 2001/015727 | A2 | 3/2001 |
| WO | WO 2006/094756 | A2 | 9/2006 |
| WO | WO 2009/080715 | A2 | 7/2009 |
| WO | WO 2009/126737 | A2 | 10/2009 |
| WO | WO 2010/142685 | A1 | 12/2010 |
| WO | WO 2011/027222 | A2 | 3/2011 |
| WO | WO 2012/158978 | A1 | 11/2012 |
| WO | WO 2015/184451 | A1 | 12/2015 |
| WO | WO 2017/079582 | A1 | 5/2017 |
| WO | WO 2017/106836 | A1 | 6/2017 |
| WO | WO 2018/114892 | A1 | 6/2018 |
| WO | WO 2018/191598 | A1 | 10/2018 |
| WO | WO 2018/198085 | A1 | 11/2018 |
| WO | WO 2018/200645 | A1 | 11/2018 |
| WO | WO 2018/200656 | A1 | 11/2018 |
| WO | WO 2019/079160 | A1 | 4/2019 |
| WO | WO 2021/091997 | A1 | 5/2021 |
| WO | WO 2021/195024 | A1 | 9/2021 |
| WO | WO 2022/221393 | A1 | 10/2022 |

OTHER PUBLICATIONS

Wojtczak, A. (Medical Teacher, 2002, vol. 24, pp. 1-24) (Year: 2002) (Year: 2002).*

Abbas Vafai, "Antibody-binding sites on truncated forms of varicella-zoster virus gpl(gE) glycoprotein", Vaccine, vol. 12, No. 14 (1994), pp. 1265-1269.

Abstract of Slingluff et al., Journal for ImmunoTherapy of Cancer (Nov. 6, 2014), vol. 2, Suppl. 3, Abstract No. P60. 2 pgs.

Alving et al., "Liposomal adjuvants for human vaccines", Expert Opinion on Drug Delivery (2016), vol. 13, No. 6, pp. 807-816Alving et al., "Liposomal adjuvants for human vaccines", Expert Opinion on Drug Delivery (2016), vol. 13, No. 6, pp. 807-816.

Arbeter et al., "Live attenuated varicella vaccine: Immunization of healthy children with the OKA strain", The Journal of PEDIATRICS, vol. 100, No. 6 (1982), pp. 886-893.

Arvin et al., "Equivalent recognition of a varicella-zoster virus immediate early protein (IE62) and glycoprotein I by cytotoxic T lymphocytes of either CD4+ or CD8+ phenotype", J Immunol, vol. 146 (1991), pp. 257-264.

Arvin et al., "Memory Cytotoxic T Cell Responses to Viral Tegument and Regulatory Proteins Encoded by Open Reading Frames 4, 10, 29, and 62 of Varicella-Zoster Virus", Viral Immunology, vol. 15, No. 3 (2002), pp. 507-516.

Bautz, "OGEN: COVID-19 Vaccine Candidate Exhibits Protective Immunity in Mice . . . ", Zacks Small-Cap Research, Apr. 9, 2021 (Apr. 9, 2021) pp. 1-7.

Brichard, "Development of cancer vaccines with the MAGE-3 protein", Cancer Immunity (2005), vol. 5, Suppl. 1, p. 16BRICHARD, "Development of cancer vaccines with the MAGE-3 protein", Cancer Immunity (2005), vol. 5, Suppl. 1, p. 16.

Cibulski et al., "Novel ISCOMs from Quillaja brasiliensis saponins induce mucosal and systemic antibody production, T-cell responses and improved antigen uptake", Vaccine, vol. 34 (2016), pp. 1162-1171.

Coccia et al., "Cellular and molecular synergy in AS01-adjuvanted vaccines results in an early IFNγ response promoting vaccine immunogenicity", npj Vaccines, vol. 2 (2018), pp. 1-14.

Coplan et al., "Development of a Measure of the Burden of Pain Due to Herpes Zoster and Postherpetic Neuralgia for Prevention Trials: Adaptation of the Brief Pain Inventory", The Journal of Pain, vol. 5, No. 6 (2004), pp. 344-356.

Debrus et al., "Varicella-Zoster Virus Gene 63 Encodes an Immediate-Early Protein That is Abundantly Expressed during Latency", Journal of Virology, vol. 69, No. 5 (1995), pp. 3240-3245.

Didierlaurent et al., "Adjuvant system AS01: helping to overcome the challenges of modern vaccines", Expert Review of Vaccines (2017), vol. 16, No. 1, pp. 55-63.

Fleck et al., "Saponins from Quillaja saponaria and Quillaja brasiliensis: Particular Chemical Characteristics and Biological Activities", Molecules (2019), vol. 24, No. 171, pp. 1-29.

Fox, "Squalene Emulsions for Parenteral Vaccine and Drug Delivery", Molecules (2009), vol. 14, pp. 3286-3312.

Garcon et al., "Understanding Modern Vaccines: Perspectives in Vaccinology", Vaccine Adjuvants (2011), vol. 1, No. 1, pp. 89-113.

Gilden et al., "Neurologic Complications of the Reactivation of Varicella-Zoster Virus", Engl J Med., vol. 342, No. 9 (2000), pp. 635-645.

Harlow and Lane, "Antibodies: A Laboratory Manual", Cold Spring Harbor Laboratory (1988), p. 726, Biochemical Education, vol. 17, No. 4 (1989).

Haumont et al., "Purification, characterization and immunogenicity of recombinant varicella-zoster virus glycoprotein gE secreted by Chinese hamster ovary cells", Virus Research, vol. 40 (1996), pp. 199-204.

Huang et al., "Specific Lysis of Targets Expressing Varicella-Zoster Virus gpl or gplV by CD4+ Human T-Cell Clones", J. Virol., Vo. 66, No. 5 (1992), pp. 2664-2669.

Kensil et al., "QS-21: a water-soluble triterpene glycoside adjuvant", Expert Opinion on Investigational Drugs (1998), vol. 7, No. 9, pp. 1475-1482.

(56) References Cited

OTHER PUBLICATIONS

Marin et al., "Prevention of Varicella: Recommendations of the Advisory Committee on Immunization Practices (ACIP)", MMWR Recomm Rep., vol. 56, No. RR-4 (2007); pp. 1-40.
Patra et al., "Alga-Produced Malaria 'Transmission-Blocking Vaccine Candidate Pfs25 Formulated with a Human Use-Compatible Potent Adjuvant Induces High-Affinity Antibodies' That Block Plasmodium falciparum Infection of Mosquitoes", Infection and Immunity (2015), vol. 83, No. 5, pp. 1799-1808.
Pengfei Wang, "Natural and Synthetic Saponins as Vaccine Adjuvants", Vaccines, vol. 9, No. 222 (2021), pp. 1-18.
Sabella et al., "Immunization with the Immediate-Early Tegument Protein (Open Reading Frame 62) of Varicella-Zoster Virus Protects Guinea Pigs against Virus Challenge", Journal of Virology, vol. 67, No. 12 (1993), pp. 7673-7676.
Sawyer et al., "Detection of Varicella-Zoster Virus DNA in Air Samples from Hospital Rooms", J Infect Dis., vol. 169 (1994), pp. 91-94.
Senders et al., "1236. Safety and Immunogenicity of a 20-Valent Pneumococcal Conjugate Vaccine (PCV20) in Healthy Infants in the United States", Open Forum Infectious Diseases (Oct. 2020), vol. 7 (Suppl 1), p. S637.
Sharp et al., "Kinetics and Viral Protein Specificity of the Cytotoxic T Lymphocyte Response in Healthy Adults Immunized with Live Attenuated Varicella Vaccine", JID, vol. 165 (1992), pp. 852-858.
Slingluff et al., "A randomized pilot trial testing the safety and immunologic effects of a MAGE-A3 protein plus AS15 immunostimulant administered into muscle or into dermal/subcutaneous sites", Cancer Immunol Immunother (2016), vol. 65, pp. 25-36.
Toussi et al., "Immune Adjuvant Effect of Molecularly-defined Toll-Like Receptor Ligands", Vaccines (2014), vol. 2, pp. 323-353.
Wui et al., "Efficient induction of cell-mediated immunity to varicella-zoster virus glycoprotein E co-lyophilized with cationic liposome-based adjuvant in mice", Vaccine (2019), vol. 37, No. 15, pp. 2131-2141.
Adams et al., "Design and Synthesis of Potent Quillaja Saponin Vaccine Adjuvants", J Am Chem Soc. 1939(2010), vol. 132 (6), pp. 1-16.
Adams, "Synthesis of Saponin Immunoadjuvants", University of Illinois at Urbana-Champaign, Ph.D. Dissertation 2009 [retrieved on Jul. 18, 2018). Retrieved from the Internet: <URL: https://search.proquest.com/docview/304896057>. See Abstract, pp. 45-47.
Balsevich et al., "Analysis of bisdesmosidic saponins in *Saponaria vaccaria* L. by HPLC-PAD-MS: identification of new quillaic acid and gypsogenin 3-O-Trisaccharides." Phytochemical analysis, vol. 17, No. 6, pp. 414-423 (Oct. 18, 2006) (https://doi.org/10.1002/pca.943).
Carcaboso et al., Potent, long lasting systematic antibody levels and mixed Th1/Th2 immune response after nasal immunization with malaria antigen loaded PLGA microparticles, Vaccine (2004), vol. 22, (11-12), pp. 1423-1432.
Chea et al., "Synthesis and Preclinical Evaluation of QS-21 Variants Leading to Simplified Vaccine Adjuvants and Mechanistic Probes", J Am Chem Soc. vol. 134, No. 32 (2012), 26 pgs.
Evans et al., "QS-21 promotes an adjuvant effect allowing for reduced antigen dose during HIV-1 envelope subunit immunization in humans", Vaccine (2001), vol. 19, pp. 2080-2091.
Fernandez-Tejada et al., "Development of a minimal saponin vaccine adjuvant based on QS-21", Published in final edited form as: Nat Chem. vol. 6, No. 7 (2014), pp. 635-643.
Fernández-Tejada et al., "Development of Improved Vaccine Adjuvants Based on the Saponin Natural Product QS-21 through Chemical Synthesis", Accounts of Chemical Research (2016), vol. 49, pp. 1741-1756.
Fernández-Tejada et al., "Semisynthesis of Analogues of the Saponin Immunoadjuvant QS-21", Methods in Molecular Biology (2016), vol. 1494, pp. 45-71.
Fernández-Tejada et al., "Versatile Strategy for the Divergent Synthesis of Linear Oligosaccharide Domain Variants of Quillaja Saponin Vaccine Adjuvants", Chem Commun (2015), vol. 51 (73), pp. 13949-13952.
Fernandez-Tejada et al; "Design, synthesis, and immunologic evaluation of vaccine adjuvant conjugates based on QS-21 and tucaresol" Bioorganic & Medicinal Chemistry, vol. 22, No. 21 (2014), pp. 5917-5923.
Fernandez-Tejada et al; "Development of a Minimal Saponin Vaccine Adjuvant based on QS-21", Supplementary Information, Nature Chemistry, vol. 6 (2014), pp. S1-S135.
Gin et al., "Enhancing Immunogenicity of Cancer Vaccines: QS-21 as an Immune Adjuvant", Curr Drug ther. (2011), vol. 6 (3), pp. 207-212.
Guo et al., "Triterpenoid Saponins From Quillaja Saponaria" Phytochemistry, vol. 48, No. 1, pp. 175-180 (1998).
International Search Report, PCT/US2020/058859, Feb. 11, 2021, 1 pg.
Kashala et al., "Safety, tolerability and immunogenicity of new formulations of the Plasmodium falciparum malaria peptide vaccine SPf66 combined with the immunological adjuvant QS-21", Vaccine (2002), vol. 20, pp. 2263-2277.
Kensil et al., "Separation and characterization of saponins with adjuvant activity from Quillaja saponaria Molina cortex", Journal of Immunology (1991), vol. 146 (2), pp. 431-437.
Kensil, "Saponins as Vaccine Adjuvants", Critical Reviews in Therapeutic Drug Carrier Systems (1996), vol. 13 (1&2), pp. 1-55.
Kim et al., "Comparison of the effect of different immunological adjuvants on the antibody and T-cell response to Immunization with MUC1-KLH and GD3-KLH conjugate cancer vaccines", Vaccine (2000), vol. 18, pp. 597-603.
Livingston et al., "Cancer vaccines targeting carbohydrate antigens", Human Vaccines (May-Jun. 2006), vol. 2 (3), pp. 137-143.
Newman et al., "Saponin adjuvant induction of ovalbumin-specific CD8+ cytotoxic T lymphocyte responses", Journal of Immunology (1992), vol. 148, pp. 2357-2362.
Ragupathi et al., "Natural and synthetic saponin adjuvant QS-21 for vaccines against cancer", Expert Rev Vaccines (2011), vol. 10 (4), pp. 463-470.
Ragupathi et al., "Preclinical Evaluation of the Synthetic Adjuvant SQS-21 and its Constituent Isomeric Saponins", Vaccine (2010), vol. 28 (26), pp. 4260-4267.
Sasaki et al., "Induction of systemic and mucosal immune responses to human immunodeficiency virus type 1 by a DNA vaccine formulated with QS-21 saponin adjuvant via intramuscular and intranasal routes", Journal of Virology (Jun. 1998), vol. 72 (6), pp. 4931-4939.
Soltysik et al., "Structure/function studies of QS-21 adjuvant: assessment of triterpene aldehyde and glucuronic acid roles in adjuvant function", Vaccine (1995), vol. 13 (15), pp. 1403-1410.
Van Setten et al., "Glycosyl compositions and structural characteristics of the potential immunoadjuvant active saponins in the Quillaja saponaria Mollina extract Quil A", Rapid Communications in Mass Spectrometry (1995), vol. 9, pp. 660-666.
Walkowicz et al., "Quillaja saponin variants with central glycosidic linkage modifications exhibit distinct conformations and adjuvant activities", Chem. Sci. (2016), vol. 7, pp. 2371-2380.
Wuts et al.; "Chapter 2: Protection for the Hydroxyl Group, Including 1,2- and 1,3-Diols", Greene's Protective Groups in Organic Synthesis, 4th Ed. (Dec. 31, 2006), 351 pgs.

* cited by examiner

FIGURE 1

| | | | | | | |
|---|---|---|---|---|---|---|
| MGTVNKPVVG | VLMGFGIITG | TLRITNPVRA | SVLRYDDFHI | DEDKLDTNSV | YEPYYHSDHA | 60 |
| ESSWVNRGES | SRKAYDHNSP | YIWPRNDYDG | FLENAHEHHG | VYNQGRGIDS | GERLMQPTQM | 120 |
| SAQEDLGDDT | GIHVIPTLNG | DDRHKIVNVD | QRQYGDVFKG | DLNPKPQGQR | LIEVSVEENH | 180 |
| PFTLRAPIQR | IYGVRYTETW | SFLPSLTCTG | DAAPAIQHIC | LKHTTCFQDV | VVDVDCAENT | 240 |
| KEDQLAEISY | RFQGKKEADQ | PWIVVNTSTL | FDELELDPPE | IEPGVLKVLR | TEKQYLGVYI | 300 |
| WNMRGSDGTS | TYATFLVTWK | GDEKTRNPTP | AVTPQPRGAE | FHMWNYHSHV | FSVGDTFSLA | 360 |
| MHLQYKIHEA | PFDLLLEWLY | VPIDPTCQPM | RLYSTCLYHP | NAPQCLSHMN | SGCTFTSPHL | 420 |
| AQRVASTVYQ | NCEHADNYTA | YCLGISHMEP | SFGLILHDGG | TTLKFVDTPE | SLSGLYVFVV | 480 |
| YFNGHVEAVA | YTVVSTVDHF | VNAIEERGFP | PTAGQPPATT | KPKEITPVNP | GTSPLIRYAA | 540 |
| WTGGLA | | | | | | 546 |

FIGURE 2

| | | | | | | |
|---|---|---|---|---|---|---|
| MGTVNKPVVG | VLMGFGIITG | TLRITNPVRA | SVLRYDDFHT | DEDKLDTNSV | YEPYYHSDHA | 60 |
| ESSWVNRGES | SRKAYDHNSP | YIWPRNDYDG | FLENAHEHHG | VYNQGRGIDS | GERLMQPTQM | 120 |
| SAQEDLGDDT | GIHVIPTLNG | DDRHKIVNVD | QRQYGDVFKG | DLNPKPQGQR | LIEVSVEENH | 180 |
| PFTLRAPIQR | IYGVRYTETW | SFLPSLTCTG | DAAPAIQHIC | LKHTTCFQDV | VVDVDCAENT | 240 |
| KEDQLAEISY | RFQGKKEADQ | PWIVVNTSTL | FDELELDPPE | IEPGVLKVLR | TEKQYLGVYI | 300 |
| WNMRGSDGTS | TYATFLVTWK | GDEKTRNPTP | AVTPQPRGAE | FHMWNYHSHV | FSVGDTFSLA | 360 |
| MHLQYKIHEA | PFDLLLEWLY | VPIDPTCQPM | RLYSTCLYHP | NAPQCLSHMN | SGCTFTSPHL | 420 |
| AQRVASTVYQ | NCEHADNYTA | YCLGISHMEP | SFGLILHDGG | TTLKFVDTPE | SLSGLYVFVV | 480 |
| YFNGHVEAVA | YTVVSTVDHF | VNAIEERGFP | PTAGQPPATT | KPKEITPVNP | GTSPLLRYAA | 540 |
| WTGGLA | | | | | | 546 |

FIGURE 3

```
MGTVNKPVVG  VLMGFGIITG  TLRITNPVRA  SVLRYDDFHT  DEDKLDTNSV  YEPYYHSDHA   60
ESSWVNRGES  SRKAYDHNSP  YIWPRNDYDG  FLENAHEHHG  VYNQGRGIDS  GERLMQPTQM  120
SAQEDLGDDT  GIHVIPTLNG  DDRHKIVNVD  QRQYGDVFKG  DLNPKPQGQR  LIEVSVEENH  180
PFTLRAPIQR  IYGVRYTETW  SFLPSLTCTG  DAAPAIQHIC  LKHTTCFQDV  VVDVDCAENT  240
KEDQLAEISY  RFQGKKEADQ  PWIVVNTSTL  FDELELDPPE  IEPGVLKVLR  TEKQYLGVYI  300
WNMRGSDGTS  TYATFLVTWK  GDEKTRNPTP  AVTPQPRGAE  FHMWNYHSHV  FSVGDTFSLA  360
MHLQYKIHEA  PFDLLLEWLY  VPIDPTCQPM  RLYSTCLYHP  NAPQCLSHMN  SGCTFTSPHL  420
AQRVASTVYQ  NCEHADNYTA  YCLGISHMEP  SFGLILHDGG  TTLKFVDTPE  SLSGLYVFVV  480
YFNGHVEAVA  YTVVSTVDHF  VNAIEERGFP  PTAGQPPATT  KPKEITPVNP  GTSPLLRYAA  540
WTGGLAAVVL  LCLVIFLICT  AKRMRVKAYR  VDKSPYNQSM  YYAGLPVDDF  EDSESTDTEE  600
EFGNAIGGSH  GGSSYTVYID  KTR                                            623
```

FIGURE 4

| | | | | | | |
|---|---|---|---|---|---|---|
| MGTVNKPVVG | VLMGFGIITG | TLRITNPVRA | SVLRYDDFHT | DEDKLDTNSV | YEPYYHSDHA | 60 |
| ESSWVNRGES | SRKAYDHNSP | YIWPRNDYDG | FLENAHEHHG | VYNQGRGIDS | GERLMQPTQM | 120 |
| SAQEDLGDDT | GIHVIPTLNG | DDRHKIVNVD | QRQYGDVFKG | DLNPKPQGQR | LIEVSVEENH | 180 |
| PFTLRAPIQR | IYGVRYTETW | SFLPSLTCTG | DAAPAIQHIC | LKHTTCFQDV | VVDVDCAENT | 240 |
| KEDQLAEISY | RFQGKKEADQ | PWIVVNTSTL | FDELELDPPE | IEPGVLKVLR | TEKQYLGVYI | 300 |
| WNMRGSDGTS | TYATFLVTWK | GDEKTRNPTP | AVTPQPRGAE | FHMWNYHSHV | FSVGDTFSLA | 360 |
| MHLQYKIHEA | PFDLLLEWLY | VPIDPTCQPM | RLYSTCLYHP | NAPQCLSHMN | SGCTFTSPHL | 420 |
| AQRVASTVYQ | NCEHADNYTA | YCLGISHMEP | SFGLILHDGG | TTLKFVDTPE | SLSGLYVFVV | 480 |
| YFNGHVEAVA | YTVVSTVDHF | VNAIEERGFP | PTAGQPPATT | KPKEITPVNP | GTSPLIRYAA | 540 |
| WTGGLAAVVL | LCLVIFLICT | AKRMRVKAYR | VDKSPYNQSM | YYAGLPVDDF | EDSESTDTEE | 600 |
| EFGNAIGGSH | GGSSYTVYID | KTR | | | | 623 |

FIGURE 5

| | | | | | | |
|---|---|---|---|---|---|---|
| MSPCGYYSKW | RNRDRPEYRR | NLRFRRFFSS | IHPNAAAGSG | FNGPGVFITS | VTGVWLCFLC | 60 |
| IFSMFVTAVV | SVSPSSFYES | LQVEPTQSED | ITRSAHLGDG | DEIREAIHKS | QDAETKPTFY | 120 |
| VCPPPTGSTI | VRLEPPRTCP | DYHLGKNFTE | GIAVVYKENI | AAYKFKATVY | YKDVIVSTAW | 180 |
| AGSSYTQITN | RYADRVPIPV | SEITDTIDKF | GKCSSKATYV | RNNHKVEAFN | EDKNPQDMPL | 240 |
| IASKYNSVGS | KAWHTTNDTY | MVAGTPGTYR | TGTSVNCIIE | EVEARSIFPY | DSFGLSTGDI | 300 |
| IYMSPFFGLR | DGAYREHSNY | AMDRFHQFEG | YRQRDLDTRA | LLEPAARNFL | VTPHLTVGWN | 360 |
| WKPKRTEVCS | LVKWREVEDV | VRDEYAHNFR | FTMKTLSTTF | ISETNEFNLN | QIHLSQCVKE | 420 |
| EARAIINRIY | TTRYNSSHVR | TGDIQTYLAR | GGFVVVFQPL | LSNSLARLYL | QELVRENTNH | 480 |
| SPQKHPTRNT | RSRRSVPVEL | RANRTITTTS | SVEFAMLQFT | YDHIQEHVNE | MLARISSSWC | 540 |
| QLQNRERALW | SGLFPINPSA | LASTILDQRV | KARILGDVIS | VSNCPELGSD | TRIILQNSMR | 600 |
| VSGSTTRCYS | RPLISIVSLN | GSGTVEGQLG | TDNELIMSRD | LLEPCVANHK | RYFLFGHHYV | 660 |
| YYEDYRYVRE | IAVHDVGMIS | TYVDLNLTLL | KDREFMPLQV | YTRDELRDTG | LLDYSEIQRR | 720 |
| NQMHSLRFYD | IDKVVQYDSG | TAIMQGMAQF | FQGLGTAGQA | VGHVVLGATG | ALLSTVHGFT | 780 |
| TFLSNPFGAL | AVGLLVLAGL | VAAFFAYRYV | LKLKTSPMKA | LYPLTTKGLK | QLPEGMDPFA | 840 |
| EKPNATDTPI | EEIGDSQNTE | PSVNSGFDPD | KFREAQEMIK | YMTLVSAAER | QESKARKKNK | 900 |
| TSALLTSRLT | GLALRNRRGY | SRVRTENVTG | V | | | 931 |

FIGURE 6

| | | | | | | |
|---|---|---|---|---|---|---|
| MFALVLAVVI | LPLWTTANKS | YVTPTPATRS | IGHMSALLRE | YSDRNMSLKL | EAFYPTGFDE | 60 |
| ELIKSLHWGN | DRKHVFLVIV | KVNPTTHEGD | VGLVIFPKYL | LSPYHFKAEH | RAPFPAGRFG | 120 |
| FLSHPVTPDV | SFFDSSFAPY | LTTQHLVAFT | TFPPNPLVWH | LERAETAATA | ERPFGVSLLP | 180 |
| ARPTVPKNTI | LEHKAHFATW | DALARHTFFS | AEAIITNSTL | RIHVPLFGSV | WPIRYWATGS | 240 |
| VLLTSDSGRV | EVNIGVGFMS | SLISLSSGLP | IELIVVPHTV | KLNAVTSDTT | WFQLNPPGPD | 300 |
| PGPSYRVYLL | GRGLDMNFSK | HATVDICAYP | EESLDYRYHL | SMAHTEALRM | TTKADQHDIN | 360 |
| EESYYHIAAR | IATSIFALSE | MGRTTEYFLL | DEIVDVQYQL | KFLNYILMRI | GAGAHPNTIS | 420 |
| GTSDLIFADP | SQLHDELSLL | FGQVKPANVD | YFISYDEARD | QLKTAYALSR | GQDHVNALSL | 480 |
| ARRVIMSIYK | GLLVKQNLNA | TERQALFFAS | MILLNFREGL | ENSSRVLDGR | TTLLLMTSMC | 540 |
| TAAHATQAAL | NIQEGLAYLN | PSKHMFTIPN | VYSPCMGSLR | TDLTEEIHVM | NLLSAIPTRP | 600 |
| GLNEVLHTQL | DESEIFDAAF | KTMMIFTTWT | AKDLHILHTH | VPEVFTCQDA | AARNGEYVLI | 660 |
| LPAVQGHSYV | ITRNKPQRGL | VYSLADVDVY | NPISVVYLSK | DTCVSEHGVI | ETVALPHPDN | 720 |
| LKECLYCGSV | FLRYLTTGAI | MDIIIIDSKD | TERQLAAMGN | STIPPFNPDM | HGDDSKAVLL | 780 |
| FPNGTVVTLL | GFERRQAIRM | SGQYLGASLG | GAFLAVVGFG | IIGWMLCGNS | RLREYNKIPL | 840 |
| T | | | | | | 841 |

FIGURE 7

| | | | | | | |
|---|---|---|---|---|---|---|
| MFLIQCLISA | VIFYIQVTNA | LIFKGDHVSL | QVNSSLTSIL | IPMQNDNYTE | IKGQLVFIGE | 60 |
| QLPTGTNYSG | TLELLYADTV | AFCFRSVQVI | RYDGCPRIRT | SAFISCRYKH | SWHYGNSTDR | 120 |
| ISTEPDAGVM | LKITKPGIND | AGVYVLLVRL | DHSRSTDGFI | LGVNVYTAGS | HHNIHGVIYT | 180 |
| SPSLQNGYST | RALFQQARLC | DLPATPKGSG | TSLFQHMLDL | RAGKSLEDNP | WLHEDVVTTE | 240 |
| TKSVVKEGIE | NHVYPTDMST | LPEKSLNDPP | ENLLIIIPIV | ASVMILTAMV | IVIVISVKRR | 300 |
| RIKKHPIYRP | NTKTRRGIQN | ATPESDVMLE | AAIAQLATIR | EESPPHSVVN | PFVK | 354 |

FIGURE 8

| | | | | | | |
|---|---|---|---|---|---|---|
| MSKKTFPSFK | FRGGCFNLLF | KGSVDVSIKT | RMKRIQINLI | LTIACIQLST | ESQPTPVSIT | 60 |
| ELYTSAATRK | PDPAVAPTSA | ASRKPDPAVA | PTSAASRKPD | PAVAPTSAAS | RKPDPAVAPT | 120 |
| SAATRKPDPA | VAPTSAASRK | PDPAVAPTSA | ATRKPDPAVA | PTSAASRKPD | PAANTQHSQP | 180 |
| PFLYENIQCV | HGGIQSIPYF | HTFIMPCYMR | LTTGQQAAFK | QQQKTYEQYS | LDPEGSNITR | 240 |
| WKSLIRPDLH | IEVWFTRHLI | DPHRQLGNAL | IRMPDLPVML | YSNSADLNLI | NNPEIFTHAK | 300 |
| ENYVIPDVKT | TSDFSVTILS | MDATTEGTYI | WRVVNTKTKN | VISEHSITVT | TYYRPNITVV | 360 |
| GDPVLTGQTY | AAYCNVSKYY | PPHSVRVRWT | SRFGNIGKNF | ITDAIQEYAN | GLFSYVSAVR | 420 |
| IPQQKQMDYP | PPAIQCNVLW | IRDGVSNMKY | SAVVTPDVYP | FPNVSIGIID | GHIVCTAKCV | 480 |
| PRGVVHFVWW | VNDSPINHEN | SEITGVCDQN | KRFVNMQSSC | PTSELDGPIT | YSCHLDGYPK | 540 |
| KFPPFSAVYT | YDASTYATTF | SVVAVIIGVI | SILGTLGLIA | VIATLCIRCC | S | 591 |

FIGURE 9

| | | | | | | |
|---|---|---|---|---|---|---|
| MGVKVLFALI | CIAVAEASVL | RYDDFHIDED | KLDTNSVYEP | YYHSDHAESS | WVNRGESSRK | 60 |
| AYDHNSPYIW | PRNDYDGFLE | NAHEHHGVYN | QGRGIDSGER | LMQPTQMSAQ | EDLGDDTGIH | 120 |
| VIPTLNGDDR | HKIVNVDQRQ | YGDVFKGDLN | PKPQGQRLIE | VSVEENHPFT | LRAPIQRIYG | 180 |
| VRYTETWSFL | PSLTCTGDAA | PAIQHICLKH | TTCFQDVVVD | VDCAENTKED | QLAEISYRFQ | 240 |
| GKKEADQPWI | VVNTSTLFDE | LELDPPEIEP | GVLKVLRTEK | QYLGVYIWNM | RGSDGTSTYA | 300 |
| TFLVTWKGDE | KTRNPTPAVT | PQPRGAEFHM | WNYHSHVFSV | GDTFSLAMHL | QYKIHEAPFD | 360 |
| LLLEWLYVPI | DPTCQPMRLY | STCLYHPNAP | QCLSHMNSGC | TFTSPHLAQR | VASTVYQNCE | 420 |
| HADNYTAYCL | GISHMEPSFG | LILHDGGTTL | KFVDTPESLS | GLYVFVVYFN | GHVEAVAYTV | 480 |
| VSTVDHFVNA | IEERGFPPTA | GQPPATTKPK | EITPVNPGTS | PLIRYAAWTG | GLA | 533 |

SEQUENCE LISTING

```
<160> NUMBER OF SEQ ID NOS: 9

<210> SEQ ID NO 1
<211> LENGTH: 546
<212> TYPE: PRT
<213> ORGANISM: Varicella zoster

<400> SEQUENCE: 1

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
```

-continued

```
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540
```

-continued

```
Leu Ala
545


<210> SEQ ID NO 2
<211> LENGTH: 546
<212> TYPE: PRT
<213> ORGANISM: Varicella zoster

<400> SEQUENCE: 2

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
```

```
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala
545


<210> SEQ ID NO 3
<211> LENGTH: 623
<212> TYPE: PRT
<213> ORGANISM: Varicella zoster

<400> SEQUENCE: 3

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175
```

-continued

```
Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
```

```
        595                 600                 605

Ser His Gly Gly Ser Ser Tyr Thr Val Tyr Ile Asp Lys Thr Arg
    610                 615                 620


<210> SEQ ID NO 4
<211> LENGTH: 623
<212> TYPE: PRT
<213> ORGANISM: Varicella zoster

<400> SEQUENCE: 4

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350
```

-continued

```
Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620


<210> SEQ ID NO 5
<211> LENGTH: 931
<212> TYPE: PRT
<213> ORGANISM: Varicella zoster

<400> SEQUENCE: 5

Met Ser Pro Cys Gly Tyr Tyr Ser Lys Trp Arg Asn Arg Asp Arg Pro
1               5                   10                  15

Glu Tyr Arg Arg Asn Leu Arg Phe Arg Arg Phe Phe Ser Ser Ile His
            20                  25                  30

Pro Asn Ala Ala Ala Gly Ser Gly Phe Asn Gly Pro Gly Val Phe Ile
        35                  40                  45

Thr Ser Val Thr Gly Val Trp Leu Cys Phe Leu Cys Ile Phe Ser Met
    50                  55                  60

Phe Val Thr Ala Val Val Ser Val Ser Pro Ser Ser Phe Tyr Glu Ser
65                  70                  75                  80

Leu Gln Val Glu Pro Thr Gln Ser Glu Asp Ile Thr Arg Ser Ala His
                85                  90                  95

Leu Gly Asp Gly Asp Glu Ile Arg Glu Ala Ile His Lys Ser Gln Asp
            100                 105                 110
```

-continued

```
Ala Glu Thr Lys Pro Thr Phe Tyr Val Cys Pro Pro Pro Thr Gly Ser
        115                 120                 125

Thr Ile Val Arg Leu Glu Pro Pro Arg Thr Cys Pro Asp Tyr His Leu
    130                 135                 140

Gly Lys Asn Phe Thr Glu Gly Ile Ala Val Val Tyr Lys Glu Asn Ile
145                 150                 155                 160

Ala Ala Tyr Lys Phe Lys Ala Thr Val Tyr Tyr Lys Asp Val Ile Val
                165                 170                 175

Ser Thr Ala Trp Ala Gly Ser Ser Tyr Thr Gln Ile Thr Asn Arg Tyr
            180                 185                 190

Ala Asp Arg Val Pro Ile Pro Val Ser Glu Ile Thr Asp Thr Ile Asp
        195                 200                 205

Lys Phe Gly Lys Cys Ser Ser Lys Ala Thr Tyr Val Arg Asn Asn His
    210                 215                 220

Lys Val Glu Ala Phe Asn Glu Asp Lys Asn Pro Gln Asp Met Pro Leu
225                 230                 235                 240

Ile Ala Ser Lys Tyr Asn Ser Val Gly Ser Lys Ala Trp His Thr Thr
                245                 250                 255

Asn Asp Thr Tyr Met Val Ala Gly Thr Pro Gly Thr Tyr Arg Thr Gly
            260                 265                 270

Thr Ser Val Asn Cys Ile Ile Glu Glu Val Glu Ala Arg Ser Ile Phe
        275                 280                 285

Pro Tyr Asp Ser Phe Gly Leu Ser Thr Gly Asp Ile Ile Tyr Met Ser
    290                 295                 300

Pro Phe Phe Gly Leu Arg Asp Gly Ala Tyr Arg Glu His Ser Asn Tyr
305                 310                 315                 320

Ala Met Asp Arg Phe His Gln Phe Glu Gly Tyr Arg Gln Arg Asp Leu
                325                 330                 335

Asp Thr Arg Ala Leu Leu Glu Pro Ala Ala Arg Asn Phe Leu Val Thr
            340                 345                 350

Pro His Leu Thr Val Gly Trp Asn Trp Lys Pro Lys Arg Thr Glu Val
        355                 360                 365

Cys Ser Leu Val Lys Trp Arg Glu Val Glu Asp Val Val Arg Asp Glu
    370                 375                 380

Tyr Ala His Asn Phe Arg Phe Thr Met Lys Thr Leu Ser Thr Thr Phe
385                 390                 395                 400

Ile Ser Glu Thr Asn Glu Phe Asn Leu Asn Gln Ile His Leu Ser Gln
                405                 410                 415

Cys Val Lys Glu Glu Ala Arg Ala Ile Ile Asn Arg Ile Tyr Thr Thr
            420                 425                 430

Arg Tyr Asn Ser Ser His Val Arg Thr Gly Asp Ile Gln Thr Tyr Leu
        435                 440                 445

Ala Arg Gly Gly Phe Val Val Val Phe Gln Pro Leu Leu Ser Asn Ser
    450                 455                 460

Leu Ala Arg Leu Tyr Leu Gln Glu Leu Val Arg Glu Asn Thr Asn His
465                 470                 475                 480

Ser Pro Gln Lys His Pro Thr Arg Asn Thr Arg Ser Arg Arg Ser Val
                485                 490                 495

Pro Val Glu Leu Arg Ala Asn Arg Thr Ile Thr Thr Thr Ser Ser Val
            500                 505                 510

Glu Phe Ala Met Leu Gln Phe Thr Tyr Asp His Ile Gln Glu His Val
        515                 520                 525
```

-continued

```
Asn Glu Met Leu Ala Arg Ile Ser Ser Ser Trp Cys Gln Leu Gln Asn
    530                 535                 540

Arg Glu Arg Ala Leu Trp Ser Gly Leu Phe Pro Ile Asn Pro Ser Ala
545                 550                 555                 560

Leu Ala Ser Thr Ile Leu Asp Gln Arg Val Lys Ala Arg Ile Leu Gly
                565                 570                 575

Asp Val Ile Ser Val Ser Asn Cys Pro Glu Leu Gly Ser Asp Thr Arg
            580                 585                 590

Ile Ile Leu Gln Asn Ser Met Arg Val Ser Gly Ser Thr Thr Arg Cys
        595                 600                 605

Tyr Ser Arg Pro Leu Ile Ser Ile Val Ser Leu Asn Gly Ser Gly Thr
    610                 615                 620

Val Glu Gly Gln Leu Gly Thr Asp Asn Glu Leu Ile Met Ser Arg Asp
625                 630                 635                 640

Leu Leu Glu Pro Cys Val Ala Asn His Lys Arg Tyr Phe Leu Phe Gly
                645                 650                 655

His His Tyr Val Tyr Tyr Glu Asp Tyr Arg Tyr Val Arg Glu Ile Ala
            660                 665                 670

Val His Asp Val Gly Met Ile Ser Thr Tyr Val Asp Leu Asn Leu Thr
        675                 680                 685

Leu Leu Lys Asp Arg Glu Phe Met Pro Leu Gln Val Tyr Thr Arg Asp
    690                 695                 700

Glu Leu Arg Asp Thr Gly Leu Leu Asp Tyr Ser Glu Ile Gln Arg Arg
705                 710                 715                 720

Asn Gln Met His Ser Leu Arg Phe Tyr Asp Ile Asp Lys Val Val Gln
                725                 730                 735

Tyr Asp Ser Gly Thr Ala Ile Met Gln Gly Met Ala Gln Phe Phe Gln
            740                 745                 750

Gly Leu Gly Thr Ala Gly Gln Ala Val Gly His Val Val Leu Gly Ala
        755                 760                 765

Thr Gly Ala Leu Leu Ser Thr Val His Gly Phe Thr Thr Phe Leu Ser
    770                 775                 780

Asn Pro Phe Gly Ala Leu Ala Val Gly Leu Leu Val Leu Ala Gly Leu
785                 790                 795                 800

Val Ala Ala Phe Phe Ala Tyr Arg Tyr Val Leu Lys Leu Lys Thr Ser
                805                 810                 815

Pro Met Lys Ala Leu Tyr Pro Leu Thr Thr Lys Gly Leu Lys Gln Leu
            820                 825                 830

Pro Glu Gly Met Asp Pro Phe Ala Glu Lys Pro Asn Ala Thr Asp Thr
        835                 840                 845

Pro Ile Glu Glu Ile Gly Asp Ser Gln Asn Thr Glu Pro Ser Val Asn
    850                 855                 860

Ser Gly Phe Asp Pro Asp Lys Phe Arg Glu Ala Gln Glu Met Ile Lys
865                 870                 875                 880

Tyr Met Thr Leu Val Ser Ala Ala Glu Arg Gln Glu Ser Lys Ala Arg
                885                 890                 895

Lys Lys Asn Lys Thr Ser Ala Leu Leu Thr Ser Arg Leu Thr Gly Leu
            900                 905                 910

Ala Leu Arg Asn Arg Arg Gly Tyr Ser Arg Val Arg Thr Glu Asn Val
        915                 920                 925

Thr Gly Val
    930
```

-continued

<210> SEQ ID NO 6
<211> LENGTH: 841
<212> TYPE: PRT
<213> ORGANISM: Varicella zoster

<400> SEQUENCE: 6

Met Phe Ala Leu Val Leu Ala Val Val Ile Leu Pro Leu Trp Thr Thr
1 5 10 15

Ala Asn Lys Ser Tyr Val Thr Pro Thr Pro Ala Thr Arg Ser Ile Gly
20 25 30

His Met Ser Ala Leu Leu Arg Glu Tyr Ser Asp Arg Asn Met Ser Leu
35 40 45

Lys Leu Glu Ala Phe Tyr Pro Thr Gly Phe Asp Glu Glu Leu Ile Lys
50 55 60

Ser Leu His Trp Gly Asn Asp Arg Lys His Val Phe Leu Val Ile Val
65 70 75 80

Lys Val Asn Pro Thr Thr His Glu Gly Asp Val Gly Leu Val Ile Phe
85 90 95

Pro Lys Tyr Leu Leu Ser Pro Tyr His Phe Lys Ala Glu His Arg Ala
100 105 110

Pro Phe Pro Ala Gly Arg Phe Gly Phe Leu Ser His Pro Val Thr Pro
115 120 125

Asp Val Ser Phe Phe Asp Ser Ser Phe Ala Pro Tyr Leu Thr Thr Gln
130 135 140

His Leu Val Ala Phe Thr Thr Phe Pro Pro Asn Pro Leu Val Trp His
145 150 155 160

Leu Glu Arg Ala Glu Thr Ala Ala Thr Ala Glu Arg Pro Phe Gly Val
165 170 175

Ser Leu Leu Pro Ala Arg Pro Thr Val Pro Lys Asn Thr Ile Leu Glu
180 185 190

His Lys Ala His Phe Ala Thr Trp Asp Ala Leu Ala Arg His Thr Phe
195 200 205

Phe Ser Ala Glu Ala Ile Ile Thr Asn Ser Thr Leu Arg Ile His Val
210 215 220

Pro Leu Phe Gly Ser Val Trp Pro Ile Arg Tyr Trp Ala Thr Gly Ser
225 230 235 240

Val Leu Leu Thr Ser Asp Ser Gly Arg Val Glu Val Asn Ile Gly Val
245 250 255

Gly Phe Met Ser Ser Leu Ile Ser Leu Ser Ser Gly Leu Pro Ile Glu
260 265 270

Leu Ile Val Val Pro His Thr Val Lys Leu Asn Ala Val Thr Ser Asp
275 280 285

Thr Thr Trp Phe Gln Leu Asn Pro Pro Gly Pro Asp Pro Gly Pro Ser
290 295 300

Tyr Arg Val Tyr Leu Leu Gly Arg Gly Leu Asp Met Asn Phe Ser Lys
305 310 315 320

His Ala Thr Val Asp Ile Cys Ala Tyr Pro Glu Glu Ser Leu Asp Tyr
325 330 335

Arg Tyr His Leu Ser Met Ala His Thr Glu Ala Leu Arg Met Thr Thr
340 345 350

Lys Ala Asp Gln His Asp Ile Asn Glu Glu Ser Tyr Tyr His Ile Ala
355 360 365

Ala Arg Ile Ala Thr Ser Ile Phe Ala Leu Ser Glu Met Gly Arg Thr
370 375 380

-continued

```
Thr Glu Tyr Phe Leu Leu Asp Glu Ile Val Asp Val Gln Tyr Gln Leu
385                 390                 395                 400

Lys Phe Leu Asn Tyr Ile Leu Met Arg Ile Gly Ala Gly Ala His Pro
                405                 410                 415

Asn Thr Ile Ser Gly Thr Ser Asp Leu Ile Phe Ala Asp Pro Ser Gln
            420                 425                 430

Leu His Asp Glu Leu Ser Leu Leu Phe Gly Gln Val Lys Pro Ala Asn
        435                 440                 445

Val Asp Tyr Phe Ile Ser Tyr Asp Glu Ala Arg Asp Gln Leu Lys Thr
    450                 455                 460

Ala Tyr Ala Leu Ser Arg Gly Gln Asp His Val Asn Ala Leu Ser Leu
465                 470                 475                 480

Ala Arg Arg Val Ile Met Ser Ile Tyr Lys Gly Leu Leu Val Lys Gln
                485                 490                 495

Asn Leu Asn Ala Thr Glu Arg Gln Ala Leu Phe Phe Ala Ser Met Ile
            500                 505                 510

Leu Leu Asn Phe Arg Glu Gly Leu Glu Asn Ser Ser Arg Val Leu Asp
        515                 520                 525

Gly Arg Thr Thr Leu Leu Leu Met Thr Ser Met Cys Thr Ala Ala His
    530                 535                 540

Ala Thr Gln Ala Ala Leu Asn Ile Gln Glu Gly Leu Ala Tyr Leu Asn
545                 550                 555                 560

Pro Ser Lys His Met Phe Thr Ile Pro Asn Val Tyr Ser Pro Cys Met
                565                 570                 575

Gly Ser Leu Arg Thr Asp Leu Thr Glu Glu Ile His Val Met Asn Leu
            580                 585                 590

Leu Ser Ala Ile Pro Thr Arg Pro Gly Leu Asn Glu Val Leu His Thr
        595                 600                 605

Gln Leu Asp Glu Ser Glu Ile Phe Asp Ala Ala Phe Lys Thr Met Met
    610                 615                 620

Ile Phe Thr Thr Trp Thr Ala Lys Asp Leu His Ile Leu His Thr His
625                 630                 635                 640

Val Pro Glu Val Phe Thr Cys Gln Asp Ala Ala Ala Arg Asn Gly Glu
                645                 650                 655

Tyr Val Leu Ile Leu Pro Ala Val Gln Gly His Ser Tyr Val Ile Thr
            660                 665                 670

Arg Asn Lys Pro Gln Arg Gly Leu Val Tyr Ser Leu Ala Asp Val Asp
        675                 680                 685

Val Tyr Asn Pro Ile Ser Val Val Tyr Leu Ser Lys Asp Thr Cys Val
    690                 695                 700

Ser Glu His Gly Val Ile Glu Thr Val Ala Leu Pro His Pro Asp Asn
705                 710                 715                 720

Leu Lys Glu Cys Leu Tyr Cys Gly Ser Val Phe Leu Arg Tyr Leu Thr
                725                 730                 735

Thr Gly Ala Ile Met Asp Ile Ile Ile Ile Asp Ser Lys Asp Thr Glu
            740                 745                 750

Arg Gln Leu Ala Ala Met Gly Asn Ser Thr Ile Pro Pro Phe Asn Pro
        755                 760                 765

Asp Met His Gly Asp Asp Ser Lys Ala Val Leu Leu Phe Pro Asn Gly
    770                 775                 780

Thr Val Val Thr Leu Leu Gly Phe Glu Arg Arg Gln Ala Ile Arg Met
785                 790                 795                 800

Ser Gly Gln Tyr Leu Gly Ala Ser Leu Gly Gly Ala Phe Leu Ala Val
```

```
                805                 810                 815

Val Gly Phe Gly Ile Ile Gly Trp Met Leu Cys Gly Asn Ser Arg Leu
            820                 825                 830

Arg Glu Tyr Asn Lys Ile Pro Leu Thr
        835                 840


<210> SEQ ID NO 7
<211> LENGTH: 354
<212> TYPE: PRT
<213> ORGANISM: Varicella zoster

<400> SEQUENCE: 7

Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
            20                  25                  30

Asn Ser Ser Leu Thr Ser Ile Leu Ile Pro Met Gln Asn Asp Asn Tyr
        35                  40                  45

Thr Glu Ile Lys Gly Gln Leu Val Phe Ile Gly Glu Gln Leu Pro Thr
    50                  55                  60

Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
                85                  90                  95

Arg Ile Arg Thr Ser Ala Phe Ile Ser Cys Arg Tyr Lys His Ser Trp
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175

Val Ile Tyr Thr Ser Pro Ser Leu Gln Asn Gly Tyr Ser Thr Arg Ala
            180                 185                 190

Leu Phe Gln Gln Ala Arg Leu Cys Asp Leu Pro Ala Thr Pro Lys Gly
        195                 200                 205

Ser Gly Thr Ser Leu Phe Gln His Met Leu Asp Leu Arg Ala Gly Lys
    210                 215                 220

Ser Leu Glu Asp Asn Pro Trp Leu His Glu Asp Val Val Thr Thr Glu
225                 230                 235                 240

Thr Lys Ser Val Val Lys Glu Gly Ile Glu Asn His Val Tyr Pro Thr
                245                 250                 255

Asp Met Ser Thr Leu Pro Glu Lys Ser Leu Asn Asp Pro Pro Glu Asn
            260                 265                 270

Leu Leu Ile Ile Ile Pro Ile Val Ala Ser Val Met Ile Leu Thr Ala
        275                 280                 285

Met Val Ile Val Ile Val Ile Ser Val Lys Arg Arg Arg Ile Lys Lys
    290                 295                 300

His Pro Ile Tyr Arg Pro Asn Thr Lys Thr Arg Arg Gly Ile Gln Asn
305                 310                 315                 320

Ala Thr Pro Glu Ser Asp Val Met Leu Glu Ala Ala Ile Ala Gln Leu
                325                 330                 335
```

-continued

Ala Thr Ile Arg Glu Glu Ser Pro Pro His Ser Val Val Asn Pro Phe
340 345 350

Val Lys

<210> SEQ ID NO 8
<211> LENGTH: 591
<212> TYPE: PRT
<213> ORGANISM: Varicella zoster

<400> SEQUENCE: 8

Met Ser Lys Lys Thr Phe Pro Ser Phe Lys Phe Arg Gly Gly Cys Phe
1 5 10 15

Asn Leu Leu Phe Lys Gly Ser Val Asp Val Ser Ile Lys Thr Arg Met
20 25 30

Lys Arg Ile Gln Ile Asn Leu Ile Leu Thr Ile Ala Cys Ile Gln Leu
35 40 45

Ser Thr Glu Ser Gln Pro Thr Pro Val Ser Ile Thr Glu Leu Tyr Thr
50 55 60

Ser Ala Ala Thr Arg Lys Pro Asp Pro Ala Val Ala Pro Thr Ser Ala
65 70 75 80

Ala Ser Arg Lys Pro Asp Pro Ala Val Ala Pro Thr Ser Ala Ala Ser
85 90 95

Arg Lys Pro Asp Pro Ala Val Ala Pro Thr Ser Ala Ala Ser Arg Lys
100 105 110

Pro Asp Pro Ala Val Ala Pro Thr Ser Ala Ala Thr Arg Lys Pro Asp
115 120 125

Pro Ala Val Ala Pro Thr Ser Ala Ala Ser Arg Lys Pro Asp Pro Ala
130 135 140

Val Ala Pro Thr Ser Ala Ala Thr Arg Lys Pro Asp Pro Ala Val Ala
145 150 155 160

Pro Thr Ser Ala Ala Ser Arg Lys Pro Asp Pro Ala Ala Asn Thr Gln
165 170 175

His Ser Gln Pro Pro Phe Leu Tyr Glu Asn Ile Gln Cys Val His Gly
180 185 190

Gly Ile Gln Ser Ile Pro Tyr Phe His Thr Phe Ile Met Pro Cys Tyr
195 200 205

Met Arg Leu Thr Thr Gly Gln Gln Ala Ala Phe Lys Gln Gln Gln Lys
210 215 220

Thr Tyr Glu Gln Tyr Ser Leu Asp Pro Glu Gly Ser Asn Ile Thr Arg
225 230 235 240

Trp Lys Ser Leu Ile Arg Pro Asp Leu His Ile Glu Val Trp Phe Thr
245 250 255

Arg His Leu Ile Asp Pro His Arg Gln Leu Gly Asn Ala Leu Ile Arg
260 265 270

Met Pro Asp Leu Pro Val Met Leu Tyr Ser Asn Ser Ala Asp Leu Asn
275 280 285

Leu Ile Asn Asn Pro Glu Ile Phe Thr His Ala Lys Glu Asn Tyr Val
290 295 300

Ile Pro Asp Val Lys Thr Thr Ser Asp Phe Ser Val Thr Ile Leu Ser
305 310 315 320

Met Asp Ala Thr Thr Glu Gly Thr Tyr Ile Trp Arg Val Val Asn Thr
325 330 335

Lys Thr Lys Asn Val Ile Ser Glu His Ser Ile Thr Val Thr Thr Tyr
340 345 350

-continued

```
Tyr Arg Pro Asn Ile Thr Val Val Gly Asp Pro Val Leu Thr Gly Gln
        355                 360                 365

Thr Tyr Ala Ala Tyr Cys Asn Val Ser Lys Tyr Tyr Pro Pro His Ser
    370                 375                 380

Val Arg Val Arg Trp Thr Ser Arg Phe Gly Asn Ile Gly Lys Asn Phe
385                 390                 395                 400

Ile Thr Asp Ala Ile Gln Glu Tyr Ala Asn Gly Leu Phe Ser Tyr Val
                405                 410                 415

Ser Ala Val Arg Ile Pro Gln Gln Lys Gln Met Asp Tyr Pro Pro Pro
            420                 425                 430

Ala Ile Gln Cys Asn Val Leu Trp Ile Arg Asp Gly Val Ser Asn Met
        435                 440                 445

Lys Tyr Ser Ala Val Val Thr Pro Asp Val Tyr Pro Phe Pro Asn Val
    450                 455                 460

Ser Ile Gly Ile Ile Asp Gly His Ile Val Cys Thr Ala Lys Cys Val
465                 470                 475                 480

Pro Arg Gly Val Val His Phe Val Trp Trp Val Asn Asp Ser Pro Ile
                485                 490                 495

Asn His Glu Asn Ser Glu Ile Thr Gly Val Cys Asp Gln Asn Lys Arg
            500                 505                 510

Phe Val Asn Met Gln Ser Ser Cys Pro Thr Ser Glu Leu Asp Gly Pro
        515                 520                 525

Ile Thr Tyr Ser Cys His Leu Asp Gly Tyr Pro Lys Lys Phe Pro Pro
    530                 535                 540

Phe Ser Ala Val Tyr Thr Tyr Asp Ala Ser Thr Tyr Ala Thr Thr Phe
545                 550                 555                 560

Ser Val Val Ala Val Ile Ile Gly Val Ile Ser Ile Leu Gly Thr Leu
                565                 570                 575

Gly Leu Ile Ala Val Ile Ala Thr Leu Cys Ile Arg Cys Cys Ser
            580                 585                 590


<210> SEQ ID NO 9
<211> LENGTH: 533
<212> TYPE: PRT
<213> ORGANISM: Varicella zoster

<400> SEQUENCE: 9

Met Gly Val Lys Val Leu Phe Ala Leu Ile Cys Ile Ala Val Ala Glu
1               5                   10                  15

Ala Ser Val Leu Arg Tyr Asp Asp Phe His Ile Asp Glu Asp Lys Leu
            20                  25                  30

Asp Thr Asn Ser Val Tyr Glu Pro Tyr Tyr His Ser Asp His Ala Glu
        35                  40                  45

Ser Ser Trp Val Asn Arg Gly Glu Ser Ser Arg Lys Ala Tyr Asp His
    50                  55                  60

Asn Ser Pro Tyr Ile Trp Pro Arg Asn Asp Tyr Asp Gly Phe Leu Glu
65                  70                  75                  80

Asn Ala His Glu His His Gly Val Tyr Asn Gln Gly Arg Gly Ile Asp
                85                  90                  95

Ser Gly Glu Arg Leu Met Gln Pro Thr Gln Met Ser Ala Gln Glu Asp
            100                 105                 110

Leu Gly Asp Asp Thr Gly Ile His Val Ile Pro Thr Leu Asn Gly Asp
        115                 120                 125

Asp Arg His Lys Ile Val Asn Val Asp Gln Arg Gln Tyr Gly Asp Val
    130                 135                 140
```

-continued

```
Phe Lys Gly Asp Leu Asn Pro Lys Pro Gln Gly Gln Arg Leu Ile Glu
145                 150                 155                 160

Val Ser Val Glu Glu Asn His Pro Phe Thr Leu Arg Ala Pro Ile Gln
                165                 170                 175

Arg Ile Tyr Gly Val Arg Tyr Thr Glu Thr Trp Ser Phe Leu Pro Ser
            180                 185                 190

Leu Thr Cys Thr Gly Asp Ala Ala Pro Ala Ile Gln His Ile Cys Leu
        195                 200                 205

Lys His Thr Thr Cys Phe Gln Asp Val Val Val Asp Val Asp Cys Ala
    210                 215                 220

Glu Asn Thr Lys Glu Asp Gln Leu Ala Glu Ile Ser Tyr Arg Phe Gln
225                 230                 235                 240

Gly Lys Lys Glu Ala Asp Gln Pro Trp Ile Val Val Asn Thr Ser Thr
                245                 250                 255

Leu Phe Asp Glu Leu Glu Leu Asp Pro Pro Glu Ile Glu Pro Gly Val
            260                 265                 270

Leu Lys Val Leu Arg Thr Glu Lys Gln Tyr Leu Gly Val Tyr Ile Trp
        275                 280                 285

Asn Met Arg Gly Ser Asp Gly Thr Ser Thr Tyr Ala Thr Phe Leu Val
    290                 295                 300

Thr Trp Lys Gly Asp Glu Lys Thr Arg Asn Pro Thr Pro Ala Val Thr
305                 310                 315                 320

Pro Gln Pro Arg Gly Ala Glu Phe His Met Trp Asn Tyr His Ser His
                325                 330                 335

Val Phe Ser Val Gly Asp Thr Phe Ser Leu Ala Met His Leu Gln Tyr
            340                 345                 350

Lys Ile His Glu Ala Pro Phe Asp Leu Leu Leu Glu Trp Leu Tyr Val
        355                 360                 365

Pro Ile Asp Pro Thr Cys Gln Pro Met Arg Leu Tyr Ser Thr Cys Leu
    370                 375                 380

Tyr His Pro Asn Ala Pro Gln Cys Leu Ser His Met Asn Ser Gly Cys
385                 390                 395                 400

Thr Phe Thr Ser Pro His Leu Ala Gln Arg Val Ala Ser Thr Val Tyr
                405                 410                 415

Gln Asn Cys Glu His Ala Asp Asn Tyr Thr Ala Tyr Cys Leu Gly Ile
            420                 425                 430

Ser His Met Glu Pro Ser Phe Gly Leu Ile Leu His Asp Gly Gly Thr
        435                 440                 445

Thr Leu Lys Phe Val Asp Thr Pro Glu Ser Leu Ser Gly Leu Tyr Val
    450                 455                 460

Phe Val Val Tyr Phe Asn Gly His Val Glu Ala Val Ala Tyr Thr Val
465                 470                 475                 480

Val Ser Thr Val Asp His Phe Val Asn Ala Ile Glu Glu Arg Gly Phe
                485                 490                 495

Pro Pro Thr Ala Gly Gln Pro Pro Ala Thr Thr Lys Pro Lys Glu Ile
            500                 505                 510

Thr Pro Val Asn Pro Gly Thr Ser Pro Leu Ile Arg Tyr Ala Ala Trp
        515                 520                 525

Thr Gly Gly Leu Ala
    530
```

VARICELLA ZOSTER

INCORPORATION BY REFERENCE OF RELATED APPLICATIONS

This application is a National Stage of International Application No. PCT/US2020/058859, filed Nov. 4, 2020, which is based upon and claims the benefit of priority under 35 U.S.C. § 119(e) to U.S. Provisional Application No. 62/930,727, filed Nov. 5, 2019, the entire contents of all of which are incorporated herein by reference in their entirety.

FIELD OF THE INVENTION

The present application relates to compositions capable of inducing an immune response against Varicella zoster virus, methods of administering such compositions, and methods of producing such compositions.

STATEMENT

To comply with 37 C.F.R. § 1.821, this application contains sequence listings included in an ASCII text file submitted via EFS-WEB. The ASCII text file has the following attributes: (1) Name: VZV Sequences PCT_ST25.txt, (2) Date of creation: Oct. 26, 2020, (3) File size in bytes: 48,422. Pursuant to MPEP § 2422.03(a), Applicant hereby incorporates by reference the foregoing ASCII text file and all material disclosed therein into this application.

BACKGROUND

Varicella zoster virus (VZV) is a human virus belonging to the α-herpesvirus family. VZV is present worldwide and is highly infectious. Primary infection leads to acute varicella or "chickenpox," usually from exposure either through direct contact with a skin lesion or through airborne spread from respiratory droplets. (Sawyer M H, Chamberlin C J, Wu Y N, Aintablian N, Wallace M R, Detection of varicella-zoster virus DNA in air samples from hospital rooms, 169 J Infect Dis. 91-4 (1994).) After initial infection, VZV establishes lifelong latency in cranial nerve and dorsal root ganglia, and can reactivate years to decades later as herpes zoster (H Z) or "shingles." (Gilden D H, Kleinschmidt-DeMasters B K, LaGuardia J J, Mahalingam R, Cohrs R J, *Neurologic complications of the reactivation of varicella-zoster virus,* 342 N Engl J Med. 635-645 (2000).) More than 90% of adults in the United States acquired the disease in childhood, while the majority of children and young adults have been vaccinated with the live virus vaccine. (Marin M, Guris D, Chaves S S, Schmid S, Seward J F, *Prevention of varicella: recommendations of the Advisory Committee on Immunization Practices* (*ACIP*), MMWR Recomm Rep. 2007; 56:1-40.)

For adults who were not exposed to varicella during childhood, and occasionally to individuals who are immunocompromised, VZV can be life-threatening. Similarly, a VZV infection can be life-threatening to neonates, as the virus is capable of crossing the placenta. With direct contact, VZV is known to be a highly transmissible infectious disease.

Several vaccines capable of inducing an immune response against VZV are commercially available, including VARIVAX and PROQUAD for the prevention of varicella (chickenpox) and SHINGRIX and ZOSTAVAX for the prevention of herpes zoster (shingles). These vaccines have varied efficacy, and there remains a need for improved vaccines against varicella, herpes zoster, and related disorders such as post herpetic neuralgia (PHN).

SUMMARY

The present application provides compositions which induce an immune response against Varicella zoster virus, and thus are capable of vaccinating against varicella, herpes zoster, and related disorders such as post herpetic neuralgia (PHN), methods of administering such compositions, and methods of producing such compositions.

In an embodiment of the present application, a composition which induces an immune response against Varicella zoster virus comprises an optionally truncated VZV glycoprotein or a fragment thereof in combination with a triterpene glycoside saponin-derived adjuvant. The optionally truncated VZV glycoprotein may be VZV glycoprotein E or a fragment thereof, and may have the sequence of SEQ ID No. 1.

The saponin-derived adjuvant may be a compound according to Formula I:

(I)

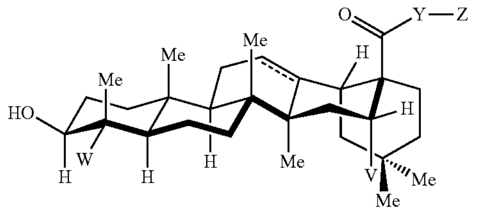

or a pharmaceutically acceptable salt thereof, wherein

--- is a single or double bond;

W is —CHO;

V is —OH;

Y is —O—;

wherein Z is a carbohydrate domain having the structure:

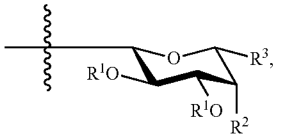

wherein:

$R^1$ is independently H or

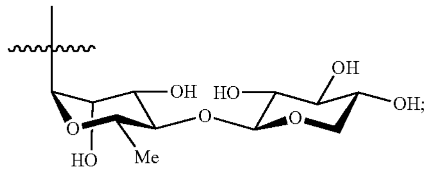

$R^2$ is $NHR^4$;

$R^3$ is $CH_2OH$; and $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

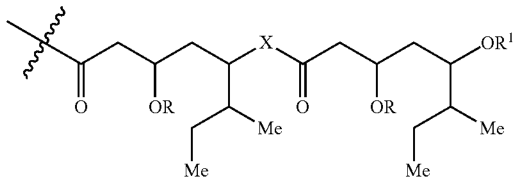

wherein:

X is —O—, —NR—, or T-$R^z$;

T is a covalent bond or a bivalent $C_{1-26}$ saturated or unsaturated, straight or branched, aliphatic or heteroaliphatic chain;

$R^z$ is hydrogen, halogen, —OR, —$OR^x$, —$OR^{1'}$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

$R^x$ is independently hydrogen or an oxygen protecting group selected from the group consisting of alkyl ethers, benzyl ethers, silyl ethers, acetals, ketals, esters, carbamates, and carbonates; and R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur;

$R^{1'}$ is $R^x$ or a carbohydrate domain having the structure:

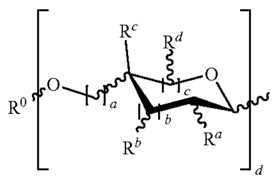

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur.

In a preferred embodiment of the present application, a composition which induces an immune response against Varicella zoster virus comprises a VZV glycoprotein E truncated to remove the carboxy terminal anchor region, which gE is not in the form of a fusion protein, in combination with an adjuvant comprising a compound of Formula II (or a pharmaceutically acceptable salt thereof), a TLR4 agonist, and a liposome-forming compound, such as DOPC, DMPC, DMPG, cholesterol, and/or combinations of the foregoing.

(II)

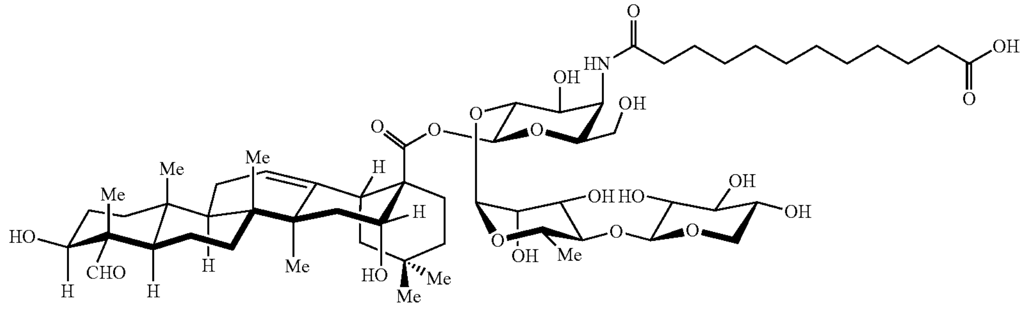

In preferred embodiments, the compound of Formula I or Formula II is in free acid form or choline salt form. In preferred embodiments, the TLR4 agonist is PHAD, MPL® (Monophosphoryl lipid A), or MPLA or variants thereof.

In some of the preferred embodiments, the VZV glycoprotein contains a non-native signal peptide on the N-terminus to improve cleavage. In the context of the present application, such non-native signal peptides together with truncated or untruncated glycoproteins are not considered fusion proteins.

In another preferred embodiment, the present application utilizes an emulsion-based technology instead of or in conjunction with a liposome-forming compound. In some embodiments, the present application provides a combination having liposomes containing a TLR4 agonist and an emulsion containing the compound of Formula I or Formula II (or a pharmaceutically acceptable salt thereof). In some embodiments, the present application provides liposomes containing a TLR4 agonist and the compound of Formula I or Formula II (or a pharmaceutically acceptable salt thereof). In some embodiments, the present application provides an emulsion containing a TLR4 agonist and the compound of Formula I or Formula II (or a pharmaceutically acceptable salt thereof).

The present application also relates to methods of using a composition which induces an immune response against Varicella zoster virus, in the preparation of a medicament for the prevention or amelioration of varicella, herpes zoster, and/or post herpetic neuralgia.

The present application also relates to a method for the prevention or amelioration of varicella, herpes zoster, and/or post herpetic neuralgia, the method comprising administering to a human in need thereof an immunogenic composition or vaccine comprising a composition which induces an immune response against Varicella zoster virus as described above.

BRIEF DESCRIPTION OF THE DRAWINGS

FIG. 1 depicts the sequence of a truncated VZV gE.
FIG. 2 depicts the sequence of a truncated VZV gE.
FIG. 3 depicts the sequence of a VZV gE.
FIG. 4 depicts the sequence of a VZV gE.
FIG. 5 depicts the sequence of a VZV gB.
FIG. 6 depicts the sequence of a VZV gH.
FIG. 7 depicts the sequence of a VZV gI.
FIG. 8 depicts the sequence of a VZV gC.
FIG. 9 depicts the sequence of a truncated VZV gE.

DETAILED DESCRIPTION OF CERTAIN EMBODIMENTS

Figure 10:
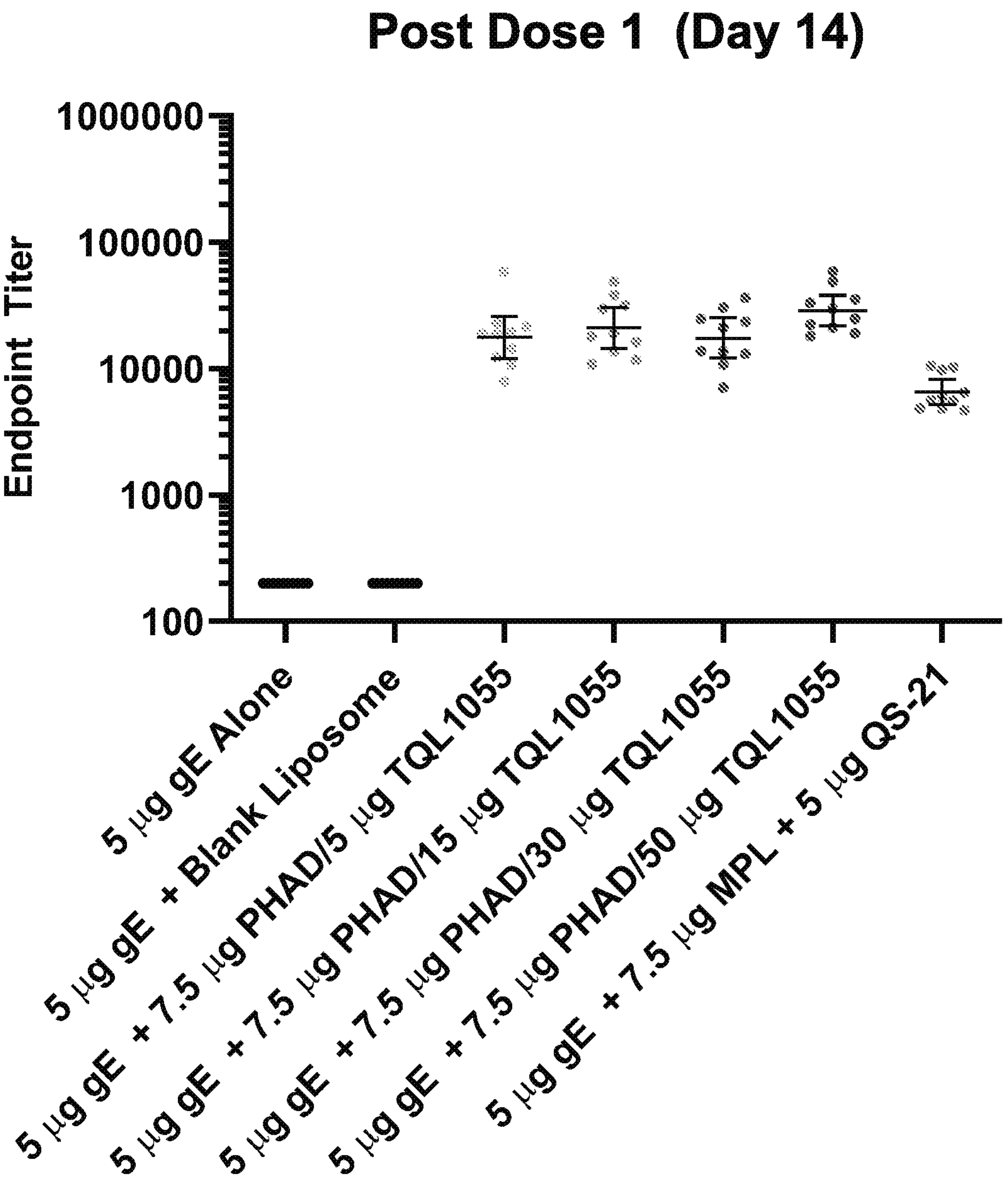
FIG. 10 depicts gE-specific total IgG titer data as explained in Example 1.

In its broadest aspect the present application relates to compositions and regimes for provoking an immune response to VZV. In one aspect the immune response generated by exposure to such compositions is higher and statistically significant when compared to that obtained in individuals who have received no exposure to the compositions of the present application. The immune response may be assessed by analysis of any one or more aspects of CMI response and/or antibody responses using any of the techniques outlined below or those familiar to a person of ordinary skill in the art.

In another aspect, the present application discloses methods for preventing and/or decreasing the severity of varicella, herpes zoster, and post herpetic neuralgia (PHN). Thus, in one aspect, the present application discloses methods of prevention of the incidence of varicella. Where varicella does occur, the severity is reduced compared with an unvaccinated control (amelioration of varicella). In another aspect, the present application discloses methods of prevention of the incidence of herpes zoster. Where zoster does occur, the severity of the reactivation of zoster is reduced compared with an unvaccinated control (amelioration of zoster). In a further aspect, where zoster does occur, the present application discloses methods of prevention of the incidence of PHN. In a further aspect where PHN does occur then the severity of the PHN is suitably reduced compared with an unvaccinated control (amelioration of PHN). Reduction in severity can suitably be assessed by a reduction in the pain caused by varicella, herpes zoster, or PHN, for example, using known measures of burden of pain (e.g. Coplan et al J Pain 2004; 5 (6) 344-56). Reduction in severity can also be assessed by other criteria such as duration of varicella, herpes zoster, or PHN, proportion of body area affected by varicella, herpes zoster, or PHN, or the site of varicella, herpes zoster, or PHN.

The present application provides pharmaceutical compositions comprising the compounds of the present application together with an immunologically effective amount of an antigen associated with Varicella zoster virus (VZV). The application also includes methods of vaccinating a human patient comprising administering an immunologically effective amount of a pharmaceutical compositions or of the compounds of the present application. The application also includes methods for increasing the immune response to a vaccine comprising administering an immunologically effective amount of a pharmaceutical compositions or of the compounds of the present application.

Adjuvant Compounds

Adjuvant compounds of this application include those described generally above, and are further illustrated by the classes, subclasses, and species disclosed herein. In some embodiments, provided compounds are analogs of naturally occurring triterpene glycoside saponins and intermediates thereto. For purposes of this application, the chemical elements are identified in accordance with the Periodic Table of the Elements, CAS version, Handbook of Chemistry and Physics, 75th Ed. Additionally, general principles of organic chemistry are described in Organic Chemistry, Thomas Sorrell, University Science Books, Sausalito: 1999, and March's Advanced Organic Chemistry, 5th Ed., Ed.: Smith, M. B. and March, J., John Wiley & Sons, New York: 2001, the entire contents of which are hereby incorporated by reference.

Description of Exemplary Adjuvant Compounds

In some embodiments, provided adjuvant compounds are analogs of *Quillaja saponins*. In some embodiments, provided adjuvant compounds are prosapogenins. In certain embodiments, provided adjuvant compounds are analogs of QS-7 and QS-21 and possess potent adjuvant activity.

In one aspect, the present application provides adjuvant compounds of Formula I:

(I)

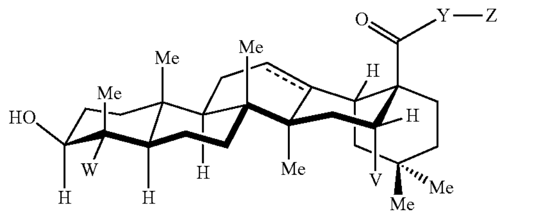

or a pharmaceutically acceptable salt thereof, wherein --- is a single or double bond;

W is —CHO;

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

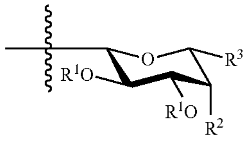

or

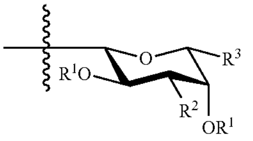

wherein each occurrence of $R^1$ is $R^x$ or a carbohydrate domain having the structure:

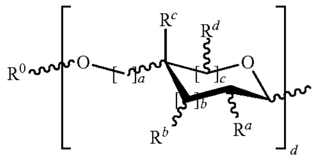

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

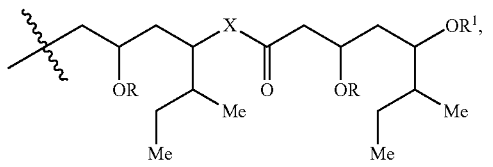

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula II:

(II)

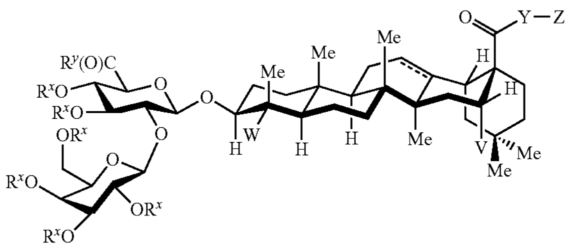

or a pharmaceutically acceptable salt thereof, wherein $\overline{---}$ is a single or double bond;

W is ME, —CHO, or

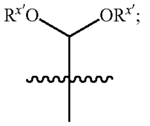

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

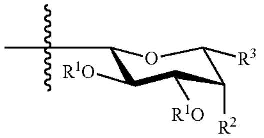 or 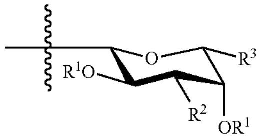

wherein each occurrence of $R^1$ is $R^x$ or a carbohydrate domain having the structure:

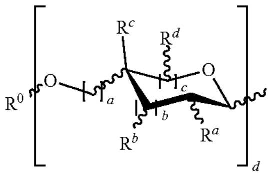

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

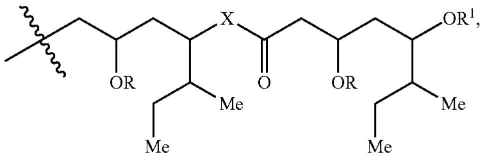

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

$R^y$ is —OH, —OR, or a carboxyl protecting group selected from the group consisting of ester, amides, and hydrazides;

$R^s$ is

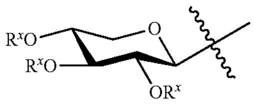

or

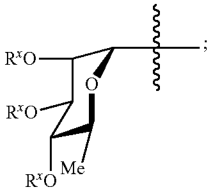

;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula I:

(I)

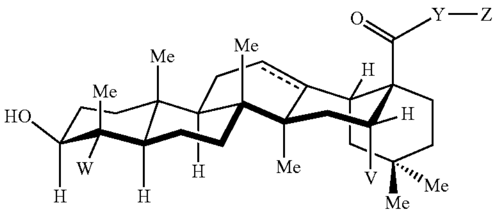

or a pharmaceutically acceptable salt thereof, wherein $\overline{---}$ is a single or double bond;

W is —CHO;

V is —OH;

Y is —O—;

wherein Z is a carbohydrate domain having the structure:

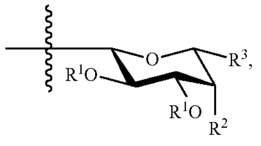

wherein:

$R^1$ is independently H or

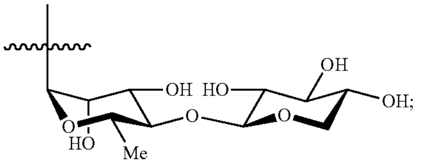

$R^2$ is $NHR^4$;

$R^3$ is $CH_2OH$; and $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

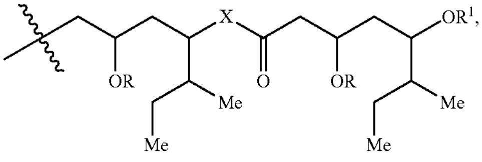

wherein:

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur.

It will be appreciated by one of ordinary skill in the art that the compounds of the present application include but are not necessarily limited to those compounds encompassed in the genus definitions set forth as part of the present section. The compounds encompassed by this application include at least all of the compounds disclosed in the entire specification as a whole, including all individual species within each genus.

In certain embodiments, V is $OR^x$. In certain embodiments V is OH. In certain embodiments, V is H.

In certain embodiments, Y is —O—. In certain embodiments, Y is —NH—. In certain embodiments, Y is —NR—. In certain embodiments, Y is $CH_2$.

In certain embodiments, Z is hydrogen. In certain embodiments, Z is a cyclic or acyclic, optionally substituted moiety. In certain embodiments, Z is an acyl. In certain embodiments, Z is an aliphatic. In certain embodiments, Z is a heteroaliphatic. In certain embodiments, Z is aryl. In certain embodiments Z is arylalkyl. In certain embodiments, Z is heteroacyl. In certain embodiments, Z is heteroaryl. In certain embodiments, Z is a carbohydrate domain having the structure:

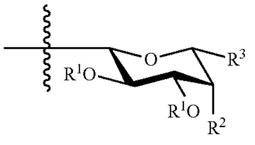
or
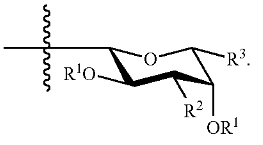

In some embodiments Z is a carbohydrate domain having the structure:

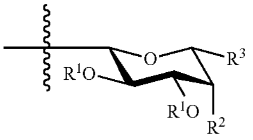

wherein:

$R^1$ is independently H or

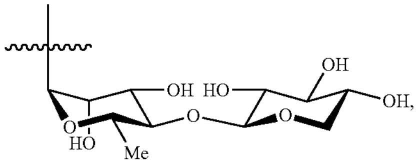

$R^2$ is NH $R^4$, $R^3$ is $CH_2OH$, and $R^4$ is selected from:

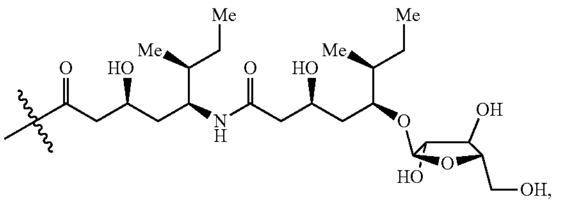

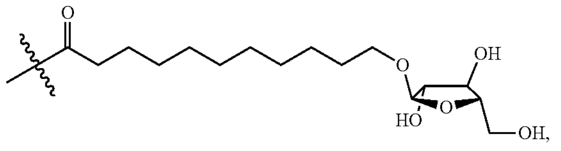

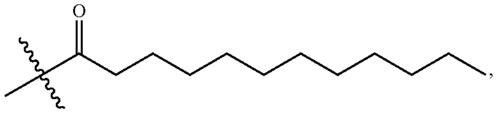

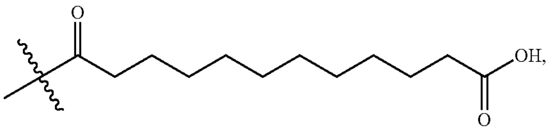

-continued

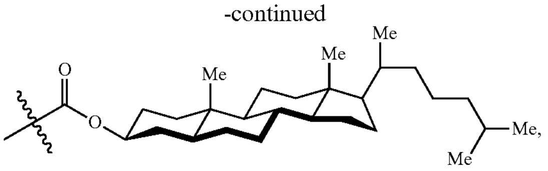

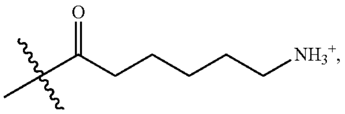

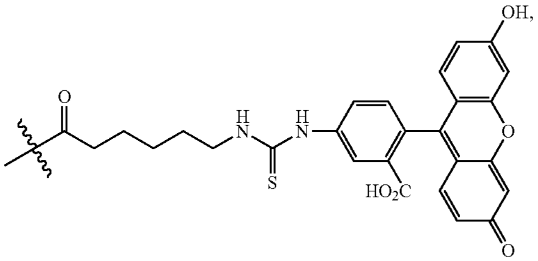

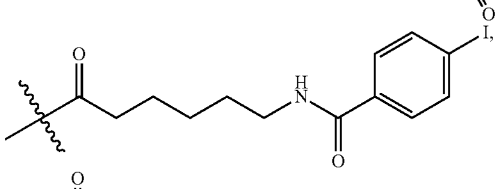

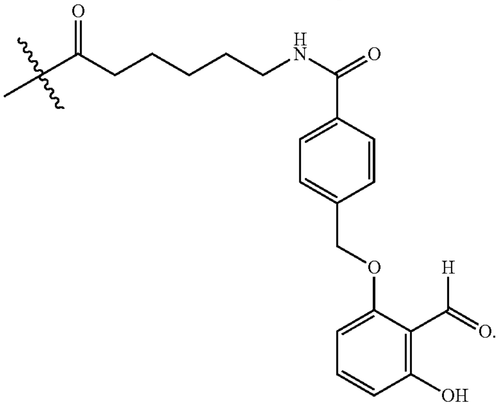

In some embodiments, $R^1$ is $R^x$. In other embodiments, $R^1$ a carbohydrate domain having the structure:

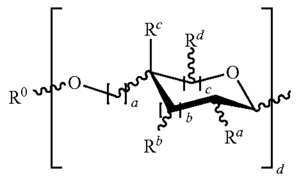

In some aspects, each occurrence of a, b, and c is independently 0, 1, or 2. In some embodiments, d is an integer from 1-5. In some embodiments, each d bracketed structure may be the same. In some embodiments, each d bracketed structure may be different. In some embodiments, the d bracketed structure represents a furanose or a pyranose moiety. In some embodiments, and the sum of b and c is 1 or 2.

In some embodiments, $R^0$ is hydrogen. In some embodiments, $R^0$ is an oxygen protecting group selected from the group. In some embodiments, $R^0$ is an alkyl ether. In some embodiments, $R^0$ is a benzyl ether. In some embodiments, $R^0$ is a silyl ether. In some embodiments, $R^0$ is an acetal. In some embodiments, $R^0$ is ketal. In some embodiments, $R^0$ is an ester. In some embodiments, $R^0$ is a carbamate. In some embodiments, $R^0$ is a carbonate. In some embodiments, $R^0$ is an optionally substituted moiety. In some embodiments, $R^0$ is an acyl. In some embodiments, $R^0$ is a $C_{1-10}$ aliphatic. In some embodiments, $R^0$ is a $C_{1-6}$ heteroaliphatic. In some embodiments, $R^0$ is a 6-10-membered aryl. In some embodiments, $R^0$ is an arylalkyl. In some embodiments, $R^0$ is a 5-10 membered heteroaryl having 1-4 heteroatoms independently selected from nitrogen, oxygen, or sulfur. In some embodiments, $R^0$ is a 4-7 membered heterocyclyl having 1-2 heteroatoms independently selected from the group consisting of nitrogen, oxygen, and sulfur.

In some embodiments, $R^a$ is hydrogen. In some embodiments, $R^a$ is a halogen. In some embodiments, $R^a$ is OH. In some embodiments, $R^a$ is OR. In some embodiments, $R^a$ is $OR^x$. In some embodiments, $R^a$ is $NR_2$. In some embodiments, $R^a$ is NHCOR. In some embodiments, $R^a$ an acyl. In some embodiments, $R^a$ is $C_{1-10}$ aliphatic. In some embodiments, $R^a$ is $C_{1-6}$ heteroaliphatic. In some embodiments, $R^a$ is 6-10-membered aryl. In some embodiments, $R^a$ is arylalkyl. In some embodiments, $R^a$ is 5-10-membered heteroaryl having 1-4 heteroatoms independently selected from nitrogen, oxygen, sulfur. In some embodiments, $R^a$ is 4-7-membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^c$ is hydrogen. In some embodiments, $R^c$ is a halogen. In some embodiments, $R^c$ is OH. In some embodiments, $R^c$ is OR. In some embodiments, $R^c$ is $OR^x$. In some embodiments, $R^c$ is $NR_2$. In some embodiments, $R^c$ is NHCOR. In some embodiments, $R^c$ an acyl. In some embodiments, $R^c$ is $C_{1-10}$ aliphatic. In some embodiments, $R^c$ is $C_{1-6}$ heteroaliphatic. In some embodiments, $R^c$ is 6-10-membered aryl. In some embodiments, $R^c$ is arylalkyl. In some embodiments, $R^c$ is 5-10-membered heteroaryl having 1-4 heteroatoms independently selected from nitrogen, oxygen, sulfur. In some embodiments, $R^c$ is 4-7-membered heterocyclyl having 1-2 heteroatoms independently selected from the group consisting of nitrogen, oxygen, and sulfur.

In some embodiments, $R^d$ is hydrogen. In some embodiments, $R^d$ is a halogen. In some embodiments, $R^d$ is OH. In some embodiments, $R^d$ is OR. In some embodiments, $R^d$ is $OR^x$. In some embodiments, $R^d$ is $NR_2$. In some embodiments, $R^d$is NHCOR. In some embodiments, $R^d$ an acyl. In some embodiments, $R^d$ is $C_{1-10}$ aliphatic. In some embodiments, $R^d$ is $C_{1-6}$ heteroaliphatic. In some embodiments, $R^d$ is 6-10-membered aryl. In some embodiments, $R^d$ is arylalkyl. In some embodiments, $R^d$ is 5-10-membered heteroaryl having 1-4 heteroatoms independently selected from nitrogen, oxygen, sulfur. In some embodiments, $R^d$ is 4-7-membered heterocyclyl having 1-2 heteroatoms independently selected from the group consisting of nitrogen, oxygen, and sulfur.

In some embodiments, $R^2$ is hydrogen. In some embodiments, $R^2$ is a halogen. In some embodiments, $R^2$ is OH. In some embodiments, $R^2$ is OR. In some embodiments, $R^2$ is $OC(O)R^4$. In some embodiments, $R^2$ is $OC(O)OR^4$. In some embodiments, $R^2$ is $OC(O)NHR^4$. In some embodiments, $R^2$ is $OC(O)NRR^4$. In some embodiments, $R^2$ is $OC(O)SR^4$. In some embodiments, $R^2$ is $NHC(O)R^4$. In some embodiments, $R^2$ is $NRC(O)R^4$. In some embodiments, $R^2$ is $NHC(O)OR^4$. In some embodiments, $R^2$ is $NHC(O)NHR^4$. In some embodiments, $R^2$ is $NHC(O)NRR^4$. In some embodiments, $R^2$ is $NHR^4$. In some embodiments, $R^2$ is $N(R^4)_2$. In some embodiments, $R^2$ is $NHR^4$. In some embodiments, $R^2$ is $NRR^4$. In some embodiments, $R^2$ is $N_3$. In some embodiments, $R^2$ is $C_{1-10}$ aliphatic. In some embodiments, $R^2$ is $C_{1-6}$ heteroaliphatic. In some embodiments, $R^2$ is 6-10-membered aryl. In some embodiments, $R^2$ is arylalkyl. In some embodiments, $R^2$ is 5-10 membered heteroaryl having 1-4 heteroatoms independently selected from the group consisting of nitrogen, oxygen, and sulfur. In some embodiments, $R^2$ is 4-7-membered heterocyclyl having 1-2 heteroatoms independently selected from the group consisting of nitrogen, oxygen, and sulfur.

In some embodiments, $R^3$ is hydrogen. In some embodiments, $R^3$ is a halogen. In some embodiments, $R^3$ is $CH_2OR^1$. In some embodiments, $R^3$ is an acyl. In some embodiments, $R^3$ is $C_{1-10}$ aliphatic. In some embodiments, $R^3$ is $C_{1-6}$ heteroaliphatic. In some embodiments, $R^3$ is 6-10-membered aryl. In some embodiments, $R^3$ is arylalkyl. In some embodiments, $R^3$ is 5-10-membered heteroaryl having 1-4 heteroatoms independently selected from the group consisting of nitrogen, oxygen, and sulfur. In some embodiments, $R^3$ is 4-7-membered heterocyclyl having 1-2 heteroatoms independently selected from the group consisting of nitrogen, oxygen, and sulfur.

In some embodiments, $R^4$ is $-T-R^z$. In some embodiments, $R^4$ is $—C(O)-T-R^z$. In some embodiments, $R^4$ is $—NH-T-R^z$. In some embodiments, $R^4$ is $—O-T-R^z$. In some embodiments, $R^4$ is $—S-T-R^z$. In some embodiments, $R^4$ is $—C(O)NH-T-R^z$. In some embodiments, $R^4$ is $C(O)O-T-R^z$. In some embodiments, $R^4$ is $C(O)S-T-R^z$. In some embodiments, $R^4$ is $C(O)NH-T-O-T-R^z$. In some embodiments, $R^4$ is $—O-T-R^z$. In some embodiments, $R^4$ is $-T-O-T-R^z$. In some embodiments, $R^4$ is $-T-S-T-R^z$. In some embodiments, $R^4$ is

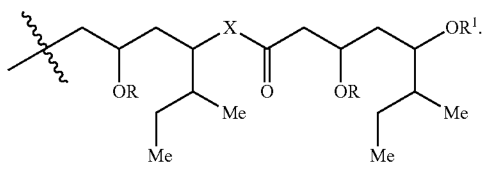

In some embodiments, X is —O—. In some embodiments, X is —NR—. In some embodiments, X is T-$R^z$.

In some embodiments, T is a covalent bond or a bivalent $C_{1-26}$ saturated or unsaturated, straight or branched, aliphatic or heteroaliphatic chain.

In some embodiments, $R^z$ is hydrogen. In some embodiments, $R^z$ is a halogen. In some embodiments, $R^z$ is —OR. In some embodiments, $R^z$ is —$OR^x$. In some embodiments, $R^z$ is —$OR^1$. In some embodiments, $R^z$ is —$OR^{1'}$. In some embodiments, $R^z$ is —SR. In some embodiments, $R^z$ is $NR_2$. In some embodiments, $R^z$ is —C(O)OR. In some embodiments, $R^z$ is —C(O)R. In some embodiments, $R^z$ is —NHC(O)R. In some embodiments, $R^z$ is —NHC(O)OR. In some embodiments, $R^z$ is NC(O)OR. In some embodiments, $R^z$ is an acyl. In some embodiments, $R^z$ is arylalkyl. In some embodiments, $R^z$ is heteroarylalkyl. In some embodiments, $R^z$ is $C_{1-6}$ aliphatic. In some embodiments, $R^z$ is 6-10-membered aryl. In some embodiments, $R^z$ is 5-10-membered heteroaryl having 1-4 heteroatoms independently selected from nitrogen, oxygen, or sulfur. In some embodiments, $R^z$ is 4-7-membered heterocyclyl having 1-2 heteroatoms independently selected from the group consisting of nitrogen, oxygen, and sulfur.

In some embodiments, $R^x$ is hydrogen. In some embodiments, $R^x$ is an oxygen protecting group. In some embodiments, $R^x$ is an alkyl ethers. In some embodiments, $R^x$ is a benzyl ether. In some embodiments, $R^x$ is silyl ether. In some embodiments, $R^x$ is an acetal. In some embodiments, $R^x$ is ketal. In some embodiments, $R^x$ is ester. In some embodiments, $R^x$ is carbamate. In some embodiments, $R^x$ is carbonate.

In some embodiments, $R^y$ is —OH. In some embodiments, $R^y$ is —OR. In some embodiments, $R^y$ is a carboxyl protecting group. In some embodiments, $R^y$ is an ester. In some embodiments, $R^y$ is an amide. In some embodiments, $R^y$ is a hydrazide.

In some embodiments, $R^s$ is

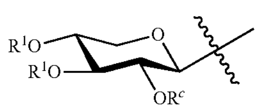

or

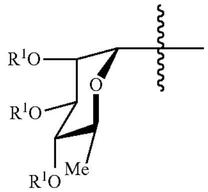

.

In some embodiments, $R^{x'}$ is optionally substituted 6-10-membered aryl. In some embodiments, $R^{x'}$ is optionally substituted $C_{1-6}$ aliphatic. In some embodiments, $R^{x'}$ is optionally substituted or $C_{1-6}$ heteroaliphatic having 1-2 heteroatoms independently selected from the group consisting of nitrogen, oxygen, and sulfur. In some embodiments, two $R^{x'}$ are taken together to form a 5-7-membered heterocyclic ring having 1-2 heteroatoms independently selected from the group consisting of nitrogen, oxygen, and sulfur.

In some embodiments, R is hydrogen. In some embodiments, R is an acyl. In some embodiments, R is arylalkyl. In some embodiments, R is 6-10-membered aryl. In some embodiments, R is $C_{1-6}$ aliphatic. In some embodiments, R is $C_{1-6}$ heteroaliphatic having 1-2 heteroatoms independently selected from the group consisting of nitrogen, oxygen, and sulfur. In some embodiments, two R on the same nitrogen atom are taken with the nitrogen atom to form a 4-7-membered heterocyclic ring having 1-2 heteroatoms independently selected from the group consisting of nitrogen, oxygen, and sulfur.

In some embodiments, $R^{1'}$ has the same embodiments as $R^1$.

Exemplary compounds of Formula I are set forth in Table 1 below:

TABLE 1

| EXEMPLARY COMPOUNDS OF FORMULA I |
| --- |
| 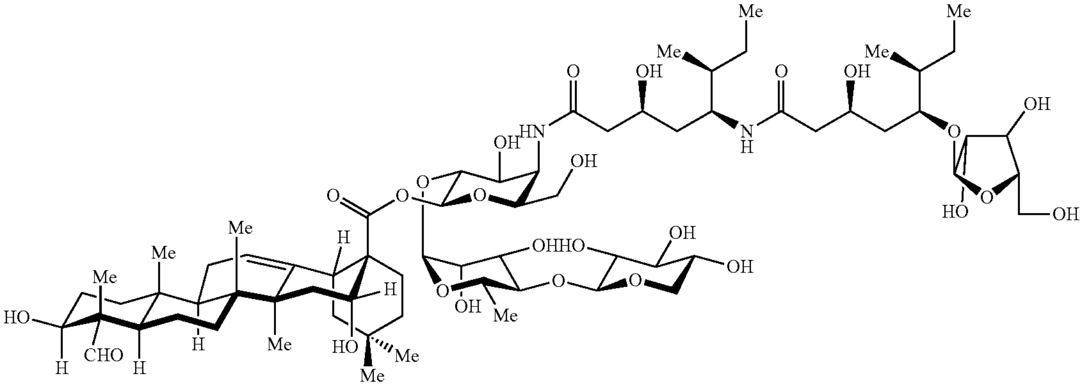 I-1 |

TABLE 1-continued
EXEMPLARY COMPOUNDS OF FORMULA I
I-2
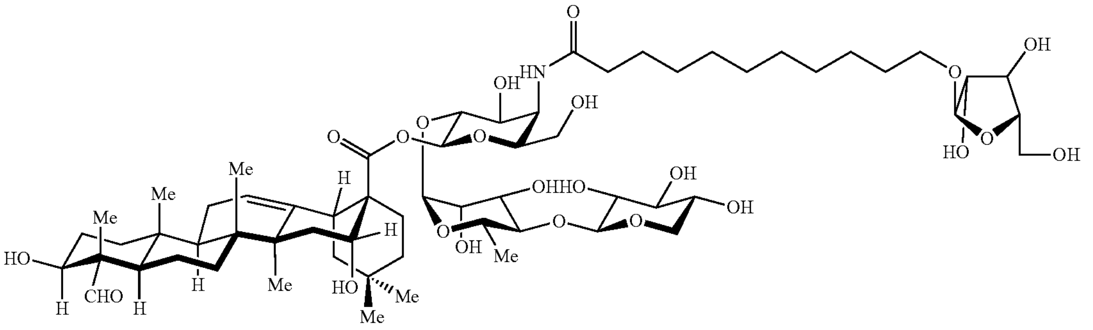
I-3
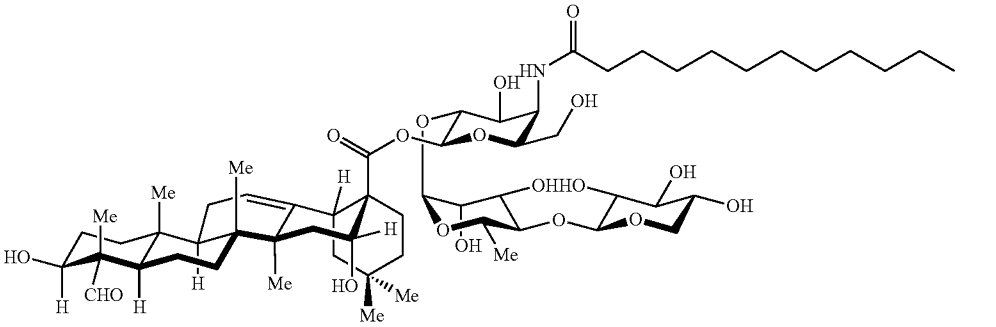
I-4
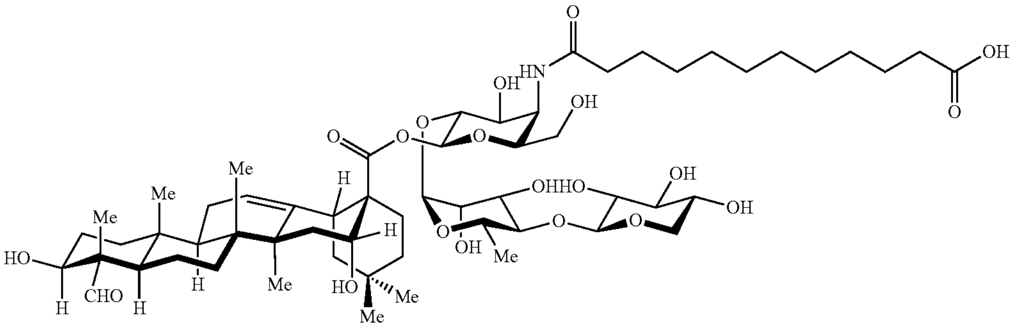
I-5
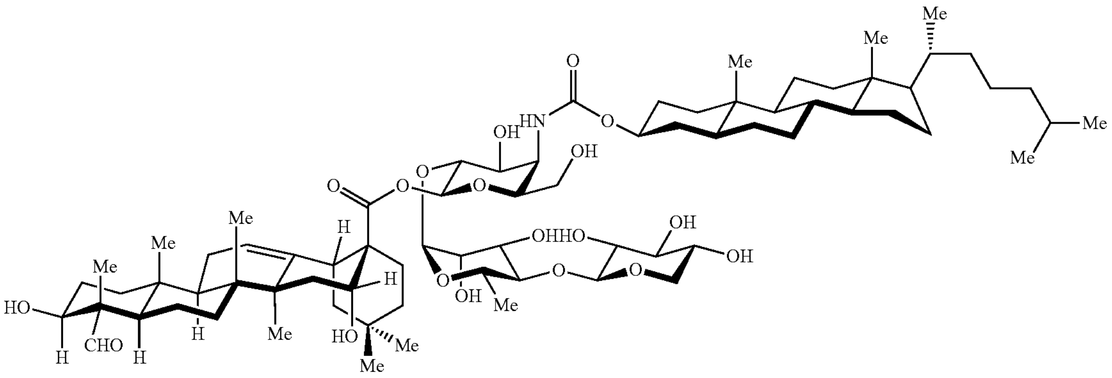

TABLE 1-continued
EXEMPLARY COMPOUNDS OF FORMULA I
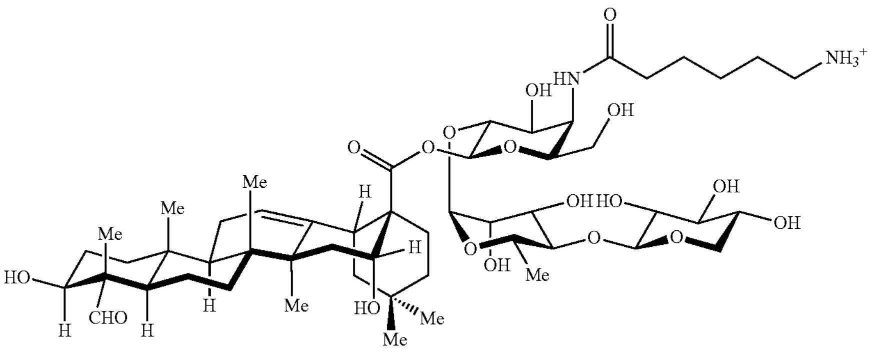
I-6
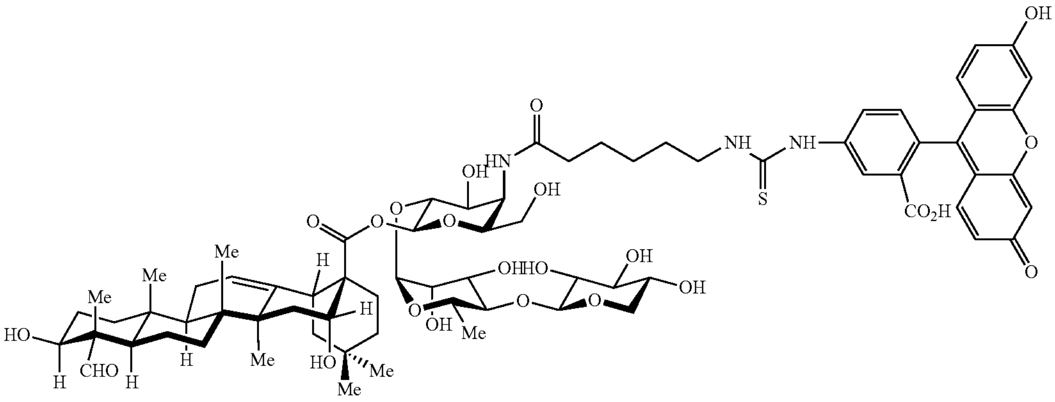
I-7
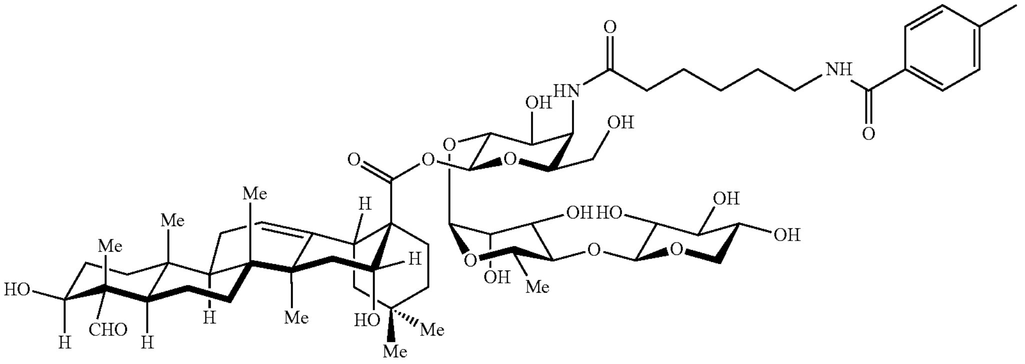
I-8
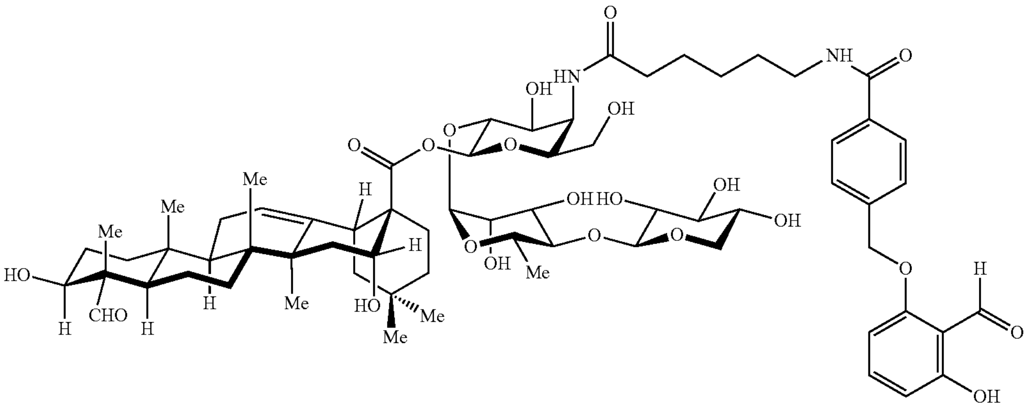
I-9
It will be appreciated that it is not an object of the present subject matter to claim compounds disclosed in the prior art that are the result of isolation or degradation studies on naturally occurring prosapogenins or saponins.

Synthesis of Adjuvant Compounds

Adjuvant compounds of the present application may be synthesized according to the approaches set forth in WO2017079582A1 and/or WO2018191598A1.

Varicella Zoster Antigens

The VZV antigen for use in the present application is an optionally truncated VZV glycoprotein, a fragment thereof, or an immunogenic derivative thereof. The optionally truncated VZV glycoprotein may be VZV glycoprotein E (gE) (VZV gE is also known as gp1), a fragment thereof, or an immunogenic derivative thereof, and may have the sequence of SEQ ID No. 1.

In one aspect the VZV gE is a truncated gE having the sequence of SEQ ID No. 1 (FIG. 1), and as disclosed in Virus research, vol 40, 1996 p 199 ff, herein incorporated fully by reference. In another aspect, the VZV gE is a truncated gE having the sequence of SEQ ID No. 2 (FIG. 2). In another aspect, the VZV gE is a truncated gE having the sequence of SEQ ID No. 9 (FIG. 9). In another aspect, the VZV gE is gE having the sequence of SEQ ID No. 3 (FIG. 3). In another aspect, the VZV gE is gE having the sequence of SEQ ID No. 4 (FIG. 4). In another aspect, the VZV gE is a truncated version of SEQ ID No. 3 or 4.

Vaccine Compositions

Vaccine preparation is generally described in New Trends and Developments in Vaccines, Voller et al. (eds), University Park Press, Baltimore, Md., 1978.

In an embodiment of the present application, a composition which induces an immune response against Varicella zoster virus comprises an optionally truncated VZV glycoprotein or a fragment thereof in combination with a triterpene glycoside saponin-derived adjuvant. The optionally truncated VZV glycoprotein may be VZV glycoprotein E or a fragment thereof or may have the sequence of any of SEQ ID Nos. 1-4, and 9 (FIGS. 1-4, and 9). The saponin-derived adjuvant may be a compound according to Formula I as described previously.

In a preferred embodiment of the present application, a composition which induces an immune response against Varicella zoster virus comprises a VZV glycoprotein E truncated to remove the carboxy terminal anchor region, which gE is not in the form of a fusion protein, in combination with an adjuvant comprising a compound of Formula II (or a pharmaceutically acceptable salt thereof, e.g. a choline salt), a TLR4 agonist (e.g. MPLA, PHAD, MPL®), and a liposome-forming compound (e.g. DOPC, DMPC, DMPG, cholesterol, and/or combinations of the foregoing).

(II)

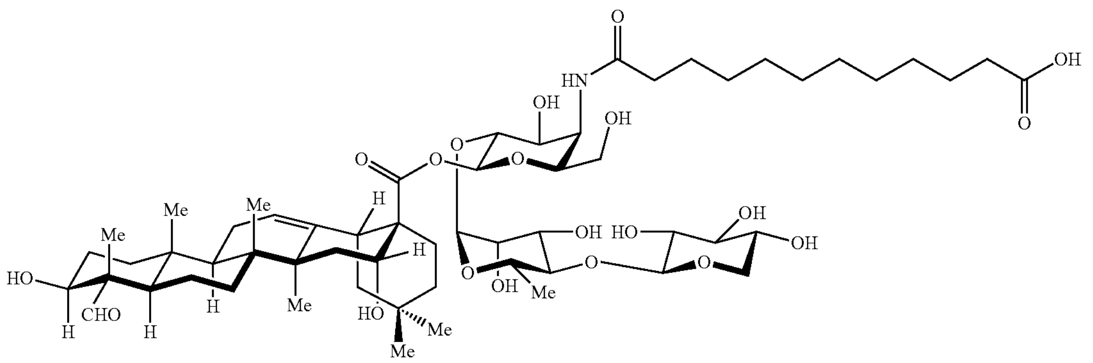

In another aspect, the VZV antigen may include, by way of example, VZV gB (SEQ ID No. 5, FIG. 5), VZV gH (SEQ ID No. 6, FIG. 6), VZV gC (SEQ ID No. 8, FIG. 8), VZV gI (SEQ ID No. 7, FIG. 7), IE63 (e.g. see, Huang et al. J. Virol. 1992, 66: 2664, Sharp et al. J. Inf. Dis. 1992, 165:852, Debrus, J. Virol. 1995 May; 69(5):3240-5 and references therein), IE62 (e.g. see Arvin et al. J. Immunol. 1991 146:257, Sabella J. Virol. 1993 December; 67(12):7673-6 and references therein) ORF4 or ORF 10 (Arvin et al. Viral Immunol. 2002 15: 507.). In another aspect, the VZV antigen may be a truncated version of any of the foregoing.

The present application herein also contemplates that antigen combinations may be used with the live attenuated or killed VZV, and in one aspect a truncated gE as discussed above (SEQ ID Nos. 1, 2, or 9) may be included in any such combination. In one aspect the present application relates to combinations of truncated gE (SEQ ID Nos. 1, 2, or 9) with IE63 and truncated gE (SEQ ID Nos. 1, 2, or 9) with IE62, for example.

Embodiments of a gE antigen, derivatives thereof, and production thereof is described in EP0405867 and references therein (see also Vafai A. Antibody binding sites on truncated forms of varicella-zoster virus gpl(gE) glycoprotein Vaccine 1994 12:1265-9). EP0192902 also discloses embodiments of gE and production thereof.

In some of the preferred embodiments, the VZV glycoprotein contains a non-native signal peptide on the N-terminus to improve cleavage. In the context of the present application, such non-native signal peptides together with truncated or untruncated glycoproteins are not considered fusion proteins.

In another preferred embodiment, the present application utilizes an emulsion-based technology instead of or in conjunction with a liposome-forming compound.

Vaccine compositions, VZV antigens, and derivatives of VZV antigens can be tested for suitable immunogenic activity by use in the model systems by clinical trials in humans. One or more of the following indicators of activity are suitable for consideration in assessment of immunogenic activity: (1) Increased CD4 or CD8 T cell responses to VZV or antigen derivatives; (2) Elevation in VZV or antigens derivative specific antibodies; (3) Enhanced production of cytokines such as interferon γ or IL-2 or TNF a, (4) Enhanced expression of CD40L on CD4 and CD8 T cells; and/or (5) Reduction in the incidence of zoster below the incidence found in the general population of similarly at risk individuals, and likewise reduced disease severity and/or associated pain below the incidence found in the general population of similarly at risk individuals.

In another aspect, the present application relates to vaccine compositions comprising VZV antigen in combination with live attenuated or killed VZV. Suitable combinations of antigens include, for example, optionally truncated gE (SEQ ID No. 1, 2, 9), fragments thereof, or immunogenic derivatives thereof. The combined composition, or either or both of the individual components may additionally comprise an adjuvant composition as set forth in the present application.

Where a live attenuated strain is used, in one aspect the live attenuated VZV strain is the OKA strain, a strain well known in the art, for example as disclosed in Arbeter et al. (Journal of Pediatrics, vol 100, No 6, p 886 ff), WO9402596, and references therein, such as U.S. Pat. No. 3,985,615, all incorporated herein by reference. Any other suitable live attenuated strain may also be used in the present application. For example, the VARILRIX and VARIVAX strains are both appropriate and commercially available and could be employed. VZV-Dumas (either attenuated or inactivated) could also be employed. Whole inactivated VZV strains, such as inactivated VZV OKA are also suitable for use in the subject matter of the present application.

The amount of VZV antigen used in vaccine compositions of the present application is selected as an amount which induces an immunoprotective response without significant, adverse side effects. Such amount will vary depending upon which specific immunogen is employed and how it is presented. Generally, it is expected that each dose will comprise 1-1000 μg of protein, such as 2-100 μg, or 5-60 μg. Where gE (SEQ ID No 1, 2, 3, 4, or 9) is used then in one aspect 25-100 μg of gE (SEQ ID No 1, 2, 3, 4, or 9) may be used in humans, such as 40-100 μg of gE (SEQ ID No 1, 2, 3, 4, or 9) for human use, in one aspect about 25 μg, about 50 μg or about 100 μg of gE (SEQ ID No 1, 2, 3, 4, or 9), suitably 25 μg, 50 μg or 100 μg gE (SEQ ID No 1, 2, 3, 4, or 9). For the OKA strain, for example, a suitable dose is 500-50000 pfu/0.5 ml, such as 2000-6000 pfu/0.5 ml, with a suitable dose of the Oka strain for example being 6000-25,000 per dose, for example 10,000 pfu/dose. Higher doses such as 30,000 pfu, 40000 pfu, 50,000 pfu 60,000 pfu, 70000 pfu, 80000 pfu, 90000 pfu or even 100000 pfu may be employed.

An optimal amount for a particular vaccine can be ascertained by standard studies involving observation of appropriate immune responses in subjects. Following an initial vaccination, subjects may receive one or several booster immunizations adequately spaced. The composition(s) of the present application may be formulated for any appropriate manner of administration, including for example, topical, oral, nasal, mucosal, intravenous, intradermal, intraperitoneal, subcutaneous and intramuscular administration. Delivery of the OKA strain is, in one aspect, by subcutaneous delivery.

In another embodiment, a gE antigen (SEQ ID No. 1, 2, 3, 4, or 9), or immunogenic derivative or immunogenic fragment thereof, may be used with an adjuvant composition of the present application to provide an immunogenic composition or vaccine. That is, the gE antigen (SEQ ID No. 1, 2, 3, 4, or 9) or immunogenic derivative or immunogenic fragment thereof may be used in a vaccination schedule in the absence of a live attenuated strain or whole inactivated strain. Thus, the application relates to an immunogenic composition or vaccine comprising gE (SEQ ID No. 1, 2, 3, 4, or 9) or immunogenic derivative or immunogenic fragment thereof in combination with an adjuvant composition according to the present application.

In one aspect of the present application, a gE truncate is used in which gE has a C terminal truncation. In one aspect the truncation removes from 4 to 20 percent of the total amino acid residues at the carboxy terminal end. In one aspect the gE is lacking the carboxy terminal anchor region (suitably approximately amino acids 547-623 of the wild type sequence). In one aspect gE is a truncated gE having the sequence of SEQ ID No. 1 (FIG. 1) and as disclosed in Virus research, (Haumont et al Vol 40, 1996 p 199-204), herein incorporated fully by reference. In one aspect, with respect to SEQ ID No. 1, Thr 40 is substituted for Ile 40 (i.e. p.Ile40Thr). In one aspect, with respect to SEQ ID No. 1, Leu 536 is substituted for Ile 536 (i.e. p.Ile536Leu). In one aspect, both substitutions are made.

In one aspect gE is a truncated gE having the sequence of SEQ ID No. 2 (FIG. 2). In one aspect gE is a truncated gE having the sequence of SEQ ID No. 9 (FIG. 9). In another aspect of the present application, the composition comprises full length gE (SEQ ID Nos. 3 or 4, FIG. 3 or 4).

In another aspect, the composition comprises a truncated gE having a portion of SEQ ID Nos. 3 or 4. In one aspect, with respect to SEQ ID No. 3, Ile 40 is substituted for Thr 40 (i.e. p.Thr40Ile). In one aspect, with respect to SEQ ID No. 3, Ile 536 is substituted for Leu 536 (i.e. p.Leu536Ile). In one aspect, both substitutions are made.

In another aspect the gE or derivative or fragment thereof is lyophilized. In another aspect the gE or derivative or fragment thereof is reconstituted in a solution containing an adjuvant composition according to the present application (such as an adjuvant containing Formula II, cholesterol, DOPC and a TLR4 agonist) before delivery.

In one embodiment the composition or vaccine comprises gE and an adjuvant composition according to the present application and does not comprise an IE63 antigen or portion thereof. In one embodiment the composition or vaccine comprises gE (SEQ ID No. 1, 2, 3, 4, or 9) and an adjuvant composition according to the present application and does not comprise any other VZV antigen. In one embodiment the composition or vaccine comprises gE (SEQ ID No. 1, 2, 3, 4, or 9) and an adjuvant according to the present application and does not comprise any other viral antigen.

In one aspect the gE or immunogenic fragment thereof is not in the form of a fusion protein. In the context of the present application, non-native signal peptides together with truncated or untruncated glycoproteins are not considered fusion proteins.

In one aspect the composition or vaccine consists essentially of the compound of Formula II, a truncated VZV gE antigen and liposomes comprising DOPC, DMPC, DMPG, cholesterol, and/or combinations of the foregoing, and a TLR4 agonist.

In one aspect the composition or vaccine consists of the compound of Formula II, a truncated VZV gE antigen and liposomes comprising cholesterol and a TLR4 agonist, and a pharmaceutically acceptable carrier.

The term 'immunogenic derivative' encompasses any molecule which retains the ability to induce an immune response to VZV following administration to man. Immunogenic compounds herein are suitably capable of reacting detectably within an immunoassay (such as an ELISA or T-cell stimulation assay) with antisera and/or T-cells from a patient with VZV. Screening for immunogenic activity can be performed using techniques well known to the skilled artisan. For example, such screens can be performed using methods such as those described in Harlow and Lane, Antibodies: A Laboratory Manual, Cold Spring Harbor Laboratory, 1988.

Immunogenic fragments as described herein are immunogenic derivatives which retain the ability to induce an immune response to VZV following administration to man.

Suitable methods for the generation of derivatives are well known in the art and include standard molecular biology techniques as disclosed, for example, in Sambrook et al [Molecular Cloning: A Laboratory Manual, third edition, 2000, Cold Spring Harbor Laboratory Press], such as techniques for the addition, deletion, substitution or rearrangement of amino acids or chemical modifications thereof. In one aspect derivatives include, for example, truncations or other fragments.

In one aspect derivatives in the context of this application are amino acid sequences comprising epitopes, i.e., antigenic determinants substantially responsible for the immunogenic properties of a polypeptide and being capable of eliciting an immune response, in one aspect being T cell epitopes.

In one aspect, the level of immunogenic activity of the immunogenic derivative is at least about 50%, in one aspect at least about 70% and in one aspect at least or greater than about 90% of the immunogenicity for the polypeptide from which it is derived, suitably as assessed by immunoassay techniques described above. In some aspects of the present application, immunogenic portions may be identified that have a level of immunogenic activity greater than that of the corresponding full-length polypeptide, e.g., having greater than about 100% or 150% or more immunogenic activity.

Vaccine Regimes

In one aspect the present application relates to a prime boost regime wherein a VZV antigen, in one aspect an adjuvanted antigen, is delivered first, after which the immune system is boosted with delivery of an attenuated VZV.

A prime boost regime in humans comprises, in one aspect, priming with 25-100 μg gE (SEQ ID No. 1, 2, 3, 4, or 9), in one aspect 40-100 μg gE (SEQ ID No. 1, 2, 3, 4, or 9), such as 50 or about 50 μg gE (SEQ ID No. 1, 2, 3, 4, or 9), or an immunogenic derivative thereof, adjuvanted with an adjuvant of Formula II, and boosting with the OKA strain of VZV.

Where prime boost regimes are used, or where multiple vaccination regimes are used, then 2, 3, 4 or more immunizations may be employed. Suitable regimes for prime boost include 1, 2, 3, 4, 5 or 6 months between individual immunizations. A prime boost schedule comprises, in one aspect, delivery of a VZV antigen or immunogenic derivative thereof, suitably an adjuvanted VZV antigen or derivative, at 0 months and boosting with a live attenuated VZV at 2 months.

In an alternative delivery schedule, there is concomitant delivery of both of the two individual components (VZV antigen or derivative and live attenuated VZV) at both 0 and 2 months.

In an alternative delivery schedule, there is delivery of VZV antigen or derivative thereof (no live attenuated or killed VZV) at both 0 and 2 months. The VZV antigen may be, for example, VZV gE (SEQ ID No. 1, 2, 3, 4, or 9).

In an alternative delivery schedule, there is delivery of a VZV antigen or a derivate thereof in a single dose. The VZV antigen may be, for example. VZV gE (SEQ ID No. 1, 2, 3, 4, or 9).

The composition or vaccine is suitably used in the population of people 50 or older than 50. Suitably the population is the population of those older than 55, 60, 65, 70, 75, 80, or older than 80. Suitably the population is 50-70 years.

In one aspect the population of individuals are those who have had varicella or who have had a live varicella vaccine.

Thus, the present application relates to use of a composition as described above in the preparation of a medicament for the prevention or amelioration of herpes zoster reactivation and/or post herpetic neuralgia in a population of people 50 or above.

The present application thus also relates to a method for the prevention or amelioration of herpes zoster reactivation and/or post herpetic neuralgia, the method comprising delivering to an individual in need thereof a composition of the present application.

In one aspect the composition of the first and second aspects of the present application are used in those individuals in whom the varicella zoster virus has not reactivated.

The composition may be used at doses and delivery routes as outlined above for the first aspect of the invention. Specifically, the amount of gE antigen (SEQ ID No. 1, 2, 3, 4, or 9) is selected as an amount which induces an immunoprotective response without significant, adverse side effects in typical vaccines. Such amount will vary depending upon which specific immunogen is employed and how it is presented. Generally, it is expected that each dose will comprise 1-1000 μg of protein, such as 2-100 μg, or 5-60 μg. Where gE (SEQ ID No. 1, 2, 3, 4, or 9) is used then suitably 25-100 μg gE (SEQ ID No. 1, 2, 3, 4, or 9) is used, in one aspect 40-100 μg of gE (SEQ ID No. 1, 2, 3, 4, or 9), such as about 25 μg, 50 μg or about 100 μg of gE (SEQ ID No. 1, 2, 3, 4, or 9), suitably 25 μg, 50 μg or 100 μg gE (SEQ ID No. 1, 2, 3, 4, or 9). An optimal amount for a particular vaccine can be ascertained by standard studies involving observation of appropriate immune responses in subjects. Following an initial vaccination, subjects may receive one or several booster immunization adequately spaced.

In one aspect the gE (SEQ ID No. 1, 2, 3, 4, or 9) and adjuvant composition or vaccine is used in a one dose delivery regime. In one aspect the gE (SEQ ID No. 1, 2, 3, 4, or 9) and adjuvant composition or vaccine is used in a two-dose delivery regime. In one aspect the composition or vaccine of the invention is used in a 2 dose regime with a 2 month spacing between doses.

Vaccine Kits and Medicaments

In another embodiment, the present application relates to a kit comprising a live attenuated VZV or inactivated whole VZV and a VZV antigen.

In another aspect, the present application relates to a kit comprising, as separate components, an adjuvant composition according to the present application and a gE antigen or immunogenic fragment thereof, as described above, suitable for extemporaneous preparation of a vaccine composition. In one aspect both components are liquids. In one aspect one component is lyophilized and is suitable for reconstitution with the other component. In one aspect the kit comprises a gE antigen having the sequence SEQ ID No. 1 and an adjuvant comprising the compound of Formula II and liposomes comprising cholesterol and a TLR4 agonist.

In yet another embodiment, the present application relates to use of a VZV antigen, including a composition comprising gE (SEQ ID No. 1, 2, 3, 4, or 9), or an immunogenic derivative or immunogenic fragment thereof in combination with an adjuvant composition according to the present application, in the preparation of a medicament for the prevention or amelioration of herpes zoster reactivation and/or post herpetic neuralgia.

Further Embodiments

In a series of further specific or alternate embodiments, the present application also provides:

1.1 An immunogenic composition comprising:

a varicella zoster virus antigen, and a compound of Formula I:

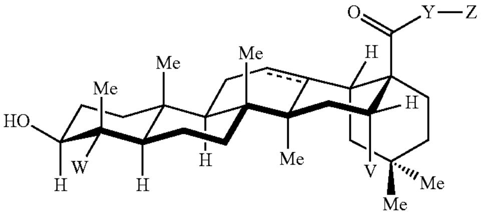

(I)

or a pharmaceutically acceptable salt thereof, wherein

--- is a single or double bond;

W is —CHO;

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

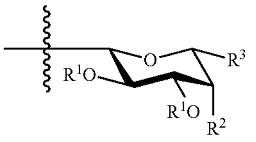

or

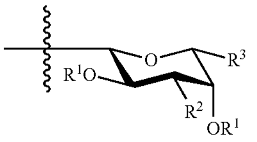

wherein each occurrence of $R^1$ is $R^x$ or a carbohydrate domain having the structure:

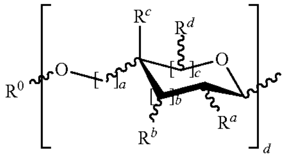

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

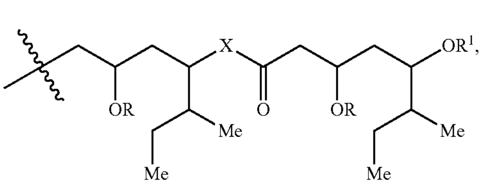

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

1.2. The immunogenic composition of 1.1, wherein the compound of Formula I is:

1.12. The immunogenic composition of any of 1.1 to 1.11, further comprising a liposome-forming compound.

1.13. The immunogenic composition of 1.12, wherein the liposome-forming compound forms liposomes containing the TLR4 agonist.

1.14. The immunogenic composition of any of 1.12 to 1.13, wherein the liposome-forming compound is selected from the group consisting of DOPC, DMPC, DMPG, cholesterol, and combinations thereof.

1.15. The immunogenic composition according to any of 1.1 to 1.11, further comprising an emulsion.

1.16. The immunogenic composition according to 1.15, wherein the emulsion is an oil-in-water emulsion.

1.17. The immunogenic composition according to any of 1.15 to 1.16, wherein the emulsion contains the compound of Formula I or pharmaceutically acceptable salt thereof.

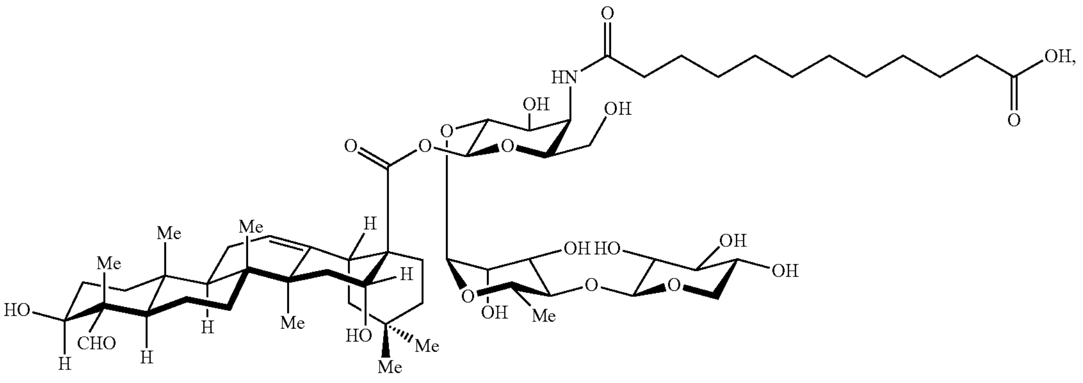

or a pharmaceutically acceptable salt thereof.

1.3. The immunogenic composition of any of 1.1 to 1.2, wherein the compound of Formula I is in free acid form.

1.4. The immunogenic composition of any of 1.1 to 1.2, wherein the compound of Formula I is in choline salt form.

1.5. The immunogenic composition of any of 1.1 to 1.4, wherein the varicella zoster virus antigen is a varicella zoster virus gE antigen truncated to remove the carboxy terminal anchor region.

1.6. The immunogenic composition of any of 1.1 to 1.5, wherein the varicella zoster virus gE antigen is a truncate.

1.7. The immunogenic composition of any of 1.1 to 1.6, wherein the varicella zoster virus gE antigen is a C-terminal truncate.

1.8. The immunogenic composition of any of 1.1 to 1.7, wherein the varicella zoster virus antigen has the sequence of SEQ ID No. 1, SEQ ID No. 2, or SEQ ID No. 9.

1.9. The immunogenic composition of any of 1.1 to 1.7, wherein the varicella zoster virus antigen has the sequence of SEQ ID No. 1.

1.10. The immunogenic composition of any of 1.1 to 1.7, wherein the varicella zoster virus antigen has the sequence of SEQ ID No. 9.

1.11. The immunogenic composition of any of 1.1 to 1.10, further comprising a TLR4 agonist.

1.18. The immunogenic composition according to any of 1.15 to 1.17, wherein the emulsion contains the TLR4 agonist.

1.19. The immunogenic composition according to any of 1.1 to 1.13, further comprising an emulsion.

1.20. The immunogenic composition according to 1.19, wherein the emulsion is an oil-in-water emulsion.

1.21. The immunogenic composition according to any of 1.19 to 1.20, wherein the emulsion contains the compound of Formula I or pharmaceutically acceptable salt thereof.

2.1. A method of increasing cell-mediated immunity in a patient, said method comprising administering to said patient an effective amount of an immunogenic composition comprising a varicella zoster virus antigen and a compound of Formula I:

(I)

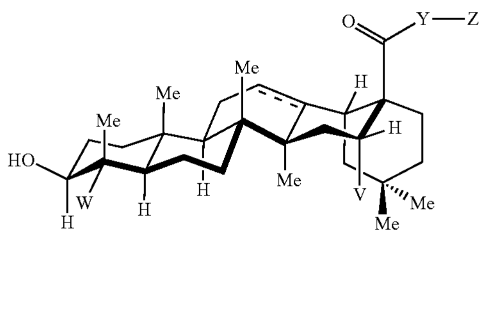

or a pharmaceutically acceptable salt thereof, wherein

--- is a single or double bond;

--- W is —CHO;

V is hydrogen or $OR^x$,

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

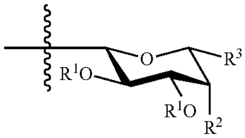

or

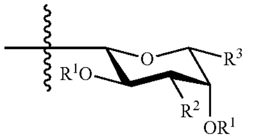

wherein each occurrence of $R^1$ is $R^x$ or a carbohydrate domain having the structure:

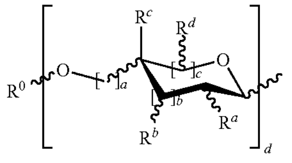

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

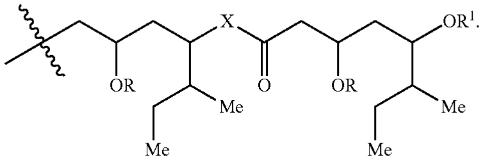

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur, wherein the cell mediated immunity prevents herpes zoster reactivation in the patient.

2.2. The method of 2.1, wherein the compound of Formula I is:

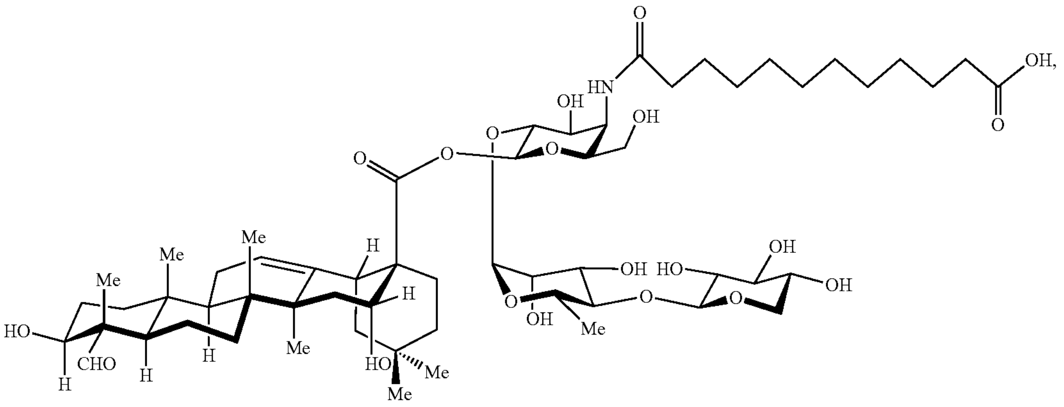

or a pharmaceutically acceptable salt thereof.

2.3. The method of any of 2.1 to 2.2, wherein the compound of Formula I is in free acid form.

2.4. The method of any of 2.1 to 2.2, wherein the compound of Formula I is in choline salt form.

2.5. The method of any of 2.1 to 2.4, wherein the varicella zoster virus antigen is a varicella zoster virus gE antigen truncated to remove the carboxy terminal anchor region.

2.6. The method of any of 2.1 to 2.5, wherein the varicella zoster virus gE antigen is a truncate.

2.7. The method of any of 2.1 to 2.6, wherein the varicella zoster virus gE antigen is a C-terminal truncate.

2.8. The method of any of 2.1 to 2.7, wherein the varicella zoster virus antigen has the sequence of SEQ ID No. 1, SEQ ID No. 2, or SEQ ID No. 9.

2.9. The method of any of 2.1 to 2.7, wherein the varicella zoster virus antigen has the sequence of SEQ ID No. 1.

2.10. The method of any of 2.1 to 2.7, wherein the varicella zoster virus antigen has the sequence of SEQ ID No. 9.

2.11. The method of any of 2.1 to 2.10, further comprising a TLR4 agonist.

2.12. The method of any of 2.1 to 2.11, further comprising a liposome-forming compound.

2.13. The method of 2.12, wherein the liposome-forming compound forms liposomes containing the TLR4 agonist.

2.14. The method of any of 2.12 to 2.13, wherein the liposome-forming compound is selected from the group consisting of DOPC, DMPC, DMPG, cholesterol, and combinations thereof.

2.15. The method according to any of 2.1 to 2.11, further comprising an emulsion.

2.16. The method according to 2.15, wherein the emulsion is an oil-in-water emulsion.

2.17. The method according to any of 2.15 to 2.16, wherein the emulsion contains the compound of Formula I or pharmaceutically acceptable salt thereof.

2.18. The method according to any of 2.15 to 2.17, wherein the emulsion contains the TLR4 agonist.

2.19. The method according to any of 2.1 to 2.13, further comprising an emulsion.

2.20. The method according to 2.19, wherein the emulsion is an oil-in-water emulsion.

2.21. The method according to any of 2.19 to 2.20, wherein the emulsion contains the compound of Formula I or pharmaceutically acceptable salt thereof.

EXAMPLES

Example 1—Liposome PHAD+Compound I-4 Free Acid Form

The impact of TQL-1055 free acid (Compound I-4 free acid) on antibody titers induced by gE antigen was tested. Mice were immunized with gE (5 mcg) alone, gE (5 mcg) with blank liposomes, gE (5 mcg) with liposomes containing PHAD (7.5 mcg), gE (5 mcg) with liposomes containing PHAD (7.5 mcg) and TQL-1055 free acid (four groups: 5 mcg, 15 mcg, 30 mcg, 50 mcg), and gE (5 mcg) with liposomes containing MPL® (7.5 mcg) and QS-21 (5 mcg). Mice were immunized at Day 0 and Day 14. Groups were bled at Day 14 (post Dose 1) and Day 28 (post Dose 2) for serum analysis for anti-gE specific antibody response. The results are shown below.

gE-Specific Total IgG Titers Post Dose 1

FIG. 10 is a graph depicting gE-specific total IgG titers post Dose 1 for the groups described above (Groups 1 to 7). For each group shown in FIG. 10, Tables 1.1 and 1.2 below contain geometric mean titer (GMT) values, 95% confidence intervals (95% CI) for titer values, and adjusted P-values comparing the GMT for Groups 3-6 vs. Group 7.

TABLE 1.1 gE-specific total IgG titers post dose 1

| Group # | Group | GMT | 95% CI | Adjusted P-value (compared to Group 7) |
|---|---|---|---|---|
| 1 | 5 mcg gE alone | N/A: not detected | N/A | — |
| 2 | 5 mcg gE + blank liposome | N/A: not detected | N/A | — |
| 3 | 5 mcg gE + 7.5 mcg liposomal | 17,667 | [12,027; 25,953] | 0.0002 |

TABLE 1.1-continued gE-specific total IgG titers post dose 1

| Group # | Group | GMT | 95% CI | Adjusted P-value (compared to Group 7) |
|---|---|---|---|---|
| | PHAD/5 mcg 1055 | | | |
| 4 | 5 mcg gE + 7.5 mcg liposomal PHAD/15 mcg 1055 | 21,077 | [14,534; 30566] | <0.0001 |
| 5 | 5 mcg gE + 7.5 mcg liposomal PHAD/30 mcg 1055 | 17,457 | [12,117; 25,150] | 0.0002 |
| 6 | 5 mcg gE + 7.5 mcg liposomal PHAD/50 mcg 1055 | 28,885 | [21,778; 38,312] | <0.0001 |
| 7 | 5 mcg gE + 7.5 mcg liposomal MPL + 5 mcg QS21 | 6,519 | [5,176; 8,210] | — |

TABLE 1.2

Group-wise comparisons between groups in Table 1.1

| Comparison (Group vs Group) | GMT | Adjusted P-value |
|---|---|---|
| 3 (5 mcg) vs 4 (15 mcg) | 17,667 vs 21,077 | 0.9135 |
| 3 (5 mcg) vs 5 (30 mcg) | 17,667 vs 17,457 | >0.999 |
| 3 (5 mcg) vs 6 (50 mcg) | 17,667 vs 28,885 | 0.1436 |
| 4 (15 mcg) vs 5 (30 mcg) | 21,077 vs 17,457 | 0.8927 |
| 4 (15 mcg) vs 6 (50 mcg) | 21,077 vs 28,885 | 0.5574 |
| 5 (30 mcg) vs 6 (50 mcg) | 17,457 vs 28,885 | 0.1276 |

Log 10 transformed GMT were compared using One-way ANOVA. Groupwise comparisons were made and p-values adjusted for multiple comparisons with Tukey's post-hoc test. Groups 1 and 2 were excluded from the analysis. Family-wise $\alpha=0.05$.

The data demonstrate post dose 1, Liposomal PHAD+TQL-1055 free acid significantly enhanced gE-specific IgG GMT compared to Group 7 at all TQL-1055 free acid doses. There was a trend for increasing GMT with increasing TQL-1055 free acid dose, however, not statistically significant between any TQL-1055 free acid dose groups.

gE-Specific Total IgG Titers Post Dose 2

Figure 11:
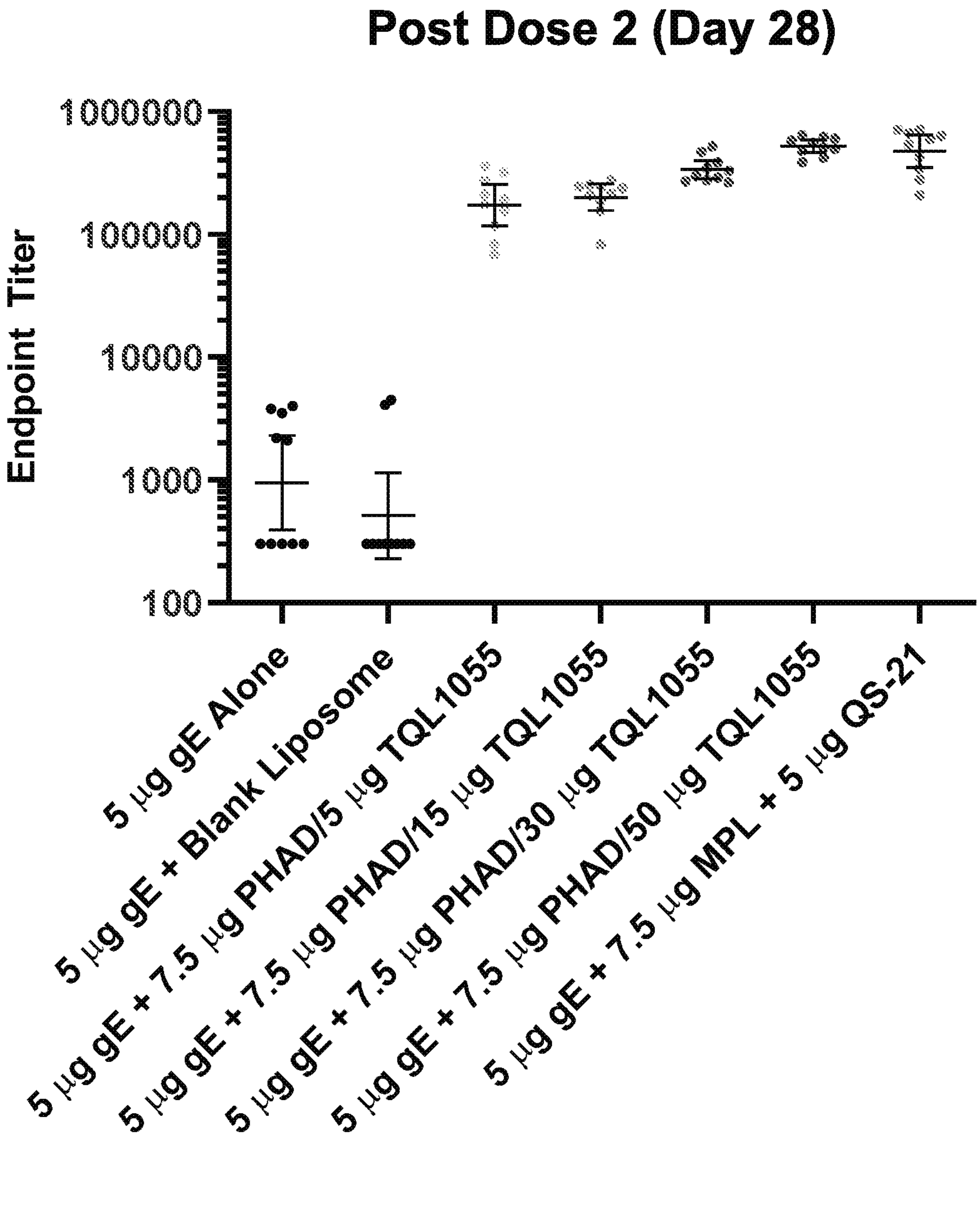
FIG. 11 depicts gE-specific total IgG titer data as explained in Example 1.

FIG. 11 is a graph depicting gE-specific total IgG titers post Dose 2 for the groups described above (Groups 1 to 7). For each group shown in FIG. 11, Tables 1.3 and 1.4 below contain geometric mean titer (GMT) values, 95% confidence intervals (95% CI) for titer values, and adjusted P-values comparing the GMT for Groups 3-6 vs. Group 7.

TABLE 1.3 gE-specific total IgG titers post dose 2

| Group # | Group | GMT | 95% CI | Adjusted P-value (compared to Group 7) |
|---|---|---|---|---|
| 1 | 5 μg gE alone | 949.8 | 393.3; 2293 | — |
| 2 | 5 μg gE + blank liposome | 510.9 | 228.9; 1140 | — |
| 3 | 5 μg gE + 7.5 mcg liposomal PHAD/5 μg 1055 | 173,150 | 117,302; 255,587 | <0.0001 |
| 4 | 5 μg gE + 7.5 mcg liposomal PHAD/15 μg 1055 | 200,974 | 156,245; 258,509 | <0.0001 |

TABLE 1.3-continued gE-specific total IgG titers post dose 2

| Group # | Group | GMT | 95% CI | Adjusted P-value (compared to Group 7) |
|---|---|---|---|---|
| 5 | 5 μg gE + 7.5 mcg liposomal PHAD/30 μg 1055 | 336,323 | 283,817; 398,543 | 0.2442 |
| 6 | 5 μg gE + 7.5 mcg liposomal PHAD/50 μg 1055 | 524,413 | 464,592; 591,936 | 0.9762 |
| 7 | 5 μg gE + 7.5 μg liposomal MPL + 5 μg QS21 | 475,612 | 349,596; 647,051 | — |

TABLE 1.4

Group-wise comparisons between groups in Table 1.3

| Comparison (Group vs Group) | GMT | Adjusted P-value |
|---|---|---|
| 3 (5 μg) vs 4 (15 μg) | 173,150 vs 200,974 | 0.8966 |
| 3 (5 μg) vs 5 (30 μg) | 173,150 vs 336,323 | 0.0021 |
| 3 (5 μg) vs 6 (50 μg) | 173,150 vs 524,413 | <0.0001 |
| 4 (15 μg) vs 5 (30 μg) | 200,974 vs 336,323 | 0.0263 |
| 4 (15 μg) vs 6 (50 μg) | 200,974 vs 524,413 | <0.0001 |
| 5 (30 μg) vs 6 (50 μg) | 336,323 vs 524,413 | 0.0741 |

Log 10 transformed GMT were compared using One-way ANOVA. Groupwise comparisons were made and p-values adjusted for multiple comparisons with Tukey's post-hoc test. Groups 1 and 2 were excluded from the analysis. Family-wise $\alpha=0.05$.

The data demonstrate after dose 2, GMT for all PHAD liposome+1055 groups increased by up to 18-fold compared to post dose 1. Post dose 2, Group 7 resulted in significantly higher GMT compared to PHAD liposomes+TQL-1055 free acid at 5 and 15 mcg doses. GMTs for Group 7 trended higher than PHAD liposomes+TQL-1055 free acid at 30 mcg dose, although not statistically significant. GMT for the 50 mcg TQL-1055 free acid dose trended higher than Group 7, although not statistically significant. There was a trend for increasing GMT with increasing TQL-1055 free acid dose. Increasing the TQL-1055 free acid dose from 5 to 30 mcg and from 15 to 30 mcg significantly increased GMTs.

gE-Specific Total IgG1 Titers Post Dose 1

Figure 12:
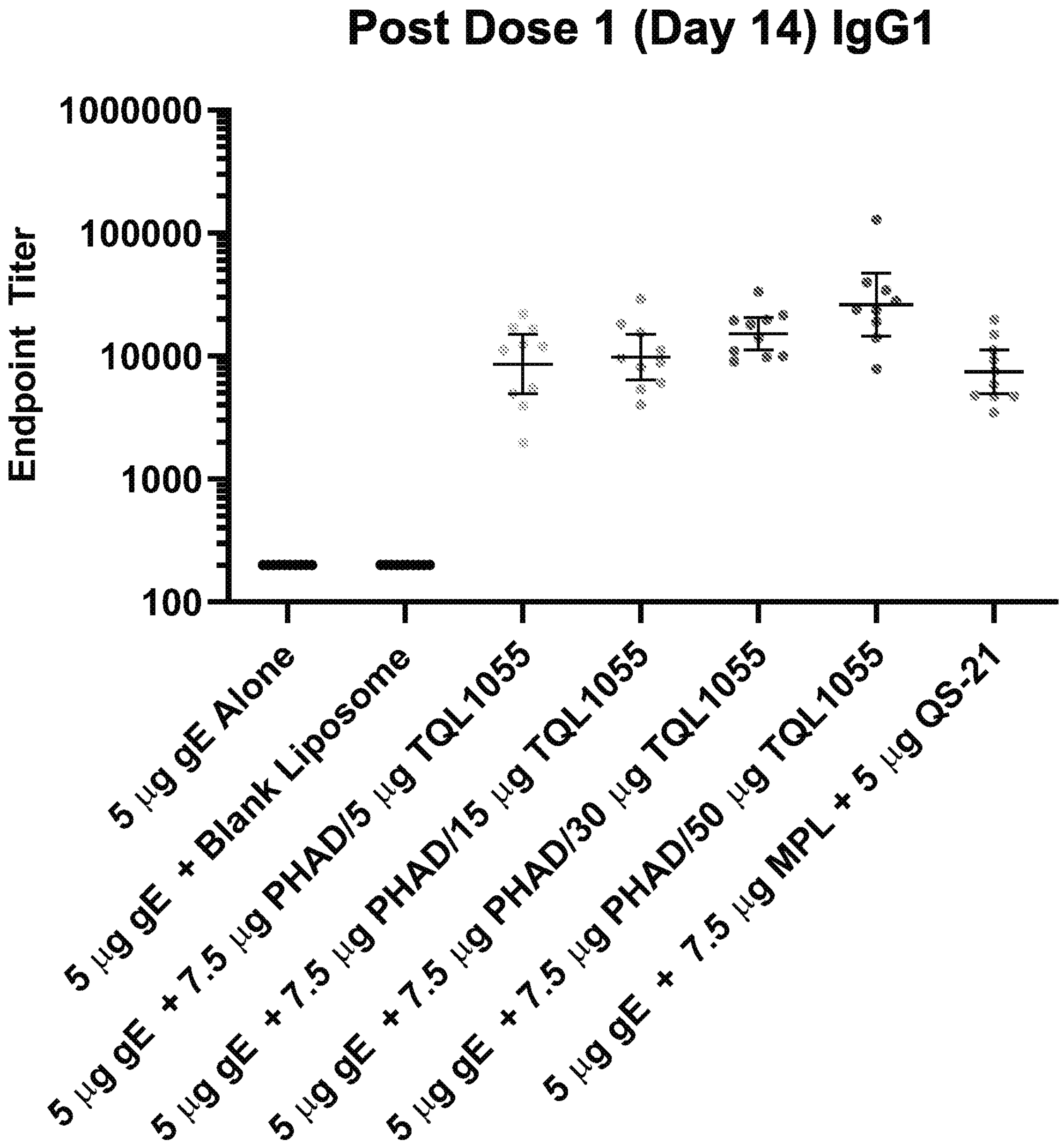
FIG. 12 depicts gE-specific total IgG1 titer data as explained in Example 1.

FIG. 12 is a graph depicting gE-specific total IgG1 titers post Dose 1 for the groups described above (Groups 1 to 7). For each group shown in FIG. 12, Tables 1.5 and 1.6 below contain geometric mean titer (GMT) values, 95% confidence intervals (95% CI) for titer values, and adjusted P-values comparing the GMT for Groups 3-6 vs. Group 7.

TABLE 1.5 gE-specific total IgG1 titers post dose 1

| Group # | Group | GMT | 95% CI | Adjusted P-value (compared to Group 7) |
|---|---|---|---|---|
| 1 | 5 mcg gE alone | Not Detected | N/A | — |
| 2 | 5 mcg gE + blank liposome | Not Detected | N/A | — |
| 3 | 5 mcg gE + 7.5 mcg liposomal PHAD/5 mcg 1055 | 8,591 | 4,943; 14,932 | 0.9854 |

TABLE 1.5-continued

| gE-specific total IgG1 titers post dose 1 | | | | |
|---|---|---|---|---|
| Group # | Group | GMT | 95% CI | Adjusted P-value (compared to Group 7) |
| 4 | 5 mcg gE + 7.5 mcg liposomal PHAD/15 mcg 1055 | 9,801 | 6,379; 15,061 | 0.8641 |
| 5 | 5 mcg gE + 7.5 mcg liposomal PHAD/30 mcg 1055 | 15,240 | 11,211; 20,716 | 0.1038 |
| 6 | 5 mcg gE + 7.5 mcg liposomal PHAD/50 mcg 1055 | 26,180 | 14,493; 47,291 | 0.0008 |
| 7 | 5 mcg gE + 7.5 mcg liposomal MPL + 5 mcg QS21 | 7,416 | 4,935; 11,144 | — |

TABLE 1.6

| Group-wise comparisons between groups in Table 1.5 | | |
|---|---|---|
| Comparison (Group vs Group) | GMT | Adjusted P-value |
| 3 (5 mcg) vs 4 (15 mcg) | 8,591 vs 9,801 | 0.9903 |
| 3 (5 mcg) vs 5 (30 mcg) | 8,591 vs 15,240 | 0.2793 |
| 3 (5 mcg) vs 6 (50 mcg) | 8,591 vs 26,180 | 0.0039 |
| 4 (15 mcg) vs 5 (30 mcg) | 9,801 vs 15,240 | 0.5389 |
| 4 (15 mcg) vs 6 (50 mcg) | 9,801 vs 26,180 | 0.0137 |
| 5 (30 mcg) vs 6 (50 mcg) | 15,240 vs 26,180 | 0.3618 |

Log 10 transformed GMT were compared using One-way ANOVA. Groupwise comparisons were made and p-values adjusted for multiple comparisons with Tukey's post-hoc test. Groups 1 and 2 were excluded from the analysis. Family-wise α=0.05.

The data demonstrate that after dose 1, gE-specific IgG1 GMT trended higher in all groups having PHAD Liposomes+TQL-1055 free acid compared to Group 7. GMT for the 50 mcg TQL-1055 free acid dose was significantly higher compared to Group 7. There was a trend for increasing GMT with increasing TQL-1055 free acid dose. Increasing TQL-1055 free acid dose from 5 or 15 mcg to 50 mcg resulted in significantly higher GMTs.

gE-Specific Total IgG1 Titers Post Dose 2

Figure 13:
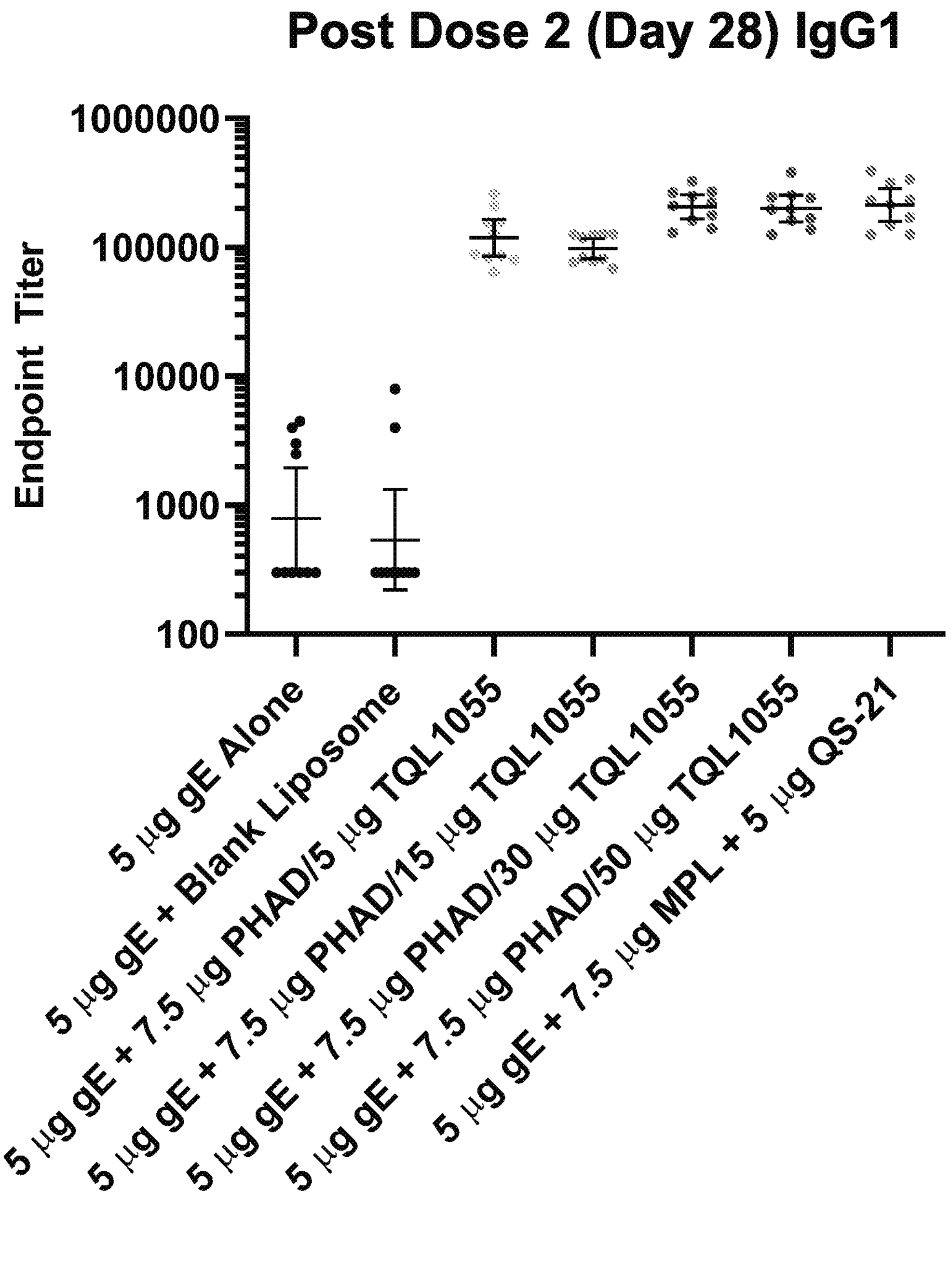
FIG. 13 depicts gE-specific total IgG1 titer data as explained in Example 1.

FIG. 13 is a graph depicting gE-specific total IgG1 titers post Dose 2 for the groups described above (Groups 1 to 7). For each group shown in FIG. 13, Tables 1.7 and 1.8 below contain geometric mean titer (GMT) values, 95% confidence intervals (95% CI) for titer values, and adjusted P-values comparing the GMT for Groups 3-6 vs. Group 7.

TABLE 1.7

| gE-specific total IgG1 titers post dose 2 | | | | |
|---|---|---|---|---|
| Group # | Group | GMT | 95% CI | Adjusted P-value (compared to Group 7) |
| 1 | 5 mcg gE alone | 793.1 | 321; 1,960 | — |
| 2 | 5 mcg gE + blank liposome | 539.8 | 220; 1,319 | — |
| 3 | 5 mcg gE + 7.5 mcg liposomal PHAD/5 mcg 1055 | 118,756 | 85,120; 165,684 | 0.0063 |
| 4 | 5 mcg gE + 7.5 mcg liposomal PHAD/15 mcg 1055 | 97,959 | 81,845; 117,245 | 0.0002 |

TABLE 1.7-continued

| gE-specific total IgG1 titers post dose 2 | | | | |
|---|---|---|---|---|
| Group # | Group | GMT | 95% CI | Adjusted P-value (compared to Group 7) |
| 5 | 5 mcg gE + 7.5 mcg liposomal PHAD/30 mcg 1055 | 206,466 | 166,154; 256,558 | 0.9997 |
| 6 | 5 mcg gE + 7.5 mcg liposomal PHAD/50 mcg 1055 | 200,551 | 158,328; 254,034 | 0.9959 |
| 7 | 5 mcg gE + 7.5 mcg liposomal MPL + 5 mcg QS21 | 212,822 | 158,986; 284,890 | — |

TABLE 1.8

| Group-wise comparisons between groups in Table 1.7 | | |
|---|---|---|
| Comparison (Group vs Group) | GMT | Adjusted P-value |
| 3 (5 mcg) vs 4 (15 mcg) | 118,756 vs 97,959 | 0.7534 |
| 3 (5 mcg) vs 5 (30 mcg) | 118,756 vs 206,466 | 0.0107 |
| 3 (5 mcg) vs 6 (50 mcg) | 118,756 vs 200,551 | 0.0174 |
| 4 (15 mcg) vs 5 (30 mcg) | 97,959 vs 206,466 | 0.0003 |
| 4 (15 mcg) vs 6 (50 mcg) | 97,959 vs 200,551 | 0.0005 |
| 5 (30 mcg) vs 6 (50 mcg) | 206,466 vs 200,551 | 0.9998 |

Log 10 transformed GMT were compared using One-way ANOVA. Groupwise comparisons were made and p-values adjusted for multiple comparisons with Tukey's post-hoc test. Groups 1 and 2 were excluded from the analysis. Family-wise α=0.05.

The data demonstrate after a second dose, IgG1 GMT for all PHAD liposome+TQL-1055 free acid groups increased compared to post dose 1. Post dose 2, Group 7 resulted in significantly higher GMT compared to PHAD liposomes+TQL-1055 free acid at 5 and 15 mcg doses. GMT titers for Group 7 trended higher than PHAD liposomes+30 mcg and 50 mcg TQL-1055 free acid, although not statistically significant. GMTs for the 30 and 50 mcg TQL-1055 free acid dose were significantly higher than both the 5 and 15 mcg 1055 dose.

gE-Specific Total IgG2c Titers Post Dose 1

Figure 14:
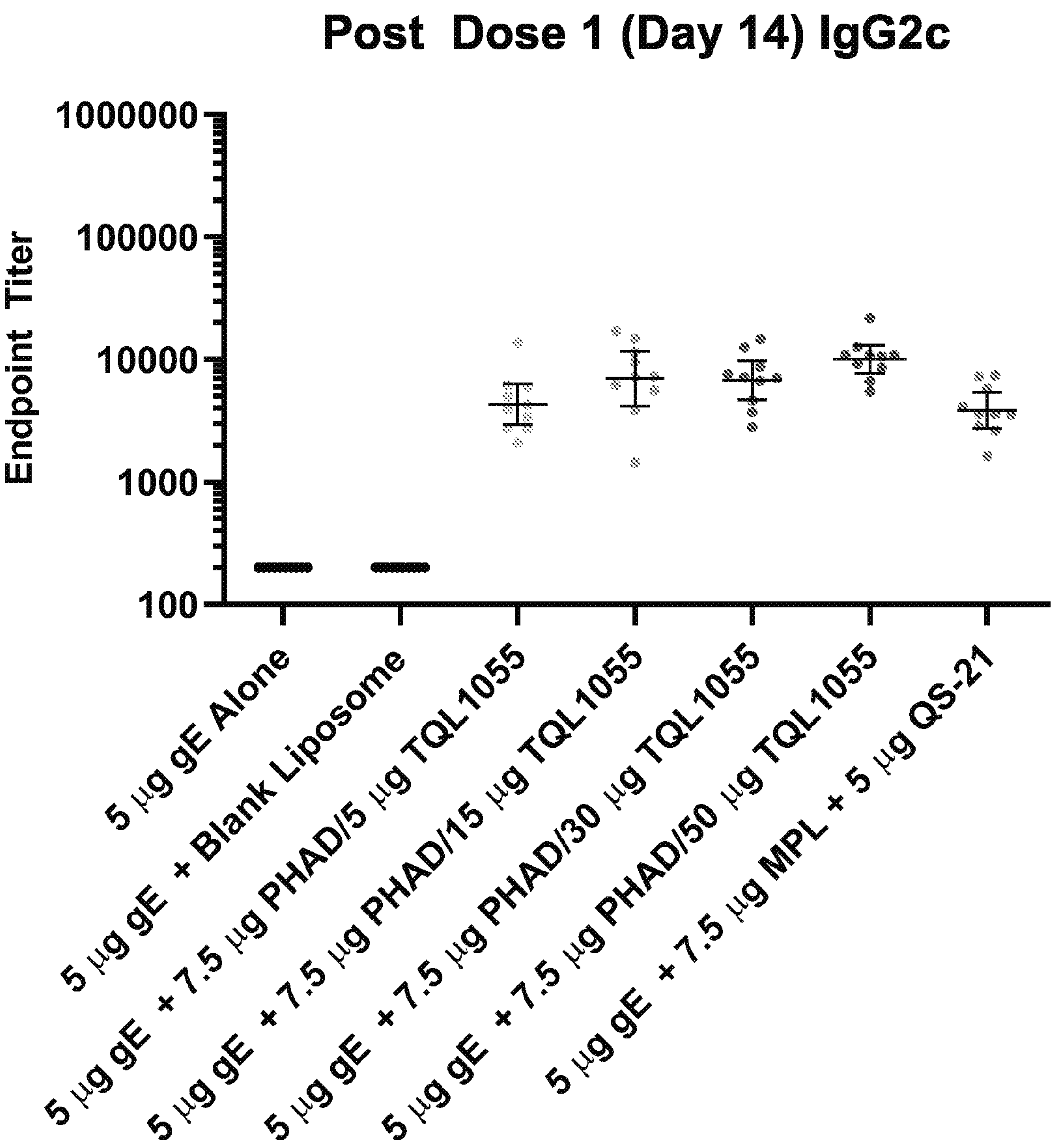
FIG. 14 depicts gE-specific total IgG2c titer data as explained in Example 1.

FIG. 14 is a graph depicting gE-specific total IgG2c titers post Dose 1 for the groups described above (Groups 1 to 7). For each group shown in FIG. 14, Tables 1.9 and 1.10 below contain geometric mean titer (GMT) values, 95% confidence intervals (95% CI) for titer values, and adjusted P-values comparing the GMT for Groups 3-6 vs. Group 7.

TABLE 1.9

| gE-specific total IgG2c titers post dose 1 | | | | |
|---|---|---|---|---|
| Group # | Group | GMT | 95% CI | Adjusted P-value (compared to Group 7) |
| 1 | 5 mcg gE alone | Not Detected | N/A | — |
| 2 | 5 mcg gE + blank liposome | Not Detected | N/A | — |
| 3 | 5 mcg gE + 7.5 mcg liposomal PHAD/5 mcg 1055 | 4,313 | 2,943; 6,321 | 0.9892 |
| 4 | 5 mcg gE + 7.5 mcg liposomal PHAD/15 mcg 1055 | 7,010 | 4,197; 11,706 | 0.1058 |

TABLE 1.9-continued gE-specific total IgG2c titers post dose 1

| Group # | Group | GMT | 95% CI | Adjusted P-value (compared to Group 7) |
|---|---|---|---|---|
| 5 | 5 mcg gE + 7.5 mcg liposomal PHAD/30 mcg 1055 | 6,762 | 4,694; 9,738 | 0.1448 |
| 6 | 5 mcg gE + 7.5 mcg liposomal PHAD/50 mcg 1055 | 10,072 | 7,714; 13,150 | 0.0019 |
| 7 | 5 mcg gE + 7.5 mcg liposomal MPL + 5 mcg QS21 | 3,851 | 2,750; 5,393 | — |

TABLE 1.10

Group-wise comparisons between groups in Table 1.9

| Comparison (Group vs Group) | GMT | Adjusted P-value |
|---|---|---|
| 3 (5 mcg) vs 4 (15 mcg) | 4,313 vs 7,010 | 0.2652 |
| 3 (5 mcg) vs 5 (30 mcg) | 4,313 vs 6,762 | 0.3390 |
| 3 (5 mcg) vs 6 (50 mcg) | 4,313 vs 10,072 | 0.0076 |
| 4 (15 mcg) vs 5 (30 mcg) | 7,010 vs 6,762 | 0.9999 |
| 4 (15 mcg) vs 6 (50 mcg) | 7,010 vs 10,072 | 0.5548 |
| 5 (30 mcg) vs 6 (50 mcg) | 6,762 vs 10,072 | 0.4614 |

Log 10 transformed GMT were compared using One-way ANOVA. Groupwise comparisons were made and p-values adjusted for multiple comparisons with Tukey's post-hoc test. Groups 1 and 2 were excluded from the analysis. Family-wise $\alpha$=0.05.

The data demonstrate post dose 1, gE-specific IgG2c GMT for PHAD Liposomes+TQL-1055 free acid groups trended higher compared to Group 7. GMT for the 50 mcg TQL-1055 free acid dose were significantly higher compared to Group 7. There was a trend for increasing GMT with increasing TQL-1055 free acid dose. Increasing TQL-1055 free acid dose from 5 to 50 mcg resulted in significantly higher GMTs.

gE-Specific Total IgG2c Titers Post Dose 2

Figure 15:
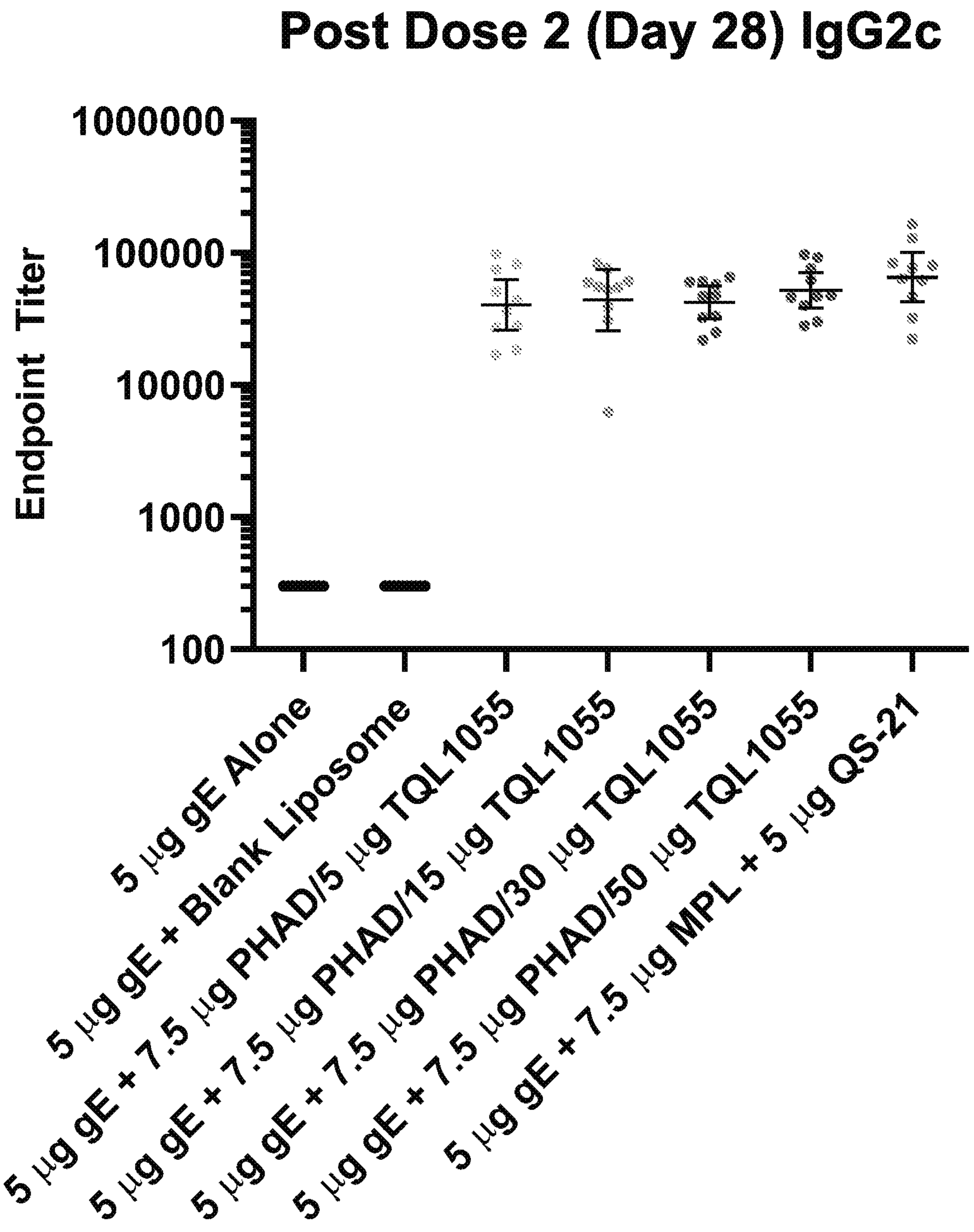
FIG. 15 depicts gE-specific total IgG2c titer data as explained in Example 1.

FIG. 15 is a graph depicting gE-specific total IgG2c titers post Dose 2 for the groups described above (Groups 1 to 7). For each group shown in FIG. 15, Tables 1.11 and 1.12 below contain geometric mean titer (GMT) values, 95% confidence intervals (95% CI) for titer values, and adjusted P-values comparing the GMT for Groups 3-6 vs. Group 7.

TABLE 1.11 gE-specific total IgG2c titers post dose 2

| Group # | Group | GMT | 95% CI | Adjusted P-value (compared to Group 7) |
|---|---|---|---|---|
| 1 | 5 mcg gE alone | Not Detected | N/A | — |
| 2 | 5 mcg gE + blank liposome | Not Detected | N/A | — |
| 3 | 5 mcg gE + 7.5 mcg liposomal PHAD/5 mcg 1055 | 40,409 | 26,051; 62,679 | 0.3380 |
| 4 | 5 mcg gE + 7.5 mcg liposomal PHAD/15 mcg 1055 | 44,104 | 25,874; 75,181 | 0.5384 |
| 5 | 5 mcg gE + 7.5 mcg liposomal PHAD/30 mcg 1055 | 42,295 | 31,856; 56,154 | 0.4380 |

TABLE 1.11-continued gE-specific total IgG2c titers post dose 2

| Group # | Group | GMT | 95% CI | Adjusted P-value (compared to Group 7) |
|---|---|---|---|---|
| 6 | 5 mcg gE + 7.5 mcg liposomal PHAD/50 mcg 1055 | 52,170 | 38,323; 71,020 | 0.8990 |
| 7 | 5 mcg gE + 7.5 mcg liposomal MPL + 5 mcg QS21 | 65,517 | 42,621; 100,715 | — |

TABLE 1.12

Group-wise comparisons between groups in Table 1.11

| Comparison (Group vs Group) | GMT | Adjusted P-value |
|---|---|---|
| 3 (5 mcg) vs 4 (15 mcg) | 40,409 vs 44,104 | 0.9969 |
| 3 (5 mcg) vs 5 (30 mcg) | 40,409 vs 42,295 | 0.9998 |
| 3 (5 mcg) vs 6 (50 mcg) | 40,409 vs 52,170 | 0.8547 |
| 4 (15 mcg) vs 5 (30 mcg) | 44,104 vs 42,295 | 0.9998 |
| 4 (15 mcg) vs 6 (50 mcg) | 44,104 vs 52,170 | 0.9645 |
| 5 (30 mcg) vs 6 (50 mcg) | 42,295 vs 52,170 | 0.9230 |

Log 10 transformed GMT were compared using One-way ANOVA. Groupwise comparisons were made and p-values adjusted for multiple comparisons with Tukey's post-hoc test. Groups 1 and 2 were excluded from the analysis. Family-wise $\alpha$=0.05.

The data demonstrate after a second dose, IgG2c GMT for all PHAD liposome+TQL-1055 free acid groups increased compared to post dose 1. Post dose 2, Group 7 IgG2c GMT trended higher compared to PHAD liposomes+TQL-1055 free acid at all doses of TQL-1055 free acid, although not statistically significant. IgG2c GMT for the 50 mcg TQL-1055 free acid dose trended slightly higher compared to lower TQL-1055 free acid doses.

Example 2—Liposome PHAD+Compound I-4 Choline Salt Form

The impact of TQL-1055 choline salt (Compound I-4 choline salt) on antibody titers induced by gE antigen was tested. Mice were immunized with gE (5 mcg) alone, gE (5 mcg) with liposomes containing PHAD (5 mcg), gE (5 mcg) with liposomes containing PHAD (5 mcg) and TQL-1055 choline salt (five groups: 5 mcg, 10 mcg, 20 mcg, 40 mcg, 80 mcg), and gE (5 mcg) with TQL-1055 choline salt (five groups: 5 mcg, 10 mcg, 20 mcg, 40 mcg, 80 mcg). Mice were immunized at Day 0 and Day 14. Groups were bled at Day 13 (post Dose 1) and Day 28 (post Dose 2) for serum analysis. The results are shown below.

Anti-gE IgG Endpoint Titers Post Dose 1

Figure 16:
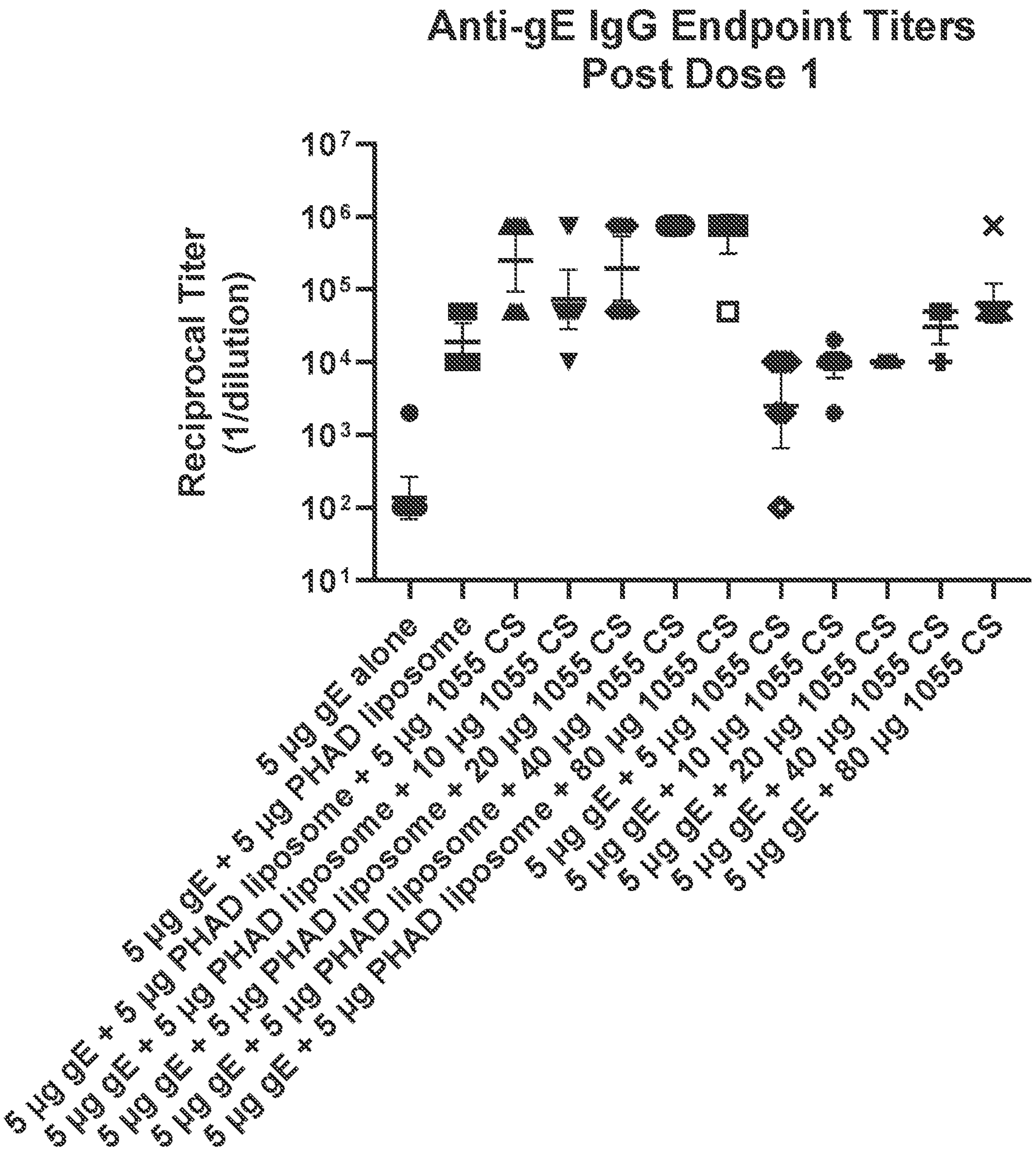
FIG. 16 depicts gE-specific total IgG titer data as explained in Example 2.
Figure 17A:
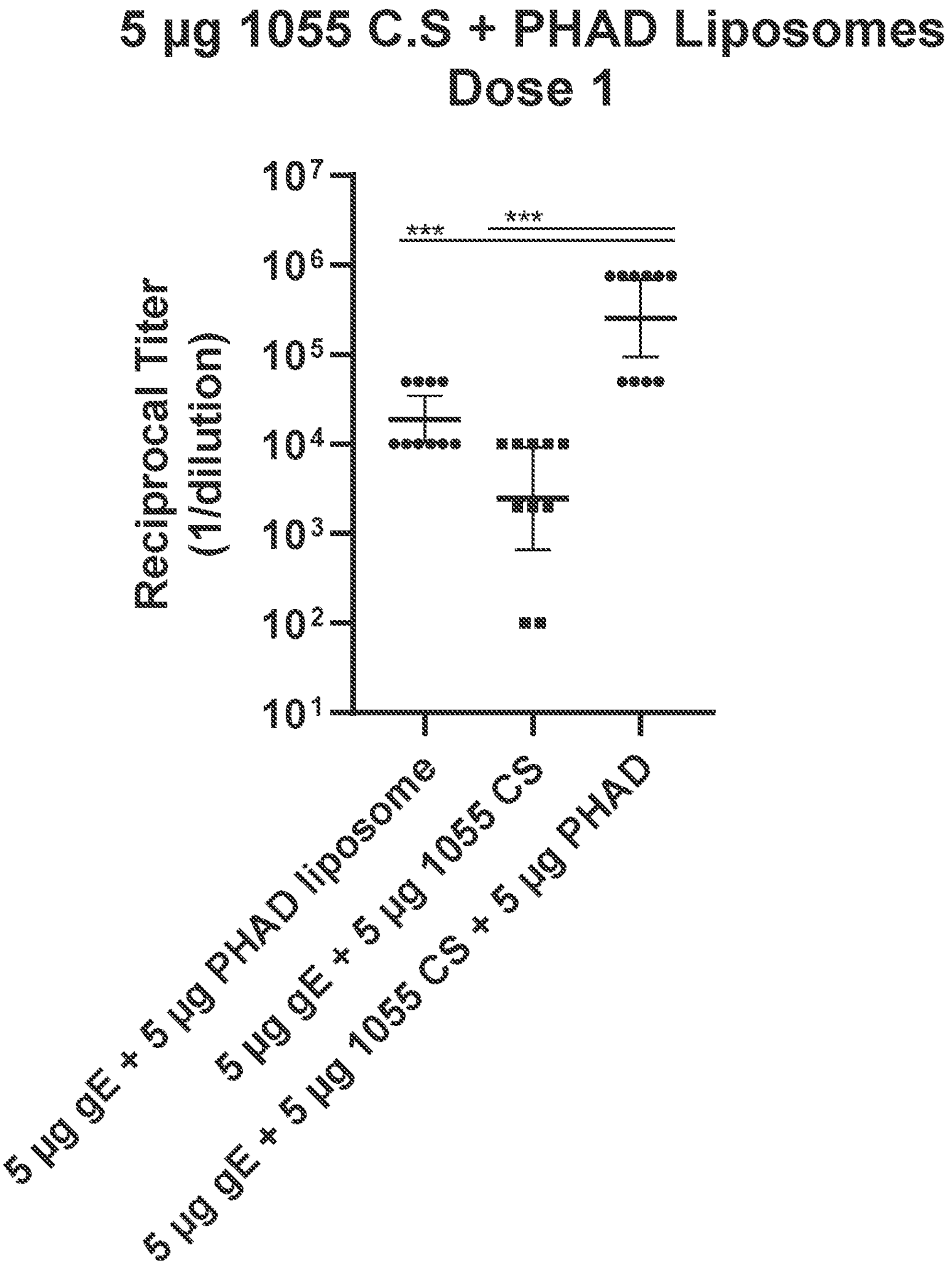
FIGS. 17A-E depict gE-specific total IgG titer data as explained in Example 2.
Figure 17B:
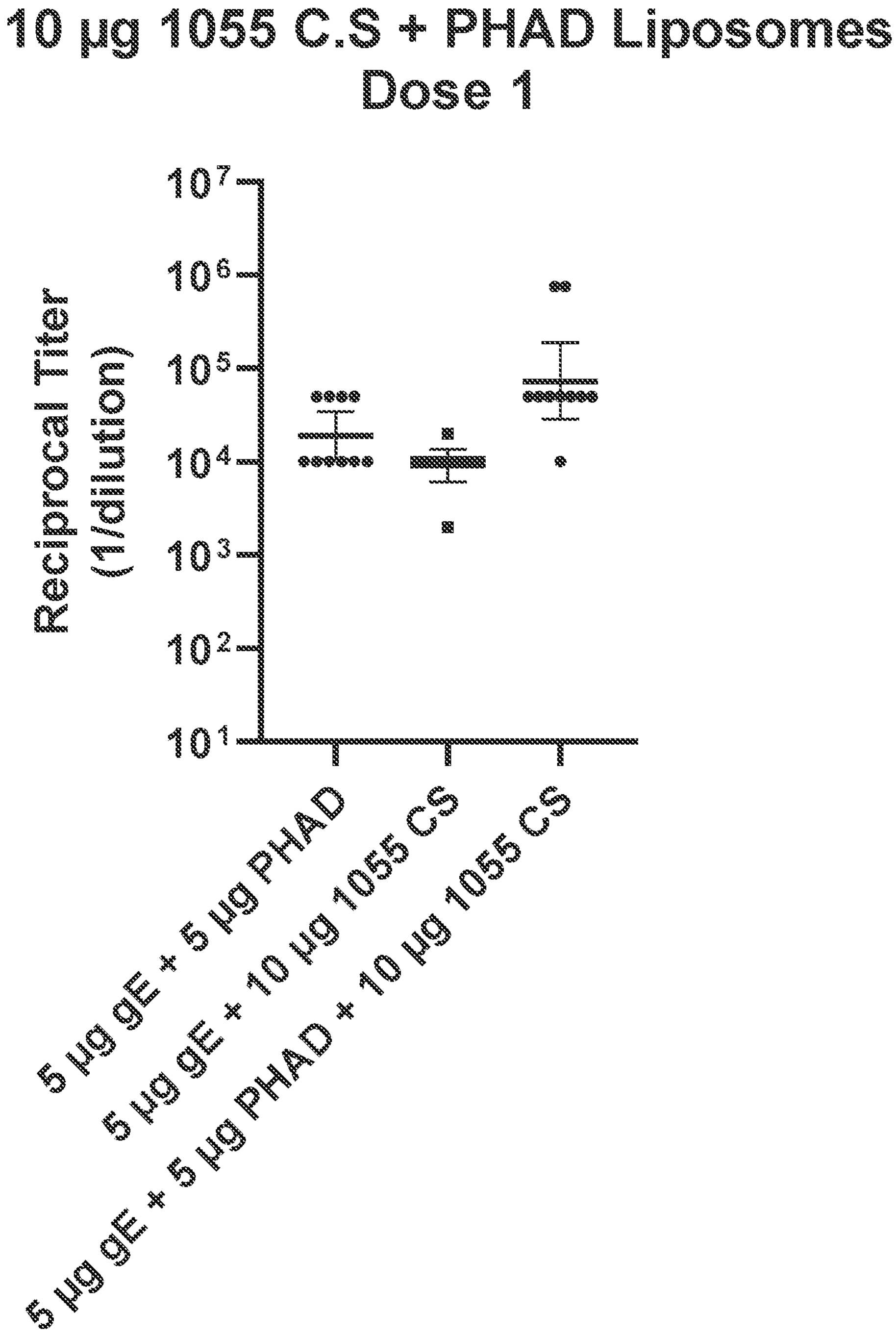
Figure 17C:
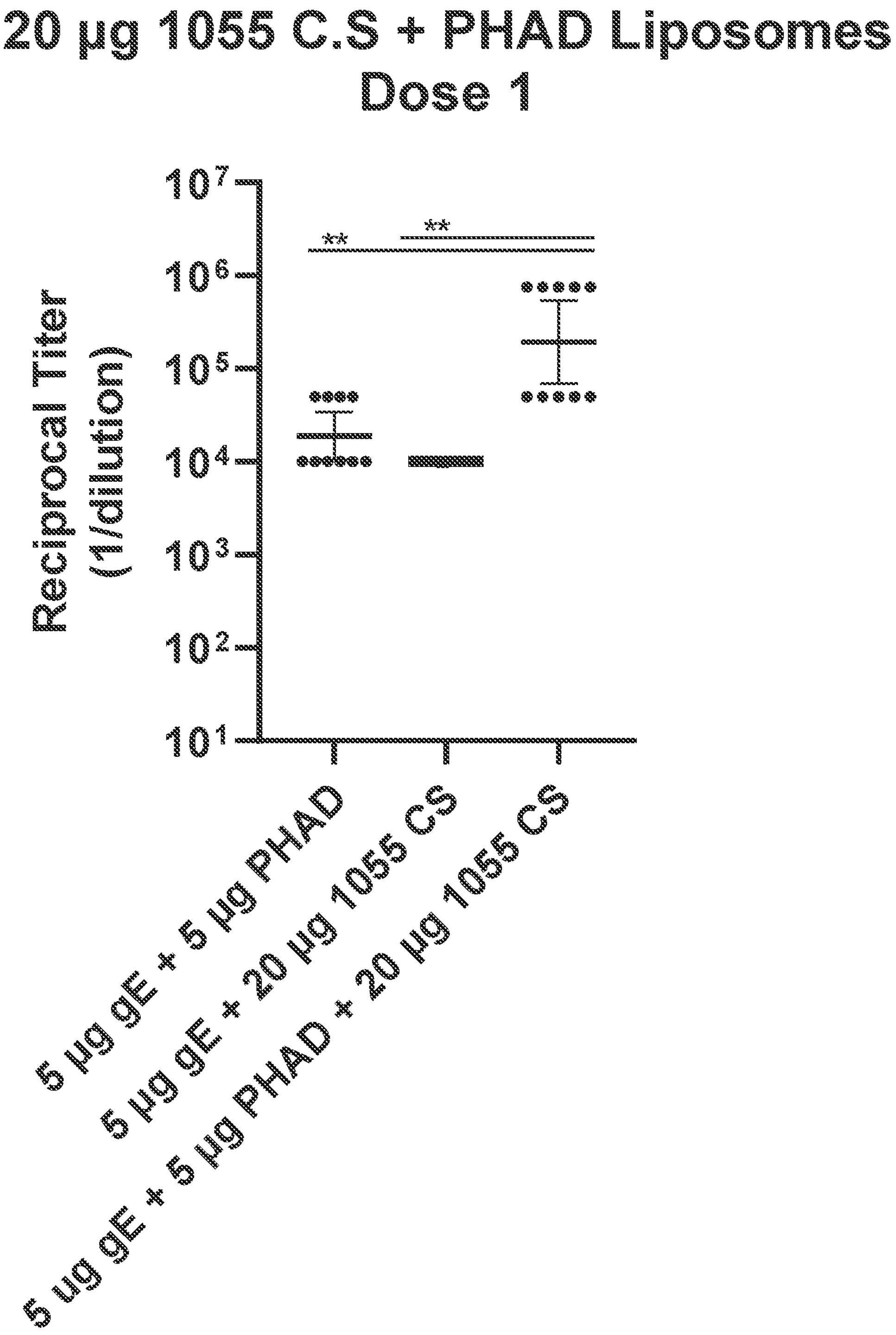
Figure 17D:
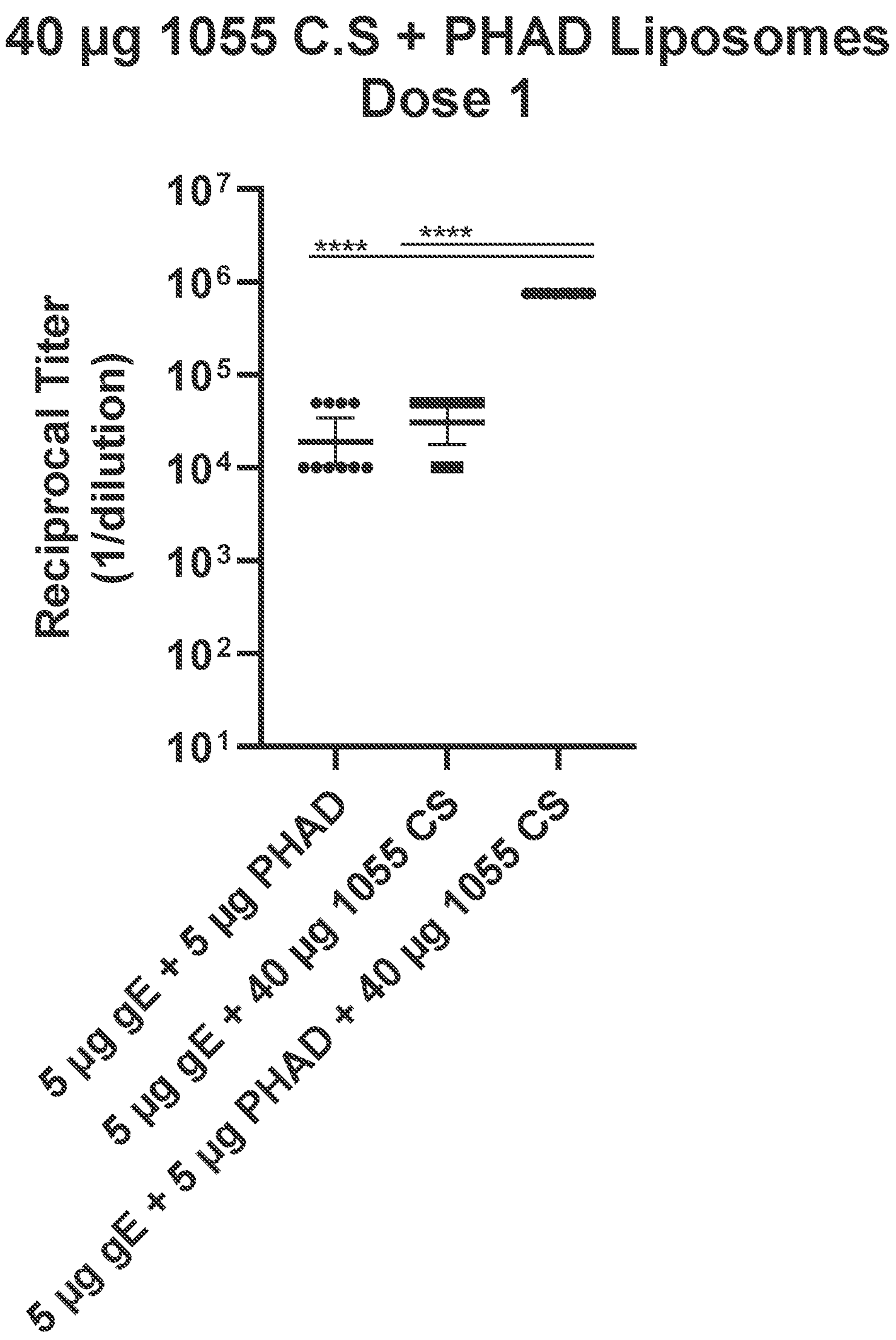
Figure 17E:
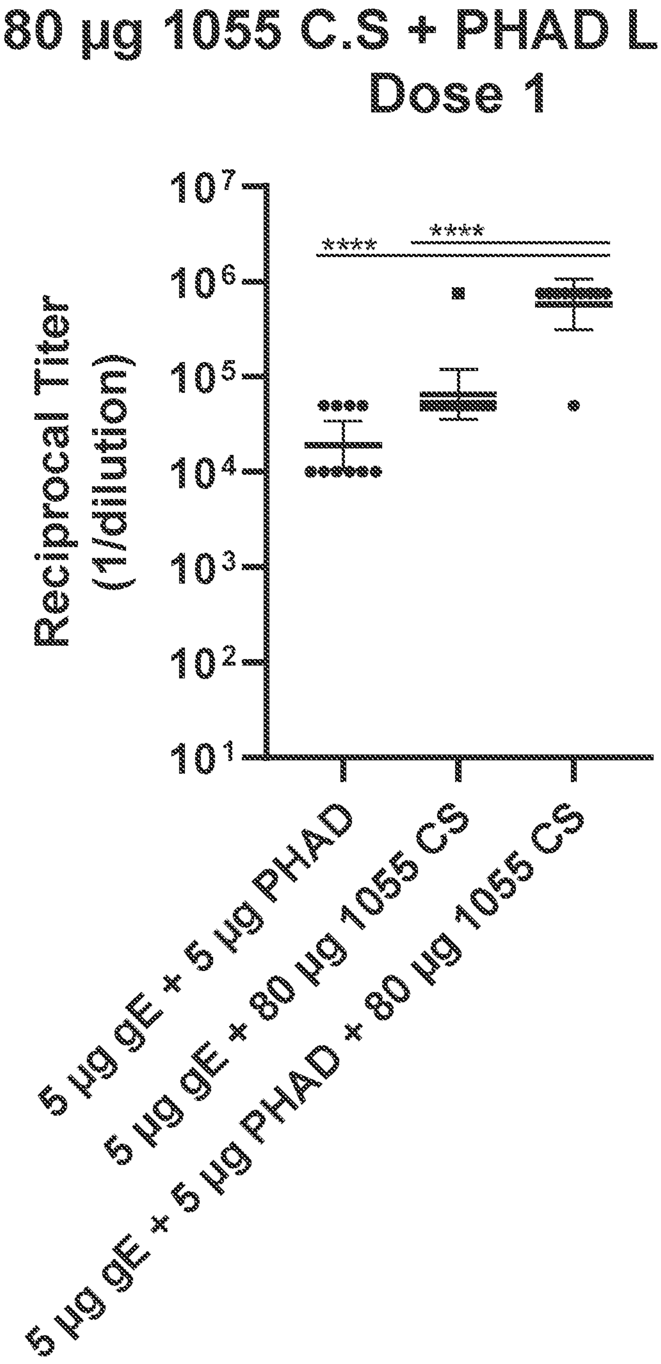

FIG. 16 is a graph depicting gE-specific total IgG titers post Dose 1 for the groups described above. FIGS. 17A-E depict subsets of the data shown in FIG. 16, in which the synergistic effects of PHAD and TQL-1055 choline salt become apparent. For groups shown in FIG. 16, Table 2.1 below contains geometric mean titer (GMT) values and adjusted P-values comparing various groups.

TABLE 2.1

| gE-specific total IgG titers post dose 1 | | | | | | | | |
|---|---|---|---|---|---|---|---|---|
| | Day 13 Anti-gE GMT titer | | Day 13 Comparison | | Day 28 Anti-gE GMT titer | | Day 28 Comparison | |
| | without PHAD liposomes | 5 mcg PHAD in liposomes | Stat Combo vs PHAD alone | Stats Combo vs CS alone | without PHAD liposomes | 5 mcg PHAD in liposomes | Stat Combo vs PHAD alone | Stats Combo vs CS alone |
| 5 mcg gE | 135 | 19,037 | Not statistically significant | Not statistically significant | 12,311 | 689,865 | Not statistically significant | (40: p = 0.025) (80: p < 0.0001) |
| 5 mcg gE + 5 mcg 1055 CS | 2,456 | 253,878 | P = 0.0006 | P = 0.0002 | 61,703 | 2,128,350 | P = 0.0005 | P < 0.0001 |
| 5 mcg gE + 10 mcg 1055 CS | 9,124 | 73,163 | P = 0.9423 | P = 0.8836 | 425,670 | 1,313,264 | P = 0.319 | P < 0.0001 |
| 5 mcg gE + 20 mcg 1055 CS | 10,000 | 193,649 | P = 0.0099 | P = 0.0054 | 500,000 | 1,811,949 | P = 0.0066 | P = 0.04 |
| 5 mcg gE + 40 mcg 1055 CS | 30,852 | 750,022 | P < 0.0001 | P < 0.0001 | 810,328 | 2,128,350 | P = 0.0005 | P < 0.0001 |
| 5 mcg gE + 80 mcg 1055 CS | 65,561 | 572,074 | P < 0.0001 | P < 0.0001 | 2,128,350 | >2,500,000 | P < 0.0001 | P = 0.0066 |
| +6 h 5 mcg gE + 5 mcg 1055 CS | 2,091 | 85,939 | vs T = 0 Not statistically significant | | 117,462 | 1,313,264 | vs T = 0 Not statistically significant | |
| +6 h 5 mcg gE + 80 mcg 1055 CS | 332,839 | 572,074 | vs T = 0 with PHAD: Not statistically significant Without PHAD: P = 0.0016 | | 1,811,949 | 2,128,350 | vs T = 0 Not statistically significant | |

The data demonstrate after the first dose, gE-specific IgG for TQL-1055 choline salt+PHAD in liposome exhibits as synergistic effect as compared to either compound alone. When considered together with data from Example 1, there is a trend to higher titers in groups including TQL-1055 choline salt as compared to groups including TQL-1055 free acid.

Anti-gE IgG Endpoint Titers Post Dose 2

Figure 18:
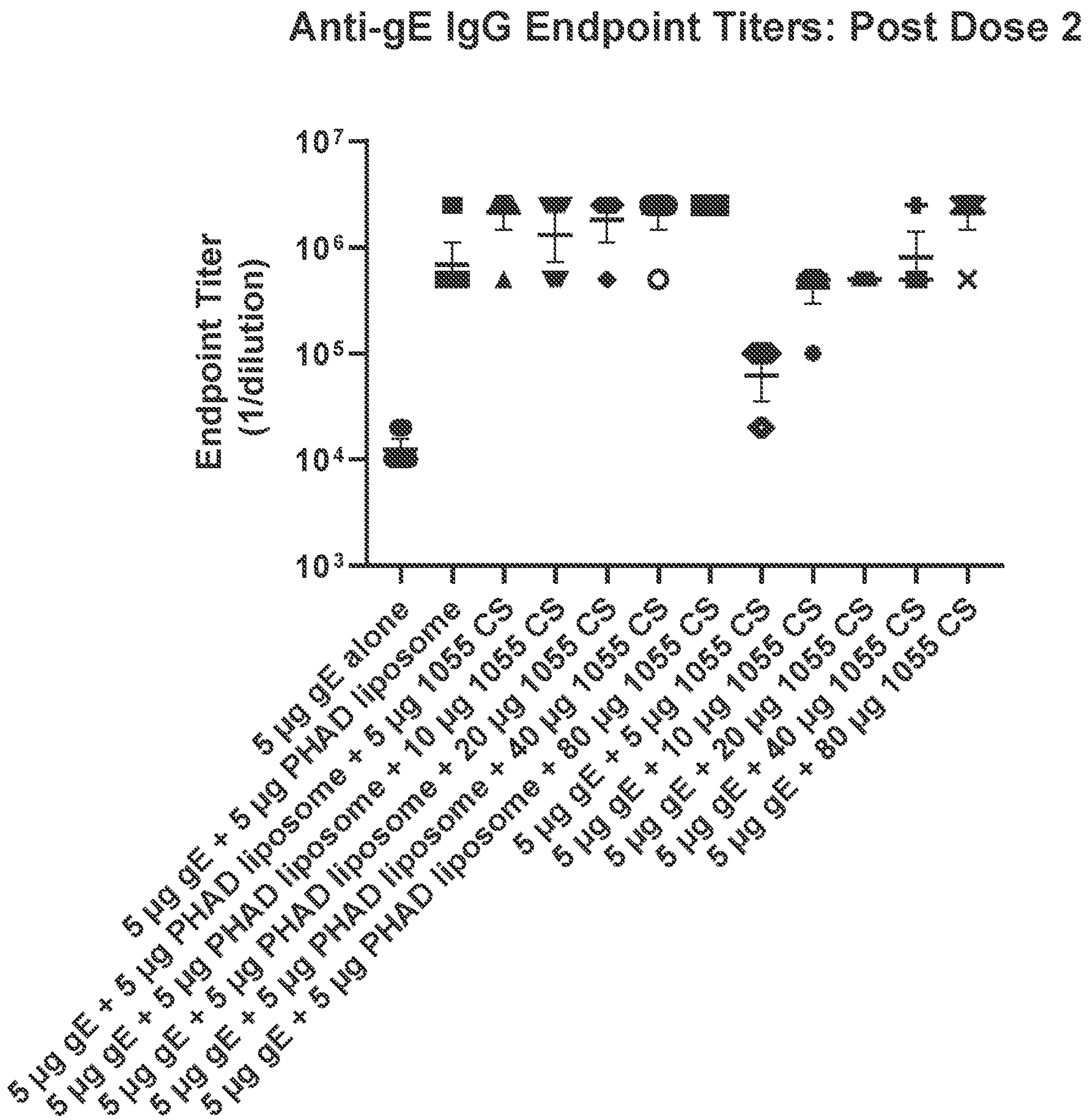
FIG. 18 depicts gE-specific total IgG titer data as explained in Example 2.
Figure 19A:
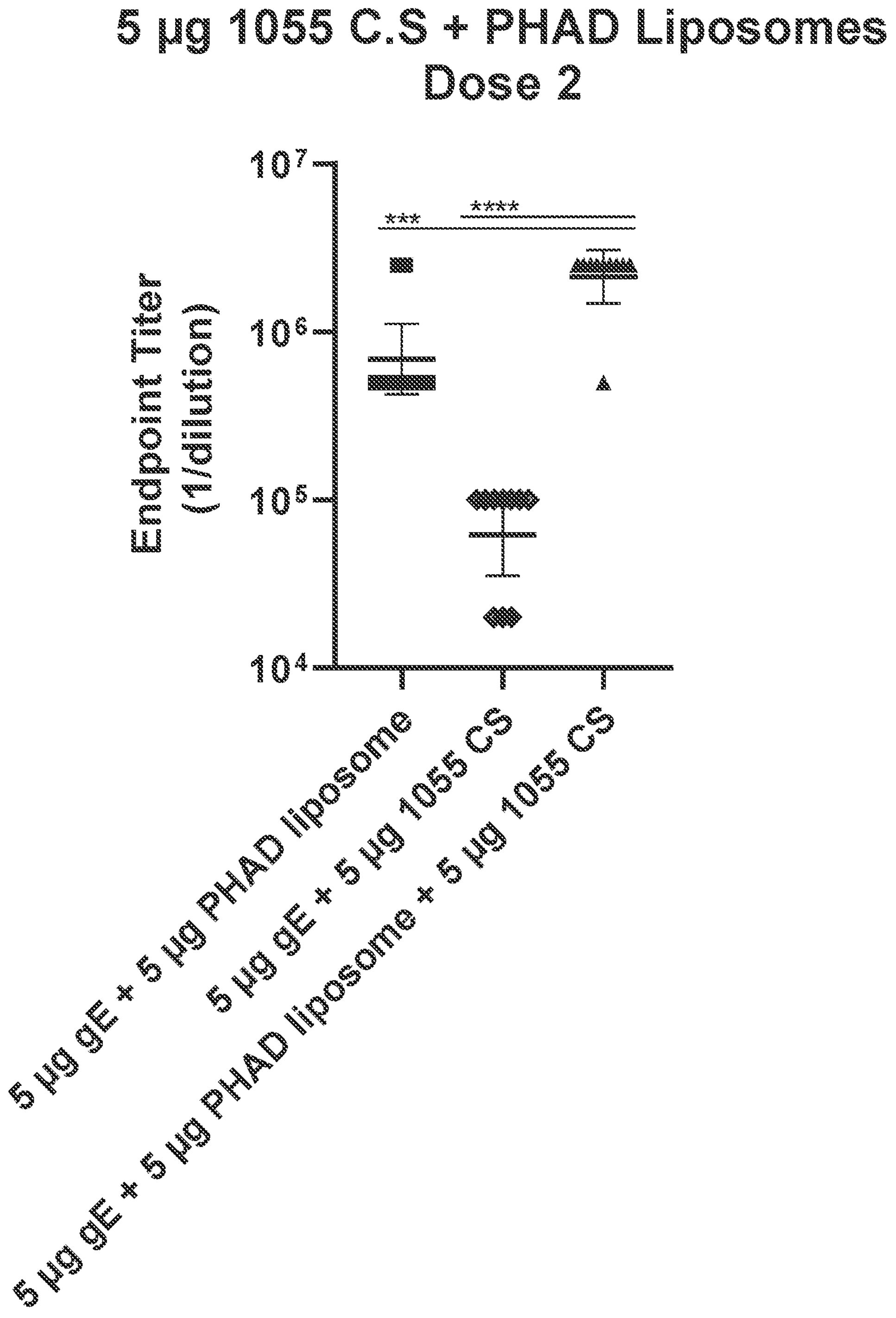
FIGS. 19A-E depict gE-specific total IgG titer data as explained in Example 2.
Figure 19B:
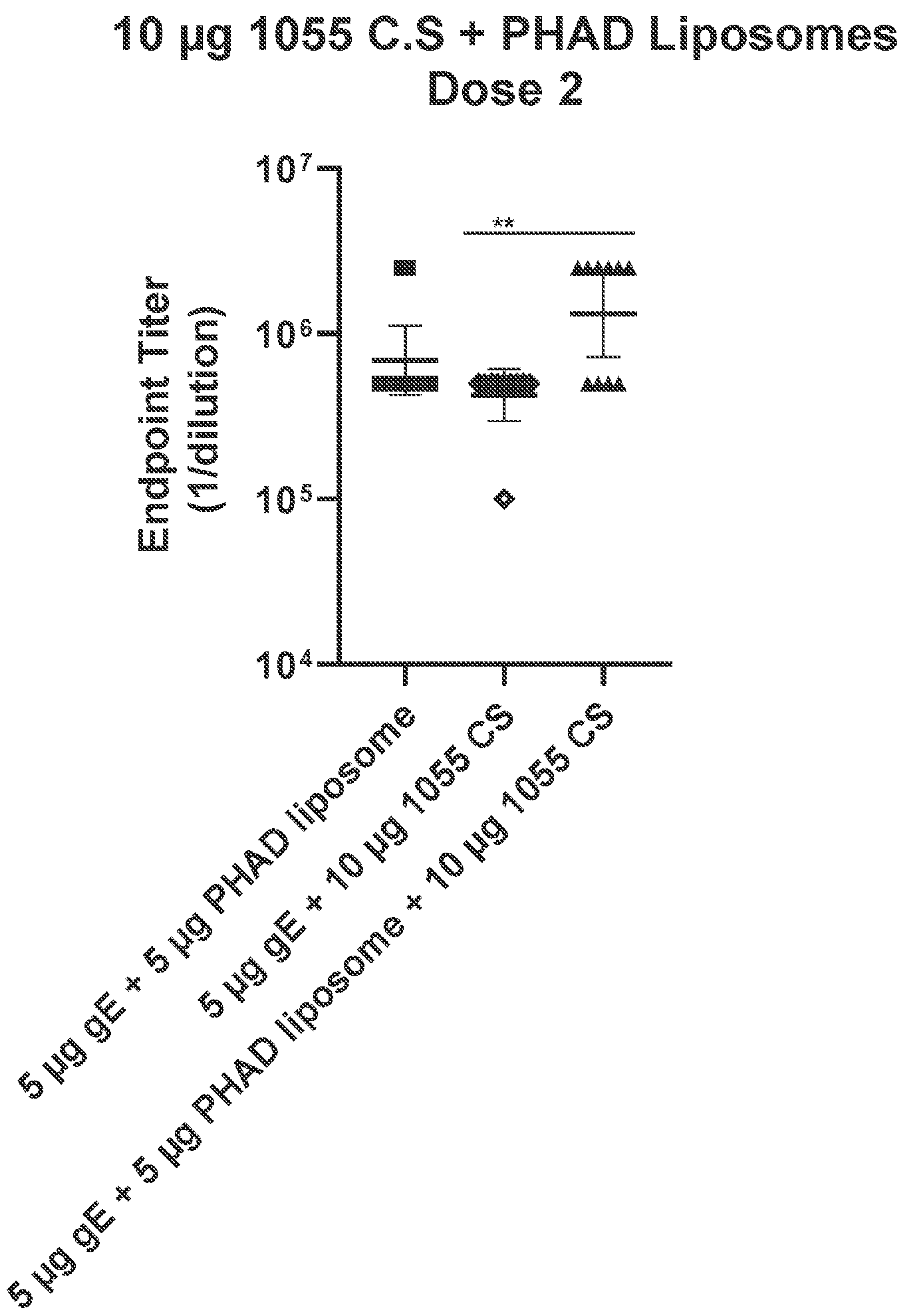
Figure 19C:
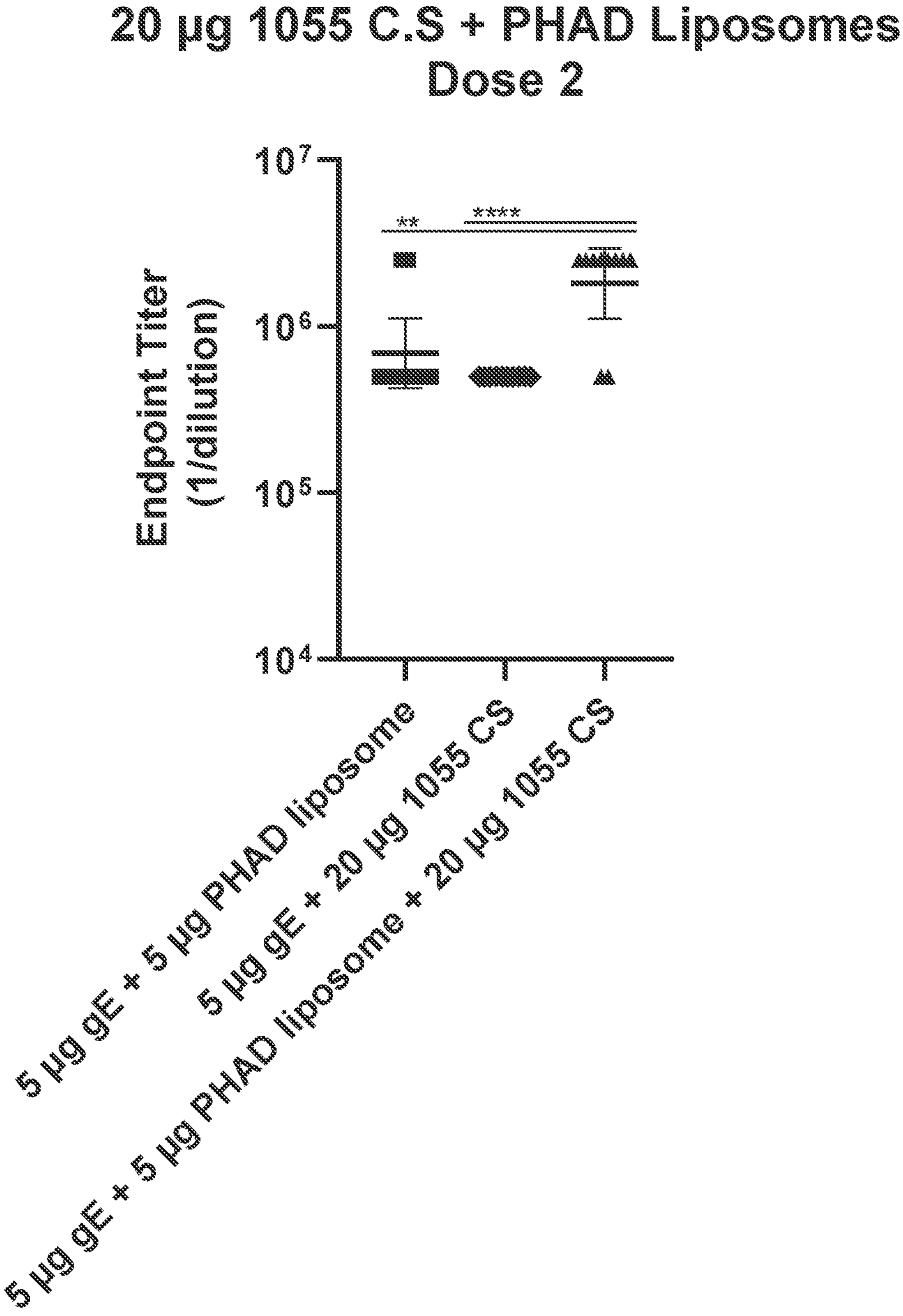
Figure 19D:
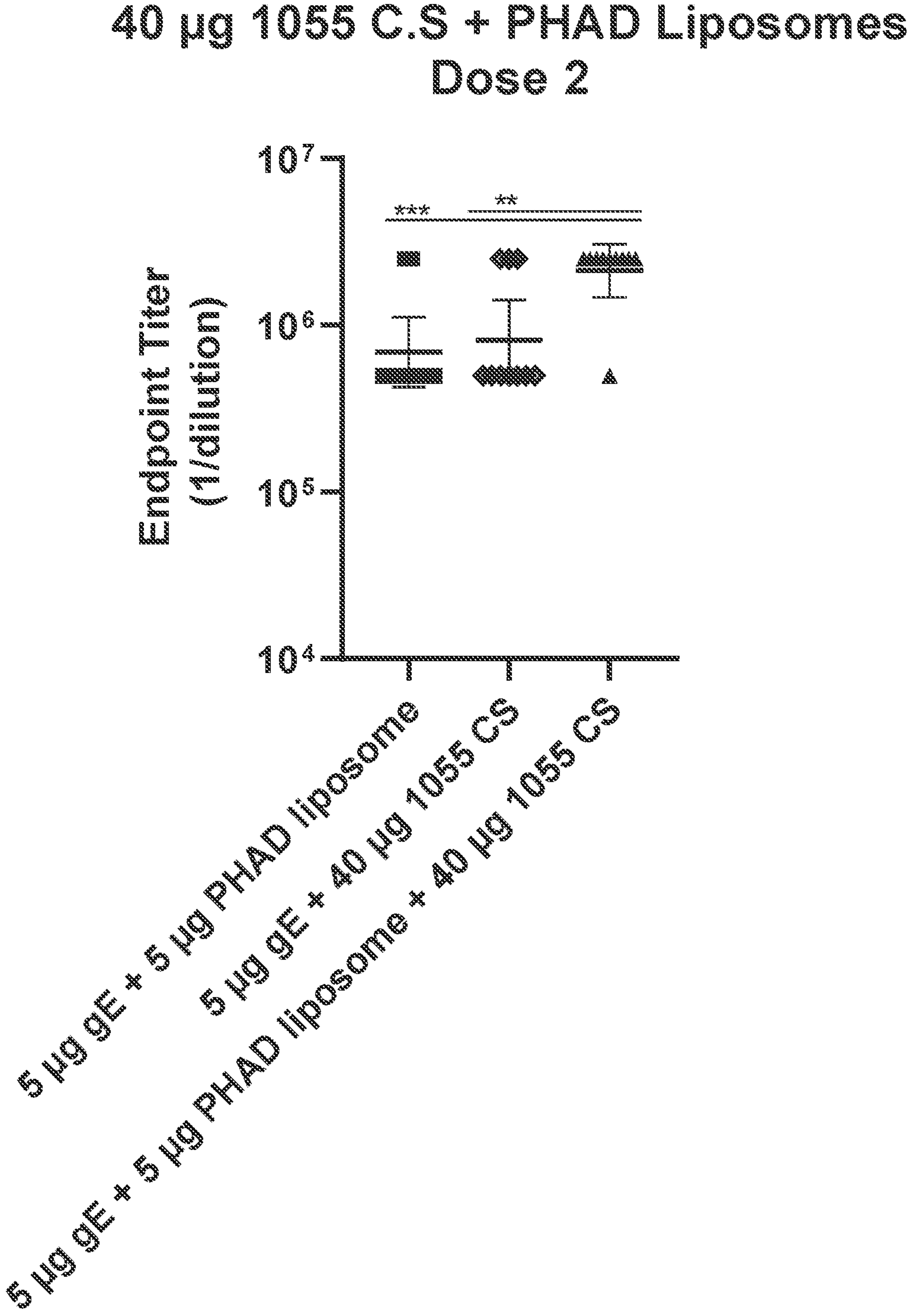
Figure 19E:
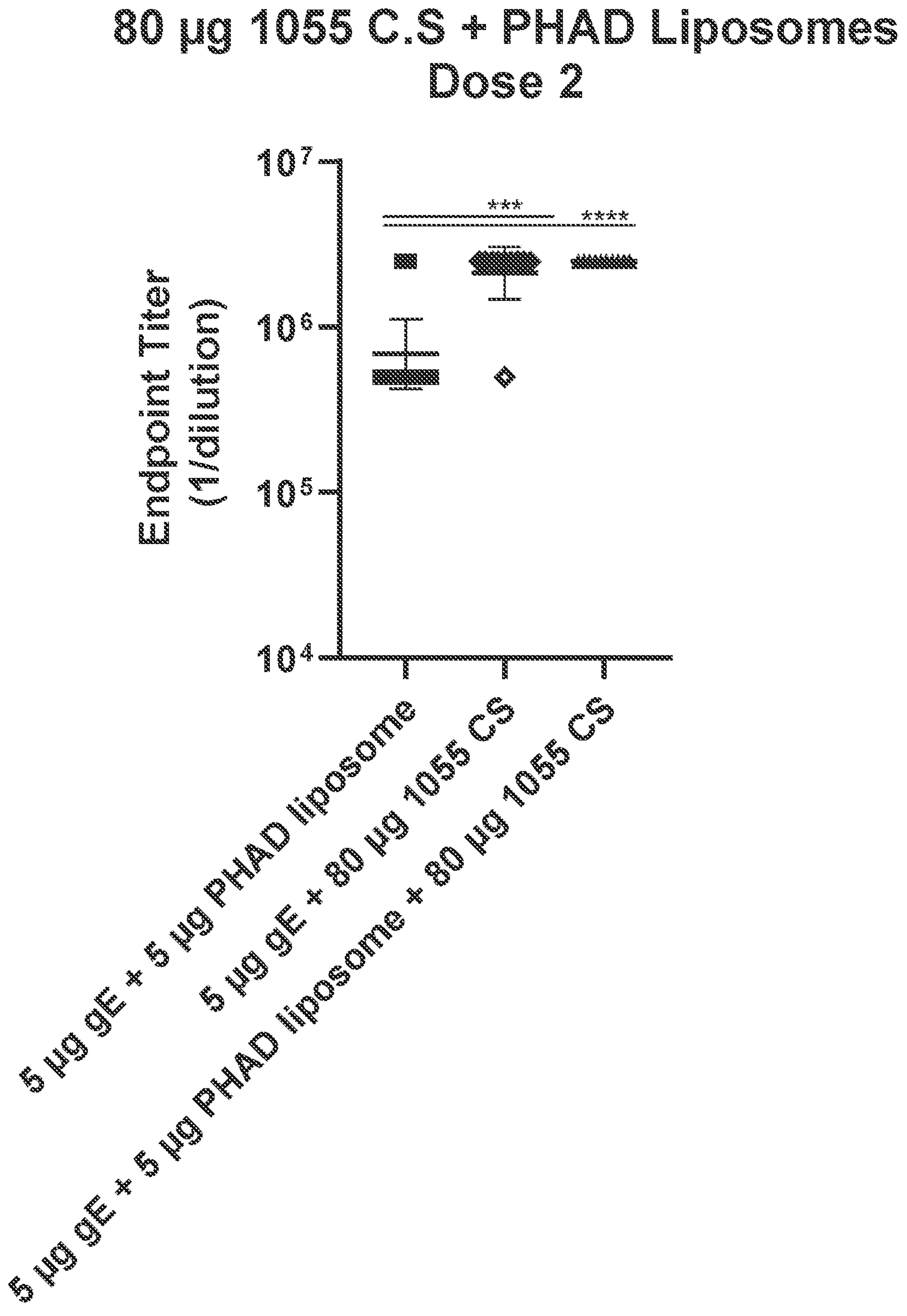

FIG. 18 is a graph depicting gE-specific total IgG titers post Dose 2 for the groups described above. FIGS. 19A-E depict subsets of the data shown in FIG. 18, in which the synergistic effects of PHAD and TQL-1055 choline salt once again become apparent. For groups shown in FIG. 16, Table 2.1 above contains geometric mean titer (GMT) values and adjusted P-values comparing various groups.

The data demonstrate after the second dose, gE-specific IgG for TQL-1055 choline salt+PHAD in liposome exhibits as synergistic effect as compared to either compound alone. When considered together with data from Example 1, there is a trend to higher titers in groups including TQL-1055 choline salt as compared to groups including TQL-1055 free acid.

Example 3—Oil in Water Emulsions+Compound I-4 Choline Salt Form

The impact of an oil-in-water emulsion containing TQL-1055 free acid (Compound I-4 free acid), TQL-1055 choline salt (Compound I-4 choline salt), PHAD liposomes, and combinations thereof on antibody titers induced by gE antigen was tested. Mice were immunized with PBS alone, gE (5 mcg) alone, gE (5 mcg) in an oil-in-water emulsion (L2), gE (5 mcg) and TQL-1055 choline salt (three groups: 5 mcg, 30 mcg, 100 mcg), gE (5 mcg) in an oil-in-water emulsion (L2) with TQL-1055 free acid (three groups: 5 mcg, 30 mcg, 100 mcg), gE (5 mcg) in an oil-in-water emulsion (L2) with TQL-1055 free acid (three groups: 5 mcg, 30 mcg, 100 mcg) and PHAD liposomes (20 mcg), and gE (5 mcg) with PHAD liposomes (20 mcg). Mice were immunized at Day 0 and Day 14. Groups were bled at Day 13 (post Dose 1) and Day 28 (post Dose 2) for serum analysis. The results are shown below.

Anti-gE IgG Endpoint Titers Post Dose 1

Figure 20:
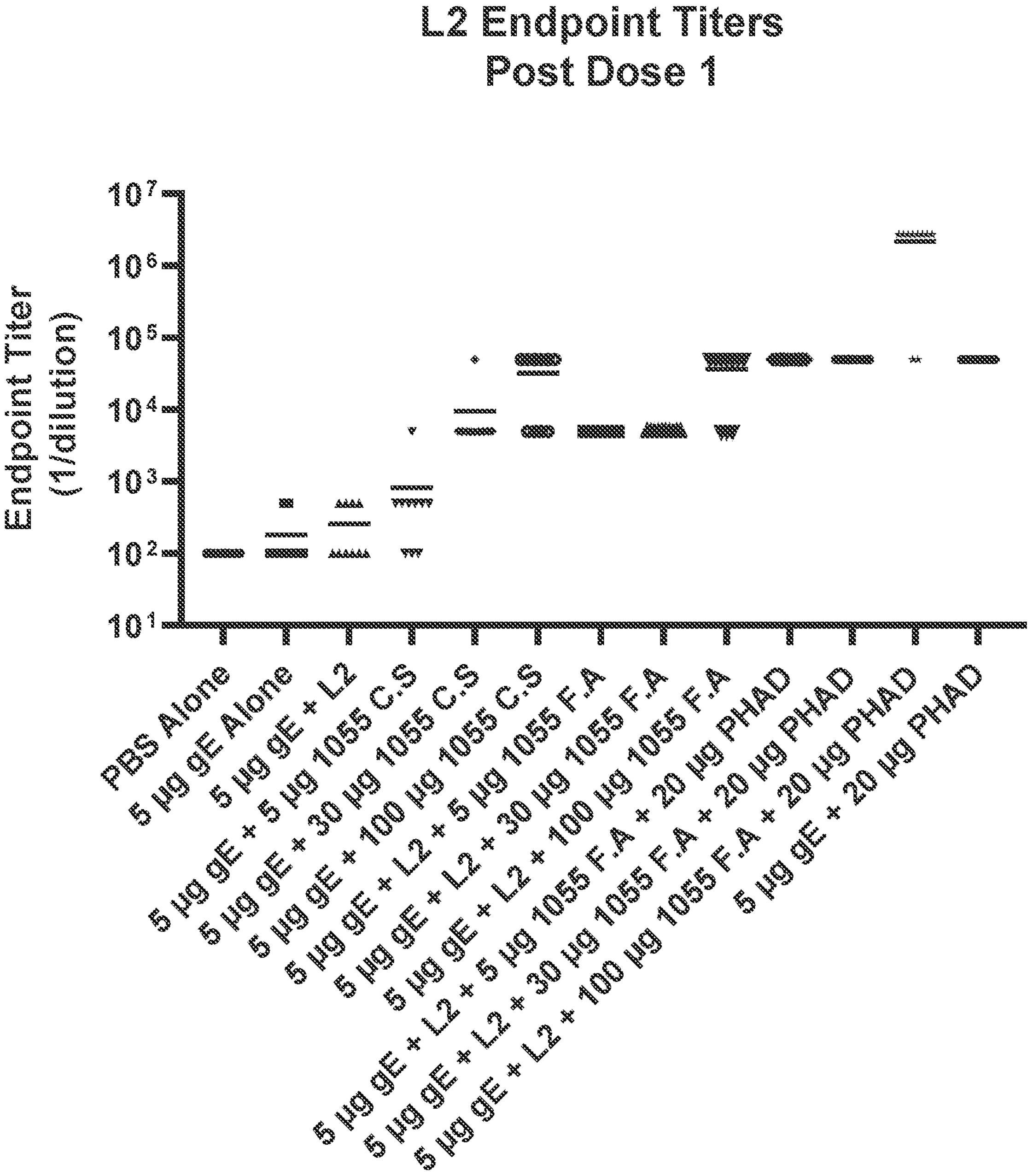
FIG. 20 depicts gE-specific total IgG titer data as explained in Example 3.

FIG. 20 is a graph depicting gE-specific total IgG titers post Dose 1 for the groups described above. For groups shown in FIG. 20, Table 3.1 below contains geometric mean titer (GMT) values and confidence intervals. Table 3.2 below shows adjusted P-values comparing various groups.

TABLE 3.1 gE-specific total IgG titers post dose 1

| | PBS Alone | 5 µg gE Alone | 5 µg gE + L2 | 5 µg gE + 5 µg 1055 C.S | 5 µg gE + 30 µg 1055 C.S | 5 µg gE + 100 µg 1055 C.S | 5 µg gE + L2 + 5 µg 1055 F.A |
|---|---|---|---|---|---|---|---|
| Number of values | 10 | 10 | 10 | 10 | 10 | 10 | 10 |
| Geometric mean | 100.0 | 138.0 | 190.4 | 388.4 | 6295 | 19905 | 5000 |
| Geometric SD factor | 1.000 | 1.971 | 2.296 | 3.240 | 2.071 | 3.284 | 1.000 |
| Lower 95% Cl of geo. mean | 100.0 | 84.91 | 105.0 | 167.5 | 3739 | 8503 | 5000 |
| Upper 95% Cl of geo. mean | 100.0 | 224.2 | 345.0 | 900.4 | 10597 | 46599 | 5000 |

TABLE 3.1 gE-specific total IgG titers post dose 1 (continued)

| | 5 µg gE + L2 + 30 µg 1055 F.A | 5 µg gE + L2 + 100 µg 1055 F.A | 5 µg gE + L2 + 5 µg 1055 F.A + 20 µg PHAD | 5 µg gE +L2 + 30 µg 1055 F.A + 20 µg PHAD | 5 µg gE + L2 + 100 µg 1055 F.A + 20 µg PHAD | 5 µg gE + 20 µg PHAD |
|---|---|---|---|---|---|---|
| Number of values | 10 | 10 | 10 | 10 | 10 | 10 |
| Geometric mean | 5000 | 25059 | 50000 | 50000 | 1233844 | 50000 |
| Geometric SD factor | 1.000 | 3.041 | 1.000 | 1.000 | 5.418 | 1.000 |
| Lower 95% CI of geo. mean | 5000 | 11309 | 50000 | 50000 | 368409 | 50000 |
| Upper 95% CI of geo. mean | 5000 | 55529 | 50000 | 50000 | 4132283 | 50000 |

TABLE 3.2

Group-wise comparisons between groups in Table 3.1

| Tukey's multiple comparisons test | Significant? | Summary | Adjusted P Value |
|---|---|---|---|
| PBS Alone vs. 5 µg gE Alone | No | ns | >0.9999 |
| PBS Alone vs. 5 µg gE + L2 | No | ns | >0.9999 |
| PBS Alone vs. 5 µg gE + 5 µg 1055 CS | No | ns | >0.9999 |
| PBS Alone vs. 5 µg gE + 30 µg 1055 CS | No | ns | >0.9999 |
| PBS Alone vs. 5 µg gE + 100 µg 1055 CS | No | ns | >0.9999 |
| PBS Alone vs. 5 µg gE + L2 + 5 µg 1055 FA | No | ns | >0.9999 |
| PBS Alone vs. 5 µg gE + L2 + 30 µg 1055 FA | No | ns | >0.9999 |
| PBS Alone vs. 5 µg gE + L2 + 100 µg 1055 FA | No | ns | >0.9999 |
| PBS Alone vs. 5 µg gE + L2 + 5 µg 1055 FA + 20 µg PHAD liposomes | No | ns | >0.9999 |
| PBS Alone vs. 5 µg gE + L2 + 30 µg 1055 FA + 20 µg PHAD liposomes | No | ns | >0.9999 |
| PBS Alone vs. 5 µg gE + L2 + 100 µg 1055 FA + 20 µg PHAD liposomes | Yes | **** | <0.0001 |
| PBS Alone vs. 5 µg gE + 20 µg PHAD liposomes | No | ns | >0.9999 |
| 5 µg gE Alone vs. 5 µg gE + L2 | No | ns | >0.9999 |
| 5 µg gE Alone vs. 5 µg gE + 5 µg 1055 CS | No | ns | >0.9999 |
| 5 µg gE Alone vs. 5 µg gE + 30 µg 1055 CS | No | ns | >0.9999 |
| 5 µg gE Alone vs. 5 µg gE + 100 µg 1055 CS | No | ns | >0.9999 |
| 5 µg gE Alone vs. 5 µg gE + L2 + 5 µg 1055 FA | No | ns | >0.9999 |
| 5 µg gE Alone vs. 5 µg gE + L2 + 30 µg 1055 FA | No | ns | >0.9999 |
| 5 µg gE Alone vs. 5 µg gE + L2 + 100 µg 1055 FA | No | ns | >0.9999 |
| 5 µg gE Alone vs. 5 µg gE + L2 + 5 µg 1055 FA + 20 µg PHAD liposomes | No | ns | >0.9999 |
| 5 µg gE Alone vs. 5 µg gE + L2 + 30 µg 1055 FA + 20 µg PHAD liposomes | No | ns | >0.9999 |
| 5 µg gE Alone vs. 5 µg gE + L2 + 100 µg 1055 FA + 20 µg PHAD liposomes | Yes | **** | <0.0001 |
| 5 µg gE Alone vs. 5 µg gE + 20 µg PHAD liposomes | No | ns | >0.9999 |
| 5 µg gE + L2 vs. 5 µg gE + 5 µg 1055 CS | No | ns | >0.9999 |
| 5 µg gE + L2 vs. 5 µg gE + 30 µg 1055 CS | No | ns | >0.9999 |
| 5 µg gE + L2 vs. 5 µg gE + 100 µg 1055 CS | No | ns | >0.9999 |
| 5 µg gE + L2 vs. 5 µg gE + L2 + 5 µg 1055 FA | No | ns | >0.9999 |
| 5 µg gE + L2 vs. 5 µg gE + L2 + 30 µg 1055 FA | No | ns | >0.9999 |

TABLE 3.2-continued

| Group-wise comparisons between groups in Table 3.1 | | | |
|---|---|---|---|
| Tukey's multiple comparisons test | Significant? | Summary | Adjusted P Value |
| 5 µg gE + L2 vs. 5 µg gE + L2 + 100 µg 1055 FA | No | ns | >0.9999 |
| 5 µg gE + L2 vs. 5 µg gE + L2 + 5 µg 1055 FA + 20 µg PHAD liposomes | No | ns | >0.9999 |
| 5 µg gE + L2 vs. 5 µg gE + L2 + 30 µg 1055 FA + 20 µg PHAD liposomes | No | ns | >0.9999 |
| 5 µg gE + L2 vs. 5 µg gE + L2 + 100 µg 1055 FA + 20 µg PHAD liposomes | Yes | **** | <0.0001 |
| 5 µg gE + L2 vs. 5 µg gE + 20 µg PHAD liposomes | No | ns | >0.9999 |
| 5 µg gE + 5 µg 1055 CS vs. 5 µg gE + 30 µg 1055 CS | No | ns | >0.9999 |
| 5 µg gE + 5 µg 1055 CS vs. 5 µg gE + 100 µg 1055 CS | No | ns | >0.9999 |
| 5 µg gE + 5 µg 1055 CS vs. 5 µg gE + L2 + 5 µg 1055 FA | No | ns | >0.9999 |
| 5 µg gE + 5 µg 1055 CS vs. 5 µg gE + L2 + 30 µg 1055 FA | No | ns | >0.9999 |
| 5 µg gE + 5 µg 1055 CS vs. 5 µg gE + L2 + 100 µg 1055 FA | No | ns | >0.9999 |
| 5 µg gE + 5 µg 1055 CS vs. 5 µg gE + L2 + 5 µg 1055 FA + 20 µg PHAD liposomes | No | ns | >0.9999 |
| 5 µg gE + 5 µg 1055 CS vs. 5 µg gE + L2 + 30 µg 1055 FA + 20 µg PHAD liposomes | No | ns | >0.9999 |
| 5 µg gE + 5 µg 1055 CS vs. 5 µg gE + L2 + 100 µg 1055 FA + 20 µg PHAD liposomes | Yes | **** | <0.0001 |
| 5 µg gE + 5 µg 1055 CS vs. 5 µg gE + 20 µg PHAD liposomes | No | ns | >0.9999 |
| 5 µg gE + 30 µg 1055 CS vs. 5 µg gE + 100 µg 1055 CS | No | ns | >0.9999 |
| 5 µg gE + 30 µg 1055 CS vs. 5 µg gE + L2 + 5 µg 1055 FA | No | ns | >0.9999 |
| 5 µg gE + 30 µg 1055 CS vs. 5 µg gE + L2 + 30 µg 1055 FA | No | ns | >0.9999 |
| 5 µg gE + 30 µg 1055 CS vs. 5 µg gE + L2 + 100 µg 1055 FA | No | ns | >0.9999 |
| 5 µg gE + 30 µg 1055 CS vs. 5 µg gE + L2 + 5 µg 1055 FA + 20 µg PHAD liposomes | No | ns | >0.9999 |
| 5 µg gE + 30 µg 1055 CS vs. 5 µg gE + L2 + 30 µg 1055 FA + 20 µg PHAD liposomes | No | ns | >0.9999 |
| 5 µg gE + 30 µg 1055 CS vs. 5 µg gE + L2 + 100 µg 1055 FA + 20 µg PHAD liposomes | Yes | **** | <0.0001 |
| 5 µg gE + 30 µg 1055 CS vs. 5 µg gE + 20 µg PHAD liposomes | No | ns | >0.9999 |
| 5 µg gE + 100 µg 1055 CS vs. 5 µg gE + L2 + 5 µg 1055 FA | No | ns | >0.9999 |
| 5 µg gE + 100 µg 1055 CS vs. 5 µg gE + L2 + 30 µg 1055 FA | No | ns | >0.9999 |
| 5 µg gE + 100 µg 1055 CS vs. 5 µg gE + L2 + 100 µg 1055 FA | No | ns | >0.9999 |
| 5 µg gE + 100 µg 1055 CS vs. 5 µg gE + L2 + 5 µg 1055 FA + 20 µg PHAD liposomes | No | ns | >0.9999 |
| 5 µg gE + 100 µg 1055 CS vs. 5 µg gE + L2 + 30 µg 1055 FA + 20 µg PHAD liposomes | No | ns | >0.9999 |
| 5 µg gE + 100 µg 1055 CS vs. 5 µg gE + L2 + 100 µg 1055 FA + 20 µg PHAD liposomes | Yes | **** | <0.0001 |
| 5 µg gE + 100 µg 1055 CS vs. 5 µg gE + 20 µg PHAD liposomes | No | ns | >0.9999 |
| 5 µg gE + L2 + 5 µg 1055 FA vs. 5 µg gE + L2 + 30 µg 1055 FA | No | ns | >0.9999 |
| 5 µg gE + L2 + 5 µg 1055 FA vs. 5 µg gE + L2 + 100 µg 1055 FA | No | ns | >0.9999 |
| 5 µg gE + L2 + 5 µg 1055 FA vs. 5 µg gE + L2 + 5 µg 1055 FA + 20 µg PHAD liposomes | No | ns | >0.9999 |
| 5 µg gE + L2 + 5 µg 1055 FA vs. 5 µg gE + L2 + 30 µg 1055 FA + 20 µg PHAD liposomes | No | ns | >0.9999 |
| 5 µg gE + L2 + 5 µg 1055 FA vs. 5 µg gE + L2 + 100 µg 1055 FA + 20 µg PHAD liposomes | Yes | **** | <0.0001 |
| 5 µg gE + L2 + 5 µg 1055 FA vs. 5 µg gE + 20 µg PHAD liposomes | No | ns | >0.9999 |
| 5 µg gE + L2 + 30 µg 1055 FA vs. 5 µg gE + L2 + 100 µg 1055 FA | No | ns | >0.9999 |
| 5 µg gE + L2 + 30 µg 1055 FA vs. 5 µg gE + L2 + 5 µg 1055 FA + 20 µg PHAD liposomes | No | ns | >0.9999 |
| 5 µg gE + L2 + 30 µg 1055 FA vs. 5 µg gE + L2 + 30 µg 1055 FA + 20 µg PHAD liposomes | No | ns | >0.9999 |
| 5 µg gE + L2 + 30 µg 1055 FA vs. 5 µg gE + L2 + 100 µg 1055 FA + 20 µg PHAD liposomes | Yes | **** | <0.0001 |
| 5 µg gE + L2 + 30 µg 1055 FA vs. 5 µg gE + 20 µg PHAD liposomes | No | ns | >0.9999 |
| 5 µg gE + L2 + 100 µg 1055 FA vs. 5 µg gE + L2 + 5 µg 1055 FA + 20 µg PHAD liposomes | No | ns | >0.9999 |
| 5 µg gE + L2 + 100 µg 1055 FA vs. 5 µg gE + L2 + 30 µg 1055 FA + 20 µg PHAD liposomes | No | ns | >0.9999 |
| 5 µg gE + L2 + 100 µg 1055 FA vs. 5 µg gE + L2 + 100 µg 1055 FA + 20 µg PHAD liposomes | Yes | **** | <0.0001 |
| 5 µg gE + L2 + 100 µg 1055 FA vs. 5 µg gE + 20 µg PHAD liposomes | No | ns | >0.9999 |
| 5 µg gE + L2 + 5 µg 1055 FA + 20 µg PHAD liposomes vs. 5 µg gE + L2 + 30 µg 1055 FA + 20 µg PHAD liposomes | No | ns | >0.9999 |
| 5 µg gE + L2 + 5 µg 1055 FA + 20 µg PHAD liposomes vs. 5 µg gE + L2 + 100 µg 1055 FA + 20 µg PHAD liposomes | Yes | **** | <0.0001 |
| 5 µg gE + L2 + 5 µg 1055 FA + 20 µg PHAD liposomes vs. 5 µg gE + 20 µg PHAD liposomes | No | ns | >0.9999 |
| 5 µg gE + L2 + 30 µg 1055 FA + 20 µg PHAD liposomes vs. 5 µg gE + L2 + 100 µg 1055 FA + 20 µg PHAD liposomes | Yes | **** | <0.0001 |
| 5 µg gE + L2 + 30 µg 1055 FA + 20 µg PHAD liposomes vs. 5 µg gE + 20 µg PHAD liposomes | No | ns | >0.9999 |
| 5 µg gE + L2 + 100 µg 1055 FA + 20 µg PHAD liposomes vs. 5 µg gE + 20 µg PHAD liposomes | Yes | **** | <0.0001 |

Anti-gE IgG Endpoint Titers Post Dose 2

Figure 21:
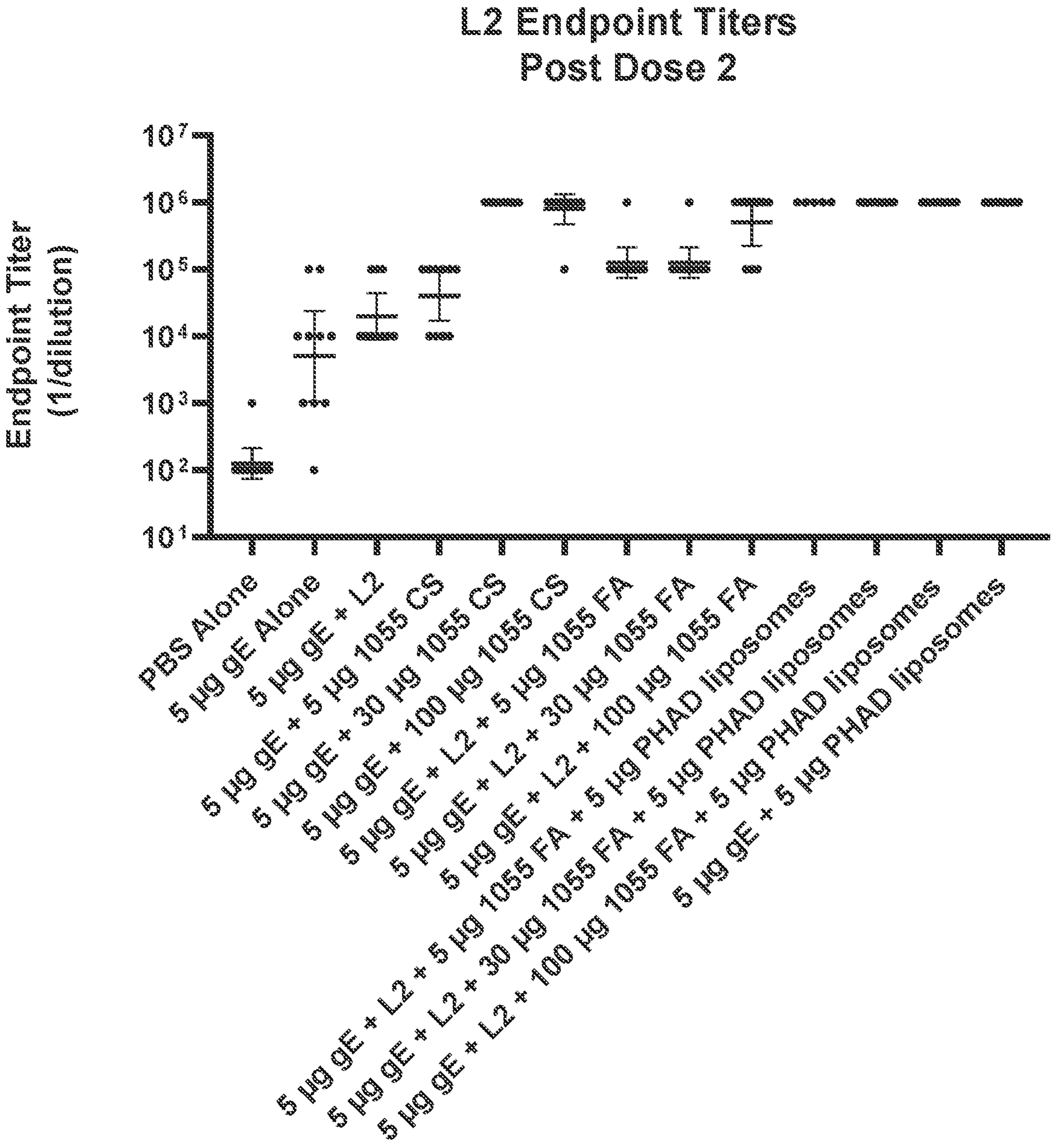
FIG. 21 depicts gE-specific total IgG titer data as explained in Example 3.

FIG. 21 is a graph depicting gE-specific total IgG titers post Dose 2 for the groups described above. For groups shown in FIG. 21, Table 3.3 below contains geometric mean titer (GMT) values and confidence intervals. Table 3.4 below shows adjusted P-values comparing various groups.

TABLE 3.3

| gE-specific total IgG titers post dose 2 | | | | | | | |
|---|---|---|---|---|---|---|---|
| | PBS Alone | 5 µg gE Alone | 5 µg gE + L2 | 5 µg gE + 5 µg 1055 C.S | 5 µg gE + 30 µg 1055 C.S | 5 µg gE + 100 µg 1055 C.S | 5 µg gE + L2 + 5 µg 1055 F.A |
| Number of values | 10 | 10 | 10 | 10 | 10 | 10 | 10 |
| Geometric mean | 125.9 | 5012 | 19953 | 39811 | 1000001 | 794329 | 125893 |
| Geometric SD factor | 2.071 | 8.886 | 3.041 | 3.284 | 1 | 2.071 | 2.071 |

TABLE 3.3-continued

| gE-specific total IgG titers post dose 2 | | | | | | | |
|---|---|---|---|---|---|---|---|
| Lower 95% CI of geo. mean | 74.78 | 1050 | 9004 | 17006 | 1000001 | 471829 | 74780 |
| Upper 95% CI of geo. mean | 211.9 | 23914 | 44213 | 93198 | 1000001 | 1337261 | 211941 |

| | 5 μg gE + L2 + 30 μg 1055 F.A | 5 μg gE + L2 + 100 μg 1055 F.A | 5 μg gE + L2 + 5 μg 1055 F.A +20 μg PHAD | 5 μg gE + L2 +30 μg 1055 F.A + 20 μg PHAD | 5 μg gE + L2 + 100 μg 1055 F.A + 20 μg PHAD | 5 μg gE + 20 μg PHAD |
|---|---|---|---|---|---|---|
| Number of values | 10 | 10 | 10 | 10 | 10 | 10 |
| Geometric mean | 125893 | 501188 | 1000001 | 1000001 | 1000001 | 1000001 |
| Geometric SD factor | 2.071 | 3.041 | 1 | 1 | 1 | 1 |
| Lower 95% CI of geo. mean | 74780 | 226178 | 1000001 | 1000001 | 1000001 | 1000001 |
| Upper 95% CI of geo. mean | 211941 | 1110582 | 1000001 | 1000001 | 1000001 | 1000001 |

TABLE 3.4

Group-wise comparisons between groups in Table 3.3

| Tukey's multiple comparisons test | Significant? | Summary | Adjusted P Value |
|---|---|---|---|
| PBS Alone vs. 5 μg gE Alone | No | ns | >0.9999 |
| PBS Alone vs. 5 μg gE + L2 | No | ns | >0.9999 |
| PBS Alone vs. 5 μg gE + 5 μg 1055 CS | No | ns | >0.9999 |
| PBS Alone vs. 5 μg gE + 30 μg 1055 CS | Yes | **** | <0.0001 |
| PBS Alone vs. 5 μg gE + 100 μg 1055 CS | Yes | **** | <0.0001 |
| PBS Alone vs. 5 μg gE + L2 + 5 μg 1055 FA | No | ns | 0.5482 |
| PBS Alone vs. 5 μg gE + L2 + 30 μg 1055 FA | No | ns | 0.5482 |
| PBS Alone vs. 5 μg gE + L2 + 100 μg 1055 FA | Yes | **** | <0.0001 |
| PBS Alone vs. 5 μg gE + L2 + 5 μg 1055 FA + 20 μg PHAD liposomes | Yes | **** | <0.0001 |
| PBS Alone vs. 5 μg gE + L2 + 30 μg 1055 FA + 20 μg PHAD liposomes | Yes | **** | <0.0001 |
| PBS Alone vs. 5 μg gE + L2 + 100 μg 1055 FA + 20 μg PHAD liposomes | Yes | **** | <0.0001 |
| PBS Alone vs. 5 μg gE + 20 μg PHAD liposomes | Yes | **** | <0.0001 |
| 5 μg gE Alone vs. 5 μg gE + L2 | No | ns | >0.9999 |
| 5 μg gE Alone vs. 5 μg gE + 5 μg 1055 CS | No | ns | >0.9999 |
| 5 μg gE Alone vs. 5 μg gE + 30 μg 1055 CS | Yes | **** | <0.0001 |
| 5 μg gE Alone vs. 5 μg gE + 100 μg 1055 CS | Yes | **** | <0.0001 |
| 5 μg gE Alone vs. 5 μg gE + L2 + 5 μg 1055 FA | No | ns | 0.7461 |
| 5 μg gE Alone vs. 5 μg gE + L2 + 30 μg 1055 FA | No | ns | 0.7461 |
| 5 μg gE Alone vs. 5 μg gE + L2 + 100 μg 1055 FA | Yes | **** | <0.0001 |
| 5 μg gE Alone vs. 5 μg gE + L2 + 5 μg 1055 FA + 20 μg PHAD liposomes | Yes | **** | <0.0001 |
| 5 μg gE Alone vs. 5 μg gE + L2 + 30 μg 1055 FA + 20 μg PHAD liposomes | Yes | **** | <0.0001 |
| 5 μg gE Alone vs. 5 μg gE + L2 + 100 μg 1055 FA + 20 μg PHAD liposomes | Yes | **** | <0.0001 |
| 5 μg gE Alone vs. 5 μg gE + 20 μg PHAD liposomes | Yes | **** | <0.0001 |
| 5 μg gE + L2 vs. 5 μg gE + 5 μg 1055 CS | No | ns | >0.9999 |
| 5 μg gE + L2 vs. 5 μg gE + 30 μg 1055 CS | Yes | **** | <0.0001 |
| 5 μg gE + L2 vs. 5 μg gE + 100 μg 1055 CS | Yes | **** | <0.0001 |
| 5 μg gE + L2 vs. 5 μg gE + L2 + 5 μg 1055 FA | No | ns | 0.8333 |
| 5 μg gE + L2 vs. 5 μg gE + L2 + 30 μg 1055 FA | No | ns | 0.8333 |
| 5 μg gE + L2 vs. 5 μg gE + L2 + 100 μg 1055 FA | Yes | **** | <0.0001 |
| 5 μg gE + L2 vs. 5 μg gE + L2 + 5 μg 1055 FA + 20 μg PHAD liposomes | Yes | **** | <0.0001 |
| 5 μg gE + L2 vs. 5 μg gE + L2 + 30 μg 1055 FA + 20 μg PHAD liposomes | Yes | **** | <0.0001 |
| 5 μg gE + L2 vs. 5 μg gE + L2 + 100 μg 1055 FA + 20 μg PHAD liposomes | Yes | **** | <0.0001 |
| 5 μg gE + L2 vs. 5 μg gE + 20 μg PHAD liposomes | Yes | **** | <0.0001 |
| 5 μg gE + 5 μg 1055 CS vs. 5 μg gE + 30 μg 1055 CS | Yes | **** | <0.0001 |
| 5 μg gE + 5 μg 1055 CS vs. 5 μg gE + 100 μg 1055 CS | Yes | **** | <0.0001 |
| 5 μg gE + 5 μg 1055 CS vs. 5 μg gE + L2 + 5 μg 1055 FA | No | ns | 0.9527 |
| 5 μg gE + 5 μg 1055 CS vs. 5 μg gE + L2 + 30 μg 1055 FA | No | ns | 0.9527 |
| 5 μg gE + 5 μg 1055 CS vs. 5 μg gE + L2 + 100 μg 1055 FA | Yes | **** | <0.0001 |
| 5 μg gE + 5 μg 1055 CS vs. 5 μg gE + L2 + 5 μg 1055 FA + 20 μg PHAD liposomes | Yes | **** | <0.0001 |
| 5 μg gE + 5 μg 1055 CS vs. 5 μg gE + L2 + 30 μg 1055 FA + 20 μg PHAD liposomes | Yes | **** | <0.0001 |
| 5 μg gE + 5 μg 1055 CS vs. 5 μg gE + L2 + 100 μg 1055 FA + 20 μg PHAD liposomes | Yes | **** | <0.0001 |
| 5 μg gE + 5 μg 1055 CS vs. 5 μg gE + 20 μg PHAD liposomes | Yes | **** | <0.0001 |
| 5 μg gE + 30 μg 1055 CS vs. 5 μg gE + 100 μg 1055 CS | No | ns | 0.9972 |
| 5 μg gE + 30 μg 1055 CS vs. 5 μg gE + L2 + 5 μg 1055 FA | Yes | **** | <0.0001 |

TABLE 3.4-continued

Group-wise comparisons between groups in Table 3.3

| Tukey's multiple comparisons test | Significant? | Summary | Adjusted P Value |
|---|---|---|---|
| 5 μg gE + 30 μg 1055 CS vs. 5 μg gE + L2 + 30 μg 1055 FA | Yes | **** | <0.0001 |
| 5 μg gE + 30 μg 1055 CS vs. 5 μg gE + L2 + 100 μg 1055 FA | No | ns | 0.0792 |
| 5 μg gE + 30 μg 1055 CS vs. 5 μg gE + L2 + 5 μg 1055 FA + 20 μg PHAD liposomes | No | ns | >0.9999 |
| 5 μg gE + 30 μg 1055 CS vs. 5 μg gE + L2 + 30 μg 1055 FA + 20 μg PHAD liposomes | No | ns | >0.9999 |
| 5 μg gE + 30 μg 1055 CS vs. 5 μg gE + L2 + 100 μg 1055 FA + 20 μg PHAD liposomes | No | ns | >0.9999 |
| 5 μg gE + 30 μg 1055 CS vs. 5 μg gE + 20 μg PHAD liposomes | No | ns | >0.9999 |
| 5 μg gE + 100 μg 1055 CS vs. 5 μg gE + L2 + 5 μg 1055 FA | Yes | **** | <0.0001 |
| 5 μg gE + 100 μg 1055 CS vs. 5 μg gE + L2 + 30 μg 1055 FA | Yes | **** | <0.0001 |
| 5 μg gE + 100 μg 1055 CS vs. 5 μg gE + L2 + 100 μg 1055 FA | No | ns | 0.6314 |
| 5 μg gE + 100 μg 1055 CS vs. 5 μg gE + L2 + 5 μg 1055 FA + 20 μg PHAD liposomes | No | ns | 0.9996 |
| 5 μg gE + 100 μg 1055 CS vs. 5 μg gE + L2 + 30 μg 1055 FA + 20 μg PHAD liposomes | No | ns | 0.9972 |
| 5 μg gE + 100 μg 1055 CS vs. 5 μg gE + L2 + 100 μg 1055 FA + 20 μg PHAD liposomes | No | ns | 0.9972 |
| 5 μg gE + 100 μg 1055 CS vs. 5 μg gE + 20 μg PHAD liposomes | No | ns | 0.9972 |
| 5 μg gE + L2 + 5 μg 1055 FA vs. 5 μg gE + L2 + 30 μg 1055 FA | No | ns | >0.9999 |
| 5 μg gE + L2 + 5 μg 1055 FA vs. 5 μg gE + L2 + 100 μg 1055 FA | Yes | **** | <0.0001 |
| 5 μg gE + L2 + 5 μg 1055 FA vs. 5 μg gE + L2 + 5 μg 1055 FA + 20 μg PHAD liposomes | Yes | **** | <0.0001 |
| 5 μg gE + L2 + 5 μg 1055 FA vs. 5 μg gE + L2 + 30 μg 1055 FA + 20 μg PHAD liposomes | Yes | **** | <0.0001 |
| 5 μg gE + L2 + 5 μg 1055 FA vs. 5 μg gE + L2 + 100 μg 1055 FA + 20 μg PHAD liposomes | Yes | **** | <0.0001 |
| 5 μg gE + L2 + 5 μg 1055 FA vs. 5 μg gE + 20 μg PHAD liposomes | Yes | **** | <0.0001 |
| 5 μg gE + L2 + 30 μg 1055 FA vs. 5 μg gE + L2 + 100 μg 1055 FA | Yes | **** | <0.0001 |
| 5 μg gE + L2 + 30 μg 1055 FA vs. 5 μg gE + L2 + 5 μg 1055 FA + 20 μg PHAD liposomes | Yes | **** | <0.0001 |
| 5 μg gE + L2 + 30 μg 1055 FA vs. 5 μg gE + L2 + 30 μg 1055 FA + 20 μg PHAD liposomes | Yes | **** | <0.0001 |
| 5 μg gE + L2 + 30 μg 1055 FA vs. 5 μg gE + L2 + 100 μg 1055 FA + 20 μg PHAD liposomes | Yes | **** | <0.0001 |
| 5 μg gE + L2 + 30 μg 1055 FA vs. 5 μg gE + 20 μg PHAD liposomes | Yes | **** | <0.0001 |
| 5 μg gE + L2 + 100 μg 1055 FA vs. 5 μg gE + L2 + 5 μg 1055 FA + 20 μg PHAD liposomes | No | ns | 0.3062 |
| 5 μg gE + L2 + 100 μg 1055 FA vs. 5 μg gE + L2 + 30 μg 1055 FA + 20 μg PHAD liposomes | No | ns | 0.0792 |
| 5 μg gE + L2 + 100 μg 1055 FA vs. 5 μg gE + L2 + 100 μg 1055 FA + 20 μg PHAD liposomes | No | ns | 0.0792 |
| 5 μg gE + L2 + 100 μg 1055 FA vs. 5 μg gE + 20 μg PHAD liposomes | No | ns | 0.0792 |
| 5 μg gE + L2 + 5 μg 1055 FA + 20 μg PHAD liposomes vs. 5 μg gE + L2 + 30 μg 1055 FA + 20 μg PHAD liposomes | No | ns | >0.9999 |
| 5 μg gE + L2 + 5 μg 1055 FA + 20 μg PHAD liposomes vs. 5 μg gE + L2 + 100 μg 1055 FA + 20 μg PHAD liposomes | No | ns | >0.9999 |
| 5 μg gE + L2 + 5 μg 1055 FA + 20 μg PHAD liposomes vs. 5 μg gE + 20 μg PHAD liposomes | No | ns | >0.9999 |
| 5 μg gE + L2 + 30 μg 1055 FA + 20 μg PHAD liposomes vs. 5 μg gE + L2 + 100 μg 1055 FA + 20 μg PHAD liposomes | No | ns | >0.9999 |
| 5 μg gE + L2 + 30 μg 1055 FA + 20 μg PHAD liposomes vs. 5 μg gE + 20 μg PHAD liposomes | No | ns | >0.9999 |
| 5 μg gE + L2 + 100 μg 1055 FA + 20 μg PHAD liposomes vs. 5 μg gE + 20 μg PHAD liposomes | No | ns | >0.9999 |

The invention claimed is:

1. An immunogenic composition comprising:

a varicella zoster virus antigen, wherein the varicella zoster virus antigen has the sequence of SEQ ID No. 9, and a compound of Formula I-4:

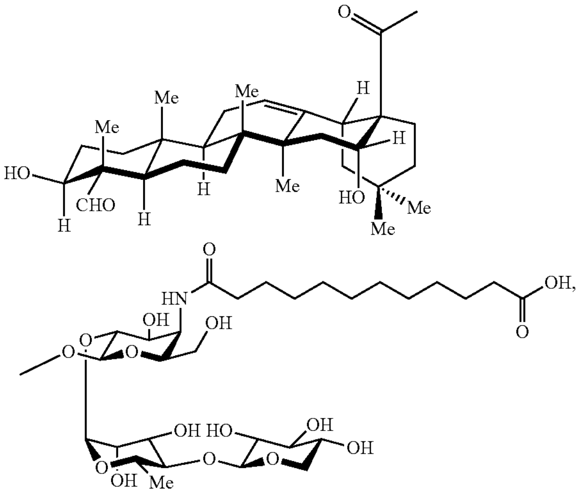

or a pharmaceutically acceptable salt thereof.

2. The immunogenic composition of claim 1, wherein the compound of Formula I-4 is in free acid form.

3. The immunogenic composition of claim 1, wherein the compound of Formula I-4 is in choline salt form.

4. The immunogenic composition of claim 1, further comprising a TLR4 agonist.

5. The immunogenic composition of claim 4, further comprising a liposome-forming compound.

6. The immunogenic composition of claim 5, wherein the liposome-forming compound forms liposomes containing the TLR4 agonist.

7. The immunogenic composition of claim 5, wherein the liposome-forming compound is selected from the group consisting of DOPC, DMPC, DMPG, cholesterol, and combinations thereof.

8. The immunogenic composition according to claim 4, further comprising an emulsion.

9. The immunogenic composition according to claim 8, wherein the emulsion is an oil-in-water emulsion.

10. The immunogenic composition according to claim 8, wherein the emulsion contains the compound of Formula I-4 pharmaceutically acceptable salt thereof.

11. The immunogenic composition according to claim 10, wherein the emulsion contains the TLR4 agonist.

12. The immunogenic composition according to claim 6, further comprising an emulsion.

13. The immunogenic composition according to claim 12, wherein the emulsion is an oil-in-water emulsion.

14. The immunogenic composition according to claim 12, wherein the emulsion contains the compound of Formula I-4 or pharmaceutically acceptable salt thereof.

15. A method of increasing cell-mediated immunity in a patient, said method comprising administering to said patient an effective amount of an immunogenic composition comprising a varicella zoster virus antigen, wherein the varicella zoster virus antigen has the sequence of SEQ ID No. 9, and a compound of Formula I-4:

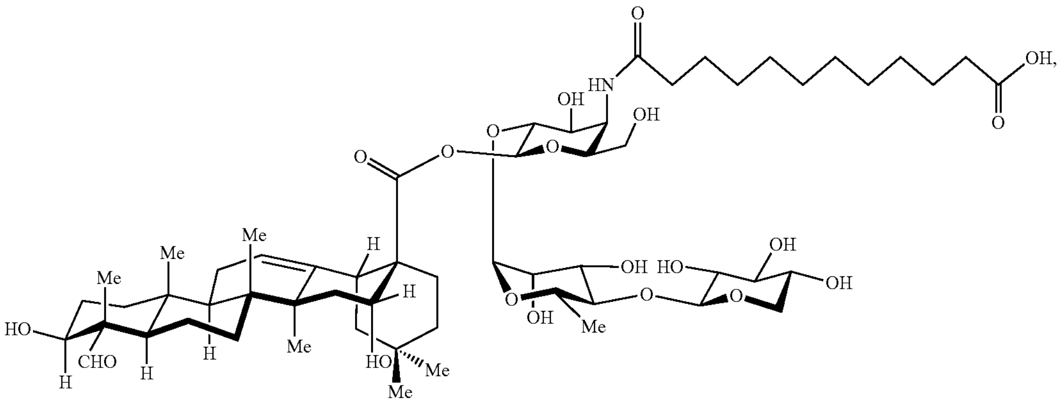

or a pharmaceutically acceptable salt thereof.

16. The method of claim 15, wherein the compound of Formula I-4 is in free acid form.

17. The method of claim 15, wherein the compound of Formula I-4 is in choline salt form.

18. The method of claim 15, further comprising a TLR4 agonist.

19. The method of claim 18, further comprising a liposome-forming compound.

20. The method of claim 19, wherein the liposome-forming compound forms liposomes containing the TLR4 agonist.

21. The method of claim 19, wherein the liposome-forming compound is selected from the group consisting of DOPC, DMPC, DMPG, cholesterol, and combinations thereof.

22. The method of claim 18, further comprising an emulsion.

23. The method of claim 22, wherein the emulsion is an oil-in-water emulsion.

24. The method of claim 22, wherein the emulsion contains the compound of Formula I-4 or pharmaceutically acceptable salt thereof.

25. The method of claim 24, wherein the emulsion contains the TLR4 agonist.

26. The method of claim 20, further comprising an emulsion.

27. The method of claim 26, wherein the emulsion is an oil-in-water emulsion.

28. The method of claim 26, wherein the emulsion contains the compound of Formula I-4 or pharmaceutically acceptable salt thereof.

* * * * *